(12) United States Patent
Kim et al.

(10) Patent No.: US 11,812,657 B2
(45) Date of Patent: Nov. 7, 2023

(54) ORGANIC ELECTRIC ELEMENT

(71) Applicant: Duk San Neolux Co., Ltd., Cheonan-si (KR)

(72) Inventors: Dae Sic Kim, Cheonan-si (KR); Jung Geun Lee, Cheonan-si (KR); Dong Hee Shin, Cheonan-si (KR); Bu Yong Yun, Cheonan-si (KR); Jeong Seok Kim, Cheongju-si (KR)

(73) Assignee: Duk San Neolux Co., Ltd.

( * ) Notice: Subject to any disclaimer, the term of this patent is extended or adjusted under 35 U.S.C. 154(b) by 0 days.

(21) Appl. No.: 18/312,639

(22) Filed: May 5, 2023

(65) Prior Publication Data

US 2023/0276699 A1    Aug. 31, 2023

Related U.S. Application Data

(62) Division of application No. 17/604,912, filed as application No. PCT/KR2020/008149 on Jun. 23, 2020.

(30) Foreign Application Priority Data

Jun. 24, 2019  (KR) .................. 10-2019-0075219

(51) Int. Cl.

| H01L 51/00 | (2006.01) |
|---|---|
| H01L 51/50 | (2006.01) |
| C09K 11/06 | (2006.01) |
| H10K 85/60 | (2023.01) |
| C07D 409/14 | (2006.01) |

(Continued)

(52) U.S. Cl.
CPC ......... *H10K 85/636* (2023.02); *C07D 409/14* (2013.01); *C07D 417/12* (2013.01); *C09K 11/06* (2013.01); *C09K 2211/1018* (2013.01); *H10K 50/84* (2023.02); *H10K 85/657* (2023.02); *H10K 85/6572* (2023.02); *H10K 85/6574* (2023.02); *H10K 85/6576* (2023.02)

(58) Field of Classification Search
CPC ............... H10K 85/636; H10K 85/656; H10K 85/6572; H10K 85/6574; H10K 85/6576
See application file for complete search history.

(56) References Cited

U.S. PATENT DOCUMENTS

| 2017/0155054 A1 | 6/2017 | Kim et al. |
| 2017/0186952 A1* | 6/2017 | Han .................. C07D 409/14 |
| 2018/0040829 A1* | 2/2018 | Lee .................... H10K 99/00 |

(Continued)

FOREIGN PATENT DOCUMENTS

| CN | 109734608 A | 5/2019 |
| CN | 110407829 A | 11/2019 |

(Continued)

OTHER PUBLICATIONS

International Search Report (in English and Korean) and Written Opinion of the ISA (in Korean) issued in PCT/KR2020/008149, dated Sep. 24, 2020; ISA/KR.

*Primary Examiner* — Vu A Nguyen

(74) *Attorney, Agent, or Firm* — Harness, Dickey & Pierce, P.L.C.

(57) ABSTRACT

The present disclosure relates to an organic electric element for realizing high luminous efficiency, and high heat resistance of the element, improve the color purity of the element, and increase the lifetime of the element.

9 Claims, 3 Drawing Sheets

(51) Int. Cl.
*C07D 417/12* (2006.01)
*H10K 50/84* (2023.01)

(56) References Cited

U.S. PATENT DOCUMENTS

2019/0296244 A1  9/2019  Mun et al.
2019/0296248 A1  9/2019  Mun et al.

FOREIGN PATENT DOCUMENTS

| CN | 110669025 A | 1/2020 |
| KR | 1020170052777 A | 5/2017 |
| KR | 1020170056425 A | 5/2017 |
| KR | 1020170064132 A | 6/2017 |
| KR | 101789998 B1 | 10/2017 |

* cited by examiner

ORGANIC ELECTRIC ELEMENT

CROSS-REFERENCE TO RELATED APPLICATIONS

This application is a divisional of U.S. application Ser. No. 17/604,912 filed Oct. 19, 2021, which is a U.S. National Phase Application under 35 U.S.C. 371 of International Application No. PCT/KR2020/008149, filed on Jun. 23, 2020, which claims the benefit of Korean Patent Application No. 10-2019-0075219, filed on Jun. 24, 2019. The entire disclosures of the above applications are incorporated herein by reference. In addition, if this patent application claims priority for countries other than the United States for the same reason as above, all contents thereof are incorporated into this patent application by reference.

TECHNICAL FIELD

The present disclosure relates to an organic electric element.

BACKGROUND ART

In general, an organic light emitting phenomenon refers to a phenomenon where electrical energy is converted into light energy using an organic material. An organic electric element using the organic light emitting phenomenon has a structure including an anode, a cathode, and an organic material layer disposed between the cathode and the anode. Here, in a number of cases, the organic material layer has a multi-layer structure made of different materials in order to improve the efficiency and stability of an organic electric element. For example, the organic material layer may include a hole injection layer, a hole transport layer, an emitting layer, an electron transport layer, an electron injection layer, and the like.

The materials used in the organic material layer may be categorized as emitting materials and charge transport materials, such as a hole injection material, a hole transport material, an electron transport material, and an electron injection material, depending on the function.

In addition, the emitting materials may be categorized as high-molecular weight types and low-molecular weight types depending on the molecular weight, and may be categorized as fluorescent materials based on singlet excitation of electrons and phosphorescent materials based on triplet excitation of electrons depending on the emission mechanism. In addition, the emitting materials may be categorized as blue, green, and red emitting materials depending on the color of emitted light, as well as yellow and orange emitting materials necessary for realizing more natural colors.

When a single material is used as an emitting material, a maximum emission wavelength may be shifted to a long wavelength and color purity may decrease because of interactions between molecules, or device efficiency may decrease because of an emission quenching effect. Thus, a host-dopant system may be used as an emitting material in order to increase color purity and increase luminous efficiency through energy transfer. According to the principle, when a small amount of dopant having a smaller energy band gap than the host of the emitting layer is added to the emitting layer, excitons generated in the emitting layer are transferred to the dopant to generate light with high efficiency. At this time, since the wavelength of the host is shifted to the wavelength band of the dopant, light having an intended wavelength may be obtained depending on the type of the dopant used.

Currently, in the portable display market, displays are increasing in size into large-area displays. Since portable displays are provided with a battery serving as a power supply, portable displays require more efficient consumption power than existing consumption power. In addition, in this situation, not only the challenge for efficient consumption power but also challenges for luminous efficiency and lifetime must be solved.

Efficiency, lifetime, a driving voltage and the like are related to each other. An increase in the efficiency leads to a relative decrease in the driving voltage, by which the crystallization of the organic material due to Joule heating during driving is reduced, thereby increasing the lifetime. However, simply improving the organic material layer may not maximize the efficiency. This is because, when the optimal combination of the energy level and Ti value between each organic material layer and the intrinsic properties (mobility, interfacial properties, etc.) of the material are achieved, both increased life and high efficiency may be achieved. Therefore, it is necessary to develop a light-emitting material that may efficiently achieve charge balance in the emitting layer while having high thermal stability.

That is, in order to sufficiently exhibit the excellent characteristics of the organic electric element, materials for forming the organic material layer in the element, such as a hole injection material, a hole transport material, a light-emitting material, an electron transport material, an electron injection material, and an emitting-auxiliary layer material, should be supported by stable and efficient materials. However, such a stable and efficient organic material layer material for an organic electric element has not been sufficiently developed yet.

Recently, technology for improving color purity and increasing efficiency by optimized optical thickness between an anode and a cathode in a top device with a resonance structure as well as research on improving device characteristics by giving performance changes of each material may be one of the important factors to improve the device performance. Compared with the bottom device structure of the non-resonant structure, the top device structure has a large optical energy loss due to surface plasmon polariton (SPP) because the formed light is reflected by the anode, which is a reflective film, and emitted toward the cathode.

Therefore, one of the important methods for improving the shape and efficiency of an organic electric element spectral is a method of using a capping layer for the top cathode. In general, four metals such as Al, Pt, Ag, Au are mainly used for electron emission in the SPP, and the surface plasmon is generated on the surface of the metal electrode. For example, when the cathode is used as the Ag, the light emitted by the Ag of the cathode is quenched by the SPP and the efficiency is reduced due to light energy loss by the Ag.

On the other hand, when the capping layer is used, the SPP is generated at the interface between the MgAg electrode and the high refractive organic material. In this case, TM (transverse magnetic) polarized light thereof is annihilated on the capping layer surface in the vertical direction by an evanescent wave and TM polarized light moving along the cathode and the capping layer is amplified by surface plasma resonance, thereby increasing the intensity of the peak and enabling eventually high efficiency and effective color purity control.

DISCLOSURE

Technical Problem

The present disclosure is intended to provide an organic electric element able to provide excellent luminous efficiency, high heat resistance, high color purity, and increased lifetime.

Technical Solution

According to an aspect, the present disclosure provides An organic electric element comprising a first electrode; a second electrode; an organic material layer located between the first electrode and the second electrode, and a capping layer disposed on at least one of one surface of the first electrode opposite to the organic material layer and one surface of the second electrode opposite to the organic material layer, wherein the capping layer comprises a compound represented by Formula 1 below.

Formula 1

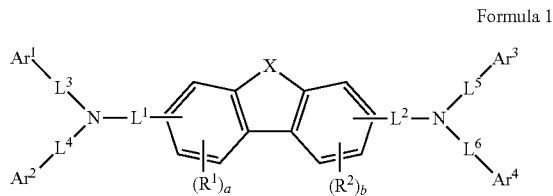

Advantageous Effects

As set forth above, it is possible to realize excellent luminous efficiency, high heat resistance, high color purity, and increased lifetime by including a capping layer using the compound according to the present disclosure.

MODE FOR INVENTION

Figure 1:
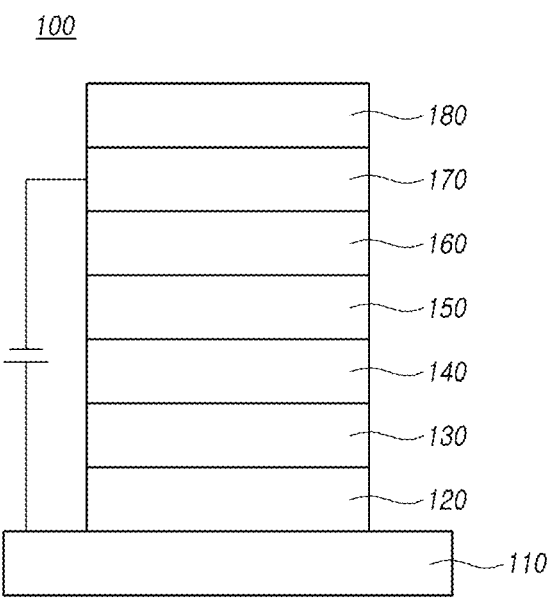
FIGS. 1 to 3 are cross-sectional views illustrating an organic light-emitting element according to an embodiment of the present disclosure.

Hereinafter, embodiments of the present disclosure will be described in detail with reference to the accompanying drawings.

In designating components of the drawings by reference numerals, the same components will be designated by the same reference numerals if possible although they are shown in different drawings. Further, in the following description of the present disclosure, a detailed description of known functions and configurations incorporated herein will be omitted in the situation in which the subject matter of the present disclosure may be rendered unclear thereby. When "includes", "has", "consisting of", etc. mentioned in this specification are used, other parts may be added unless "only" is used. When a component is expressed in a singular, it may include a case in which the plural is included unless otherwise explicitly stated.

In addition, terms, such as first, second, A, B, (a), or (b), may be used herein when describing components of the present disclosure. Each of these terminologies is not used to define an essence, order, or sequence of a corresponding component but used merely to distinguish the corresponding component from other components.

In the case that it is described that a certain component is "connected", "coupled", or "joined" to another component, it should be understood that another component may be "connected", "coupled", or "joined" to the component not only directly but also indirectly through an intervening component. Here, other components may be included in one or more of two or more components that are "connected", "coupled" or "connected" to each other.

In addition, in the case that it is described that a certain component, such as a layer, a film, an area, or a plate, is "above" or "over" another component, it should be understood that the component may be above another component not only "directly" but also indirectly through an intervening component. In contrast, in the case that it is described that a certain component is "directly above" another component, it should be understood that there is no intervening element.

When a temporal precedence or flow precedence relation is described with, for example, "after", "next", "before", etc., in the description of the temporal flow relationship related to the components, the operation method, the manufacturing method, etc., it may include a case where it is not continuous unless "immediately" or "directly" is used.

On the other hand, when numerical values or corresponding information for components are mentioned, even if there is no separate explicit description, the numerical values or the corresponding information may be interpreted as including an error range that may be caused by various factors (e.g., process factors, internal or external shocks, noise, etc.).

Unless otherwise stated, the term "halo" or "halogen", as used herein, includes fluorine (F), chlorine (Cl), bromine (Br), or iodine (I).

Unless otherwise stated, the term "alkyl" or "alkyl group", as used herein, has a single bond of 1 to 60 carbon atoms, and refers to saturated aliphatic functional radicals including a straight chain alkyl group, a branched chain alkyl group, a cycloalkyl (alicyclic) group, an alkyl-substituted cycloalkyl group, or a cycloalkyl-substituted alkyl group.

Unless otherwise stated, the term "haloalkyl" or "halogen alkyl", as used herein, includes a halogen-substituted alkyl group.

Unless otherwise stated, the term "alkenyl" or "alkynyl", as used herein, has a double or triple bond of 2 to 60 carbon atoms and includes a straight chain group or a branched chain group, but is not limited thereto.

Unless otherwise stated, the term "cycloalkyl" as used herein refers to, but is not limited to, alkyl forming a ring having 3 to 60 carbon atoms.

The term "alkoxy group" or "alkyloxy group", as used herein, refers to an alkyl group to which an oxygen radical is attached and, unless otherwise stated, has, but is not limited to, 1 to 60 carbon atoms.

The term "alkenoxyl group", "alkenoxy group", "alkenyloxyl group", or "alkenyloxy group" refers to an alkenyl group to which an oxygen radical is attached, and unless otherwise stated, has, but is not limited to, 2 to 60 carbon atoms.

Unless otherwise stated, the term "aryl group" or "arylene group", as used herein, has, but is not limited thereto, 6 to 60 carbon atoms. In this specification, the aryl group or the arylene group includes a monocyclic compound, a ring assembly, fused polycyclic systems, a spiro compound, or the like. For example, the aryl group include, but are not limited to, phenyl, biphenyl, naphthyl, anthryl, indenyl, phenanthryl, triphenylenyl, pyrenyl, peryleneyl, chrysenyl, naphthacenyl, fluoranthenyl, and the like. The naphthyl may include 1-naphthyl and 2-naphthyl, and the anthryl may include 1-anthryl, 2-anthryl and 9-anthryl.

Unless stated otherwise, the term "fluorenyl group" or "fluorenylene group", as used herein, may refer to a monovalent or divalent functional group of fluorene. In addition, the "fluorenyl group" or "fluorenylene group" may refer to a substituted fluorenyl group or a substituted fluorenylene group.

The term "substituted fluorenyl group" or "substituted fluorenylene group", as used herein, may refer to a monovalent or divalent functional group of substituted fluorene. The term "substituted fluorene" may refer to a compound in which at least one of substituent R, R', R", or R‴ below is a functional group other than hydrogen, and includes a case in which R and R' are bonded to form a spiro compound together with carbon atoms attached thereto.

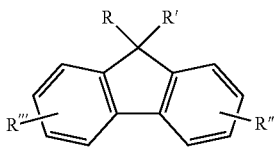

The term "spiro compound", as used herein, may have a 'spiro union', and the spiro linkage may refer to a linkage made by two rings sharing only one atom. At this time, the atoms shared by the two rings may refer to 'spiro atoms', and they may refer to 'monospiro-' compound, 'dispiro-' compound, compound, 'trispiro-' compound depending on the number of spiro atoms in a compound, respectively.

The term "heterocyclic group", as used herein, includes not only aromatic rings such as "heteroaryl group" or "heteroarylene group" but also non-aromatic rings, and unless stated otherwise, may refer to a ring having 2 to 60 carbon atoms including one or more of hetero atom, but it is not limited thereto. Unless stated otherwise, as used herein, the term "heteroatom" refers to N, O, S, P or Si, and the hetero ring group may refer to a monocyclic group including a heteroatom, a ring aggregate, a fused multiple ring system, a spy compound or the like.

In addition, the "heterocyclic group" or "hetero ring group", as used herein, may include rings having $SO_2$ in place of a ring-forming carbon atom. For example, the "heterocyclic group" includes the following compound:

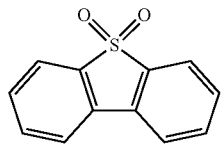

The term "ring", as used herein, refers to monocyclic rings and polycyclic rings, includes not only hydrocarbon rings but also hetero rings including at least one heteroatom, and includes aromatic rings and non-aromatic rings.

The term "polycyclic ring", as used herein, includes ring assemblies, such as biphenyl or terphenyl, fused polycyclic systems, and spiro compounds. The polycyclic ring includes not only aromatic compounds but also non-aromatic compounds, and includes not only hydrocarbon rings but also hetero rings including at least one heteroatom.

The term "aliphatic ring group", as used herein, may refer to a cyclic hydrocarbon other than an aromatic hydrocarbon, and include a monocyclic type, a ring assemblies, a fused multiple ring system, a spiro compound, and the like, Unless otherwise specified, it may refer to a ring having 3 to 60 carbon atoms. For example, even when benzene, which is an aromatic ring, and cyclohexane, which is a non-aromatic ring, are fused, it corresponds to an aliphatic ring.

The term "ring assembly", as used herein, may refer to a compound in which two or more rings (single rings or fused ring systems) are joined directly by single or double bonds and in which the number of such direct ring junctions is one less than the total number of ring systems in the compound. In ring assemblies, the same or different ring systems may be joined directly by single or double bonds. For example, in the case of an aryl group, it may be a biphenyl group, a terphenyl group, etc., but it is not limited thereto. [mu] The term "fused polycyclic system", as used herein, may refer to a form of fused rings sharing at least two atoms. For example, in the case of an aryl group, it may be a naphthalenyl group, a phenanthrenyl group, a fluorenyl group, etc., but it is not limited thereto.

In addition, in the case that prefixes are named consecutively, it means that substituents are listed in the order of the prefixes. For example, an aryl alkoxy group refers to an alkoxy group substituted with an aryl group, an alkoxy carbonyl group refers to a carbonyl group substituted with an alkoxy group, and an aryl carbonyl alkenyl group refers to an alkenyl group substituted with an arylcarbonyl group, with the arylcarbonyl group being a carbonyl group substituted with an aryl group.

Unless clearly stated otherwise, the term "substituted" in the term "substituted or non-substituted", as used herein, may refer to substitution with one or more substituents selected from the group consisting of, but not limited to, deuterium, a halogen, an amino group, a nitrile group, a nitro group, a $C_1$-$C_{20}$ alkyl group, a $C_1$-$C_{20}$ alkoxy group, a $C_1$-$C_{20}$ alkyl amine group, a $C_1$-$C_{20}$ alkylthiophene group, a $C_6$-$C_{20}$ arylthiophene group, a $C_2$-$C_{20}$ alkenyl group, a $C_2$-$C_{20}$ alkynil group, a $C_3$-$C_{20}$ cycloalkyl group, a $C_6$-$C_{20}$ aryl group, a $C_6$-$C_{20}$ aryl group substituted with deuterium, a $C_8$-$C_{20}$ aryl alkenyl group, a silane group, a boron group, a germanium group, and a $C_2$-$C_{20}$ hetero ring group including at least one heteroatom selected from the group consisting of O, N, S, Si, and P.

Herein, "the name of a functional group" corresponding to the aryl group, the arylene group, the hetero ring group, or the like illustrated as each symbol and a substituent thereof may be written in "the name of the functional group on which the valence thereof is reflected" or may be written in "the name of the parent compound thereof". For example, phenanthrene, i.e., a type of aryl group, may be written in group names by distinguishing the valence. That is, a monovalent phenanthrene "group" may be written as "phenanthryl (group)," while a divalent phenanthrene "group" may be written as "phenanthrylene (group)". In contrast, phenanthrene groups may be written as "phenanthrene", i.e. the name of the parent compound, regardless of the valence. Similarly, pyrimidine may be written as "pyrimidine" regardless of the valence or may be written in group names each corresponding to the valence, in which a monovalent pyrimidine group is written as pyrimidinyl (group) and a divalent pyrimidine group is written as pyrimidinylen (group). Accordingly, when the type of a substituent is written in the name of the parent compound in this specification, the written name may refer to an n-valence "group" formed by the desorption of a carbon atom and/or a heteroatom-bonded hydrogen atom from the parent compound.

In addition, unless clearly stated otherwise, formulas used herein are applied in the same manner as the definition of the substituent based on the exponential definition of the following Formula:

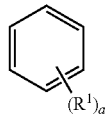

Here, when a is 0, there is no substituent $R^1$. When a is 1, a single substituent $R^1$ is attached to any one of the carbon atoms of the benzene ring. When a is 2 or 3, the substituent $R^1$ is attached in the following manner, where $R^1$ may be of the same or different values. When a is an integer between 4 and 6, the substituent $R^1$ is attached to a carbon atom of the benzene ring in a similar manner. Here, the illustration of hydrogen atoms attached to carbon atoms of the benzene ring will be omitted.

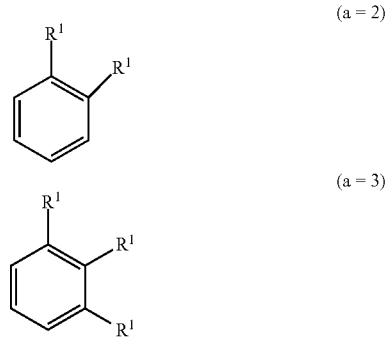

Herein, the expression "substituents bonded to form a ring" may refer to a case that adjacent groups are bonded to each other to form a single ring or fused multiple rings, and the single ring and the formed fused multiple rings may include not only hydrocarbon rings, but also includes heterocycles including at least one heteroatom, and may include aromatic and non-aromatic rings.

The organic electric element, as used herein, may refer to the organic light emitting diode including the constituent(s) between the anode and the cathode, or, and the anode, the cathode and the constituent(s) positioned therebetween.

In addition, in some cases, the organic electric element, as used herein, may refer to an organic light emitting diode and a panel including the same, or may refer to an electronic device including the panel and a circuit. Here, for example, the electronic device includes a display device, a lighting device, a solar cell, a portable or mobile terminal (e.g., a smart phone, a tablet, a PDA, an electronic dictionary, a PMP, etc.), a navigation terminal, a game machine, various TVs, and various computers. It may include all monitors, etc., but it is not limited thereto, and may be any type of device as long as the component(s) are included.

Figure 2:
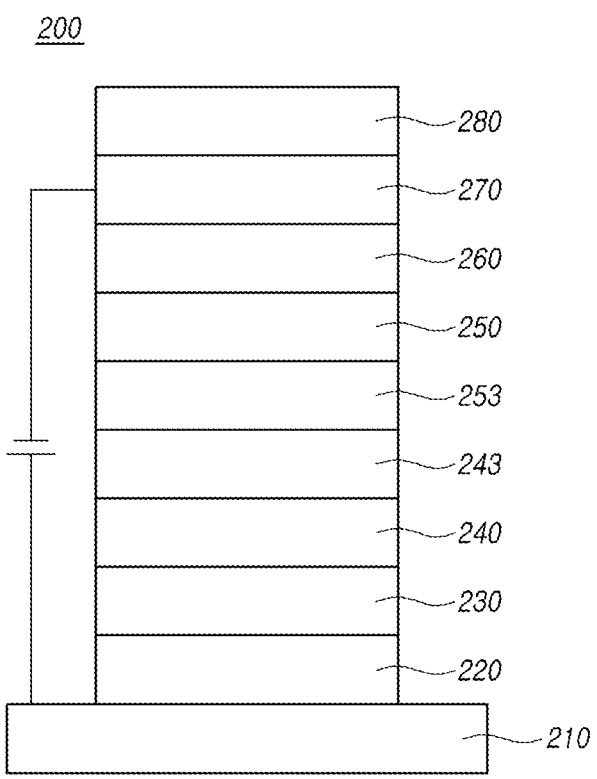
Figure 3:
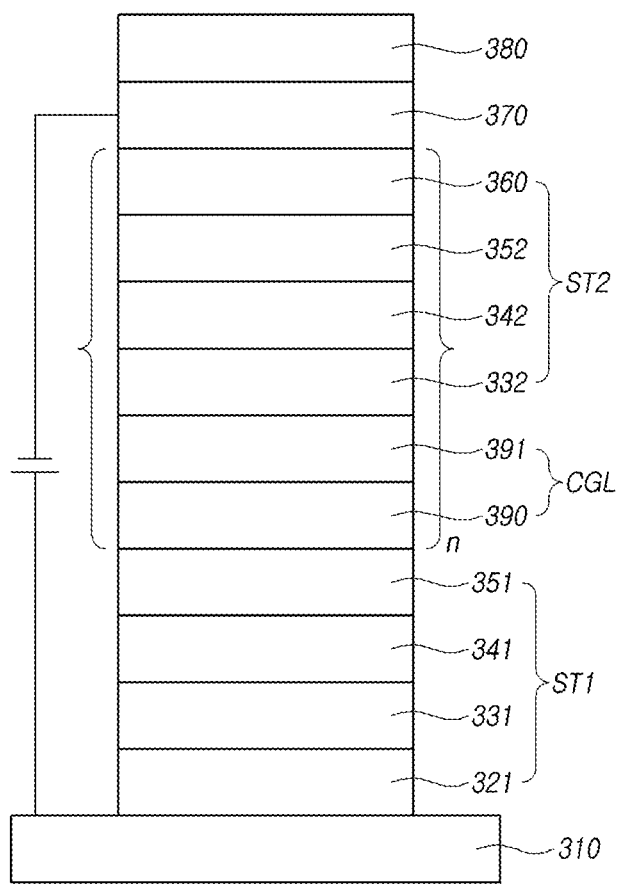

FIGS. 1 to 3 are cross-sectional views illustrating an organic light-emitting element according to an embodiment of the present disclosure.

An organic electric element according to an embodiment of the present disclosure may include a first electrode, a second electrode, an organic material layer positioned between the first electrode and the second electrode, and a capping layer disposed on at least one of one surface of the first electrode opposite to the organic material layer and one surface of the second electrode opposite to the organic material layer.

Referring to FIG. 1, the organic electric element according to the embodiment of the present disclosure, a first electrode 110, a second electrode 170, and the organic material layers 120, 130, 140, 150 and 160 positioned between the first electrode 110 and the second electrode 120 and the capping layer 180, and the capping layer 180 may be located on one surface of the second electrode 170 opposite to the organic material layer. In the embodiment shown in FIG. 1, the capping layer 180 is located on one surface of the second electrode 170, but in embodiments of the present disclosure, the capping layer 180 may be also located on one surface of the first electrode 110. When the capping layer 180 is positioned on one surface of the first electrode 110, the one surface is one surface opposite to the organic material layer among the surfaces of the first electrode 110, so that the capping layer 180 may be located in the lower part of the first electrode 110.

The thickness of the capping layer 180 may be 30 nm to 120 nm. The lower limit of the thickness of the capping layer 180 may be, for example, 40 nm or more, 50 nm or more, or 55 nm or more. The upper limit of the thickness of the capping layer 180 may be, for example, 100 nm or less, 80 nm or less, or 65 nm or less. When the thickness of the capping layer is adjusted within the above-described range, it is possible to provide the organic electric element having high luminous efficiency and color purity due to the surface plasma resonance.

The capping layer 180 may have a refractive index of 1.85 or more with respect to light having a wavelength of 450 nm to 750 nm. The upper limit of the refractive index of the capping layer for the light having a wavelength of 450 nm to 750 nm is not particularly limited, but may be, for example, 3.0 or less or 2.5 or less. When the refractive index of the capping layer is adjusted within the above-described range, it is possible to provide the organic electric element having high luminous efficiency and color purity due to the surface plasma resonance.

The first electrode 110 shown in FIG. 1 may be an anode and the second electrode 170 may be a cathode, and in the case of an inverted type, the first electrode is a cathode and the second electrode may be an anode.

The organic material layer may include a hole injection layer 120, a hole transport layer 130, a light emitting layer 140, an electron transport layer 150, and an electron injection layer 160. Specifically, the hole injection layer 120, the hole transport layer 130, the light emitting layer 140, the electron transport layer 150, and the electron injection layer 160 may be sequentially disposed on the first electrode 110.

In addition, referring to FIG. 2, in the organic electric element 200 according to another embodiment of the present disclosure, the hole injection layer 220 and the hole transport layer sequentially disposed on the first electrode 210 230, a buffer layer 243, a light emitting auxiliary layer 253, a light emitting layer 240, an electron transport layer 250, an electron injection layer 260, a second electrode 270, and a capping layer 280. In the embodiment shown in FIG. 2, the capping layer 280 is positioned on one surface of the second electrode 270, but in embodiments of the present disclosure, the capping layer 280 is located on one surface of the first electrode 210. When the capping layer 280 is positioned on one surface of the first electrode 210, the one surface is one surface opposite to the organic material layer among the surfaces of the first electrode 210, so that the capping layer 280 may be located in the lower part of the first electrode 210.

Meanwhile, although not shown in FIG. 2, an electron transport auxiliary layer may be further disposed between the light emitting layer 240 and the electron transport layer 250.

In addition, referring to FIG. 3, the organic electric element 300 according to another embodiment of the present disclosure may be that two or more stacks ST1 and ST2 of multi-layered organic material layers may be disposed between the first electrode 310 and the second electrode 370. For example, the first stack ST1 is disposed on the first electrode 310, the second stack ST2 is disposed on the first stack ST1, the second electrode 370 is disposed on the second stack ST2, and the capping layer 380 may be disposed on the second electrode 370. A charge generating layer CGL may be disposed between the first stack ST1 and the second stack ST2. In the embodiment shown in FIG. 3, the capping layer 380 is positioned on one surface of the second electrode 370, but in embodiments of the present disclosure, the capping layer 380 is located on one surface of the first electrode 310. When the capping layer 380 is positioned on one surface of the first electrode 310, the one surface is one surface of the first electrode 310 opposite to the organic material layer, so that the capping layer 380 may be located in the lower part of the first electrode 310.

Specifically, the organic electric element 300 includes the first electrode 310, the first stack ST1, the charge generating layer CGL, the second stack ST2, and the second electrode 370 and the capping layer 380.

The first stack ST1 is an organic material layer formed on the first electrode 310, which includes a first hole injection layer 321, a first hole transport layer 331, a first light emitting layer 341 and the first electron transport layer 351. The second stack ST2 may include a second hole transport layer 332, a second emitting layer 342, and a second electron transport layer 352. Additionally, an electron injection layer 360 may be included between the second electrode and the second electron transport layer. As such, the first stack and the second stack may be an organic material layer having the same stacked structure.

The charge generating layer CGL may include a first charge generating layer 390 and a second charge generating layer 391. The charge generating layer CGL is disposed between the first and second light emitting layers 341 and 342, thereby increasing the efficiency of a current generated in each of the light emitting layers and may play a role of smoothly distributing charges.

For example, the first emitting layer 341 may include a light emitting material including a blue fluorescent dopant in a blue host, and the second emitting layer 342 includes a material doped with both a greenish yellow dopant and a red dopant in a green host, but the material of the first and second light emitting layers 341 and 342 according to an embodiment of the present disclosure is not limited thereto.

The charge generating layer CGL and the second stack ST2 may be repeatedly positioned n times where n is a positive integer. For example, n may be an integer of 1 to 5. For example, when n is 2, the charge generating layer CGL and the third stack may be further stacked on the second stack ST2.

The capping layers 180, 280, and 380 may be disposed on one surface opposite to the organic material layer among the surfaces of the first electrode 110, 210, 310 and one surface opposite to the organic material layer among the surfaces of the second electrode 170, 270, 370 in the FIGS. 1-3, When the capping layer is disposed thereon, the light efficiency of the organic electric element may be improved. For example, when the capping layer is positioned below the first electrodes 110, 210, and 310 or above the second electrodes 170, 270, 370, light emitted through the electrodes is emitted from the capping layer having a relatively high refractive index. As it passes through, the wavelength of light is amplified and the luminous efficiency may be increased.

In the case of a top emission organic light emitting element, the capping layers 180, 280, 380 may play a role in reducing optical energy loss due to the surface plasmon polaritons (SPPs) in the second electrodes 170, 270, 370. In the case of a bottom emission organic electric element, the capping layers 180, 280, and 380 may serve as a buffer for the second electrodes 170, 270, and 370.

On the other hand, when a plurality of light-emitting layers are formed by a multi-layer stack structure method as shown in FIG. 3, the organic electric element that emits white light by the mixing effect of light emitted from each light-emitting layer can be manufactured.

An organic light emitting element according to an embodiment of the present disclosure may be fabricated using a variety of deposition methods. The organic light emitting element may be fabricated using a deposition method, such as physical vapor deposition (PVD) or chemical vapor deposition (CVD). For example, the organic light emitting element may be fabricated by: forming the anodes 110, 210, and 310 by depositing a metal, a conductive metal oxide or an alloy thereof on a substrate, forming the organic material layer including the hole injection layers 120, 220 and 321, the hole transport layers 130, 230 331 and 332, the light emitting layers 140, 240, 341 and 342, the electron transport layers 150, 250, 351 and 352, and the electron injection layer 160, 260 and 360 thereon, and depositing a material used as the cathodes 170, 270, and 370 thereon.

In addition, the organic material layer may be fabricated into a smaller number of layers by a solution process or a solvent process, such as a spin coating process, a nozzle printing process, an inkjet printing process, a slot coating process, a dip coating process, a roll-to-roll process, a doctor blading process, a screen printing process, or a thermal transfer process, using a variety of polymer materials. Since the organic material layer according to the present disclosure may be formed by a variety of methods, the scope of the right of the present disclosure is not limited by the method forming the organic material layer.

The organic electric element according to the present disclosure may be a top emission type, a bottom emission type, or a dual emission type depending on the material used therein.

The white organic light-emitting device (WOLED) has merits, such as the ease of realization of high resolution, superior process ability, and the ability thereof to be fabricated using existing color filter technologies for liquid crystal displays (LCDs). For the WOLED mainly used in a backlight unit, a variety of structures have been proposed and patented. Representative are a planar side-by-side arrangement of red (R), green (G), and blue (B) light-emitting structures, a vertical stack arrangement of RGB light-emitting structures, and a color conversion material (CCM) structure in which electroluminescence from a blue (B) organic emitting layer and photo-luminescence from an inorganic luminescent material using the electroluminescence are used. The present disclosure may be applied to the WOLED.

In embodiments of the present disclosure, the hole injection layers 120, 220 and 321, the hole transport layers 130, 230, 331 and 332, the buffer layer 243, the light emission auxiliary layer 253, the electron transport layers 150, 250, 351 and 352, the electron injection layers 160, 260 and 360, the light emitting layers 140, 240, 341 and 342, or the capping layers 180, 280 and 380 may include the compounds represented by the Formula 1 below. For example, the capping layers 180, 280 and 380 may include a compound represented by the Formula 1 below.

Hereinafter, the compound according to the aspect of the present disclosure is represented by the Formula 1 below.

Formula 1

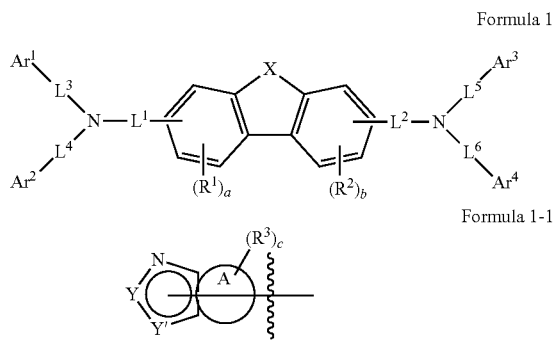

Formula 1-1

The substituents and linking groups described in the Formula 1 will be described as follows.

$Ar^1$ to $Ar^4$ may be each independently selected from a group consisting of a $C_1$-$C_{50}$ alkyl group; a $C_2$-$C_{20}$ alkenyl group; a $C_6$-$C_{60}$ aryl group; a fluorenyl group; a $C_2$-$C_{60}$ hetero ring group comprising at least one heteroatom selected from among O, N, S, Si, or P; and a fused ring group of a $C_3$-$C_{60}$ aliphatic ring and a $C_6$-$C_{60}$ aromatic ring.

For example, $Ar^1$ to $Ar^4$ may be each independently selected from a group consisting of a $C_6$-$C_{60}$ aryl group; a fluorenyl group; and a $C_2$-$C_{60}$ hetero ring group comprising at least one heteroatom selected from among O, N, S, Si, or P.

When $Ar^1$ to $Ar^4$ are respectively an aryl group, each of $Ar^1$ to $Ar^4$ may be independently a $C_6$-$C_{60}$ aryl group, a $C_6$-$C_{40}$ aryl group, $C_6$-$C_{25}$ aryl group, or a $C_6$-$C_{10}$ aryl group. In this case, $Ar^1$ to $Ar^4$ may be the same as or different from each other.

When $Ar^1$ to $Ar^4$ are respectively a hetero ring group, each of $Ar^1$ to $Ar^4$ may be a $C_2$-$C_{60}$ hetero ring group, a $C_2$-$C_{40}$ hetero ring group or a $C_2$-$C_{20}$ hetero ring group. In this case, $Ar^1$ to $Ar^4$ may be the same as or different from each other.

At least one of $Ar^1$ to $Ar^4$ is represented by formula 1-1.

$L^1$ and $L^2$ may be each independently selected from a group consisting of a single bond; a $C_1$-$C_{50}$ alkylene group; a $C_2$-$C_{20}$ alkenylene group; $C_6$-$C_{60}$ arylene group; fluorenylene group; a $C_2$-$C_{60}$ hetero ring group comprising at least one heteroatom selected from among O, N, S, Si, or P; and a fused ring group of a $C_3$-$C_{60}$ aliphatic ring and a $C_6$-$C_{60}$ aromatic ring.

When $L^1$ and $L^2$ are respectively an arylene group, each of $L^1$ and $L^2$ may be independently a $C_6$-$C_{60}$ arylene group, a $C_6$-$C_{40}$ arylene group, a $C_6$-$C_{25}$ arylene group, or $C_6$-$C_{10}$ arylene group. In this case, $L^1$ and $L^2$ may be the same as or different from each other.

When $L^1$ and $L^2$ are respectively a hetero ring group, each of $L^1$ and $L^2$ may be a $C_2$-$C_{60}$ hetero ring group, a $C_2$-$C_{40}$ hetero ring group or a $C_2$-$C_{20}$ hetero ring group. In this case, $L^1$ and $L^2$ may be the same as or different from each other.

$L^3$ to $L^6$ may be each independently selected from a group consisting of a single bond; a $C_1$-$C_{50}$ alkylene group; a $C_2$-$C_{20}$ alkenylene group; $C_6$-$C_{60}$ arylene group; fluorenylene group; a $C_2$-$C_{60}$ hetero ring group comprising at least one heteroatom selected from among O, N, S, Si, or P; and a fused ring group of a $C_3$-$C_{60}$ aliphatic ring and a $C_6$-$C_{60}$ aromatic ring.

When $L^3$ to $L^6$ are respectively an arylene group, each of $L^3$ to $L^6$ may be independently a $C_6$-$C_{60}$ arylene group, a $C_6$-$C_{40}$ arylene group, a $C_6$-$C_{25}$ arylene group, or $C_6$-$C_{10}$ arylene group. In this case, $L^3$ to $L^6$ may be the same as or different from each other.

When $L^3$ to $L^6$ are respectively a hetero ring group, each of $L^3$ to $L^6$ may be a $C_2$-$C_{60}$ hetero ring group, a $C_2$-$C_{40}$ hetero ring group or a $C_2$-$C_{20}$ hetero ring group. In this case, $L^3$ to $L^6$ may be the same as or different from each other.

$R^1$ and $R^2$ may be each independently selected from the group consisting of deuterium; a $C_1$-$C_{50}$ alkyl group; a $C_2$-$C_{20}$ alkenyl group; a $C_6$-$C_{60}$ aryl group; a fluorenyl group; a $C_2$-$C_{60}$ hetero ring group comprising at least one heteroatom selected from among O, N, S, Si, or P; a fused ring group of a $C_3$-$C_{60}$ aliphatic ring and a $C_6$-$C_{60}$ aromatic ring; and -L'-N($R^a$) ($R^b$), and one or more adjacent $R^1$s are the same or different and a plurality of $R^1$s are bonded to form a ring and one or more adjacent $R^2$s are the same or different and a plurality of $R^2$s are bonded to form a ring.

For example, $R^1$ and $R^2$ may be each independently selected from the group consisting of deuterium; a $C_6$-$C_{60}$ aryl group; a fluorenyl group; and a $C_2$-$C_{60}$ hetero ring group comprising at least one heteroatom selected from among O, N, S, Si, or P.

When $R^1$ and $R^2$ are respectively an aryl group, each of $R^1$ and $R^2$ may be independently a $C_6$-$C_{60}$ aryl group, a $C_6$-$C_{40}$ aryl group, a $C_6$-$C_{25}$ aryl group, or a $C_6$-$C_{10}$ aryl group. In this case, $R^1$ and $R^2$ may be the same as or different from each other.

When $R^1$ and $R^2$ are respectively a hetero ring group, each of $R^1$ and $R^2$ may be a $C_2$-$C_{60}$ hetero ring group, a $C_2$-$C_{40}$ hetero ring group or a $C_2$-$C_{20}$ hetero ring group. In this case, $R^1$ and $R^2$ may be the same as or different from each other.

$R^3$ may be selected from the group consisting of deuterium; a $C_1$-$C_{50}$ alkyl group; a $C_2$-$C_{20}$ alkenyl group; a $C_6$-$C_{60}$ aryl group; a fluorenyl group; a $C_2$-$C_{60}$ hetero ring group comprising at least one heteroatom selected from among O, N, S, Si, or P; a fused ring group of a $C_3$-$C_{60}$ aliphatic ring and a $C_6$-$C_{60}$ aromatic ring; and -L'-N($R^a$) ($R^b$) and one or more adjacent $R^3$s are the same or different and a plurality of $R^3$s are bonded to form a ring.

For example, $R^3$ may be each independently selected from the group consisting of deuterium; a $C_6$-$C_{60}$ aryl group; a fluorenyl group; and a $C_2$-$C_{60}$ hetero ring group comprising at least one heteroatom selected from among O, N, S, Si, or P.

When $R^3$ is respectively an aryl group, each of $R^3$ may be independently a $C_6$-$C_{60}$ aryl group, a $C_6$-$C_{40}$ aryl group, a $C_6$-$C_{25}$ aryl group, or a $C_6$-$C_{10}$ aryl group. In this case, a plurality of $R^3$s $R^2$s are the same or different.

When $R^3$ are respectively a hetero ring group, each of $R^3$ may be a $C_2$-$C_{60}$ hetero ring group, a $C_2$-$C_{40}$ hetero ring group or a $C_2$-$C_{20}$ hetero ring group. In this case, a plurality of $R^3$s $R^2$s are the same or different.

a and b may be each independently an integer of 0 to 3.

c may be an integer of 0 to 4, and when two or more of $Ar^1$ to $Ar^4$ may be represented by the formula 1-1, a plurality of c's may be the same or may be different.

L' may be each independently selected from a group consisting of a single bond; $C_6$-$C_{60}$ arylene group; fluorenylene group; a $C_2$-$C_{60}$ hetero ring group comprising at least one heteroatom selected from among O, N, S, Si, or P; and a fused ring group of a $C_3$-$C_{60}$ aliphatic ring and a $C_6$-$C_{60}$ aromatic ring.

$R^a$ and $R^b$ may be each independently selected from a group consisting of a $C_6$-$C_{60}$ aryl group; a fluorenyl group; ; a $C_2$-$C_{60}$ hetero ring group comprising at least one heteroatom selected from among O, N, S, Si, or P; and a fused ring group of a $C_3$-$C_{60}$ aliphatic ring and a $C_6$-$C_{60}$ aromatic ring.

X may be 0 or S.

Ring A may be each independently a $C_6$-$C_{30}$ aryl group, a $C_6$-$C_{25}$ aryl group or a $C_6$-$C_{10}$ aryl group. The ring A is an aryl group satisfying the above carbon number range, and may be an aryl group fused to a substituent represented by the Formula 1-1. For example, the ring A may be each independently selected from the group consisting of benzene, naphthalene, phenanthrene, and anthracene.

Y may be each independently $CR^aR^b$ or $NR^c$, and when Y is bonded to the formula 1, it may be N or C. when Y may be plural, a plurality of Ys may be the same or may be different.

Y' may be each independently N, O or S.

$R^a$, $R^b$ and $R^c$ may be each independently hydrogen; deuterium; a $C_1$-$C_{50}$ alkyl group; a $C_2$-$C_{20}$ alkenyl group; a $C_6$-$C_{60}$ aryl group; a fluorenyl group; a $C_2$-$C_{60}$ hetero ring group comprising at least one heteroatom selected from among O, N, S, Si, or P; and a fused ring group of a $C_3$-$C_{60}$ aliphatic ring and a $C_6$-$C_{60}$ aromatic ring; or combinations thereof.

When $R^a$, $R^b$ and $R^c$ are respectively an aryl group, each of $R^a$, $R^b$ and $R^c$ may be independently a $C_6$-$C_{60}$ aryl group, a $C_6$-$C_{40}$ aryl group, $C_6$-$C_{25}$ aryl group, or a $C_6$-$C_{10}$ aryl group. In this case, $R^a$, $R^b$ and $R^c$ may be the same as or different from each other.

When $R^a$, $R^b$ and $R^c$ are respectively a hetero ring group, each of $R^a$, $R^b$ and $R^c$ may be a $C_2$-$C_{60}$ hetero ring group, a $C_2$-$C_{40}$ hetero ring group or a $C_2$-$C_{20}$ hetero ring group. In this case, $R^a$, $R^b$ and $R^c$ may be the same as or different from each other.

adjacent $L^1$ and $R^1$ may be bonded to form a ring.
adjacent $L^1$ and $Ar^1$ may be bonded to form a ring.
adjacent $L^1$ and Are may be bonded to form a ring.
adjacent $L^1$ and $L^3$ may be bonded to form a ring.
adjacent, $L^1$ and $L^4$ may be bonded to form a ring.
adjacent $L^2$ and $R^2$ may be bonded to form a ring.
adjacent $L^2$ and Ara may be bonded to form a ring.
adjacent $L^2$ and $Ar^4$ may be bonded to form a ring.
adjacent $L^2$ and $L^5$ may be bonded to form a ring.
adjacent $L^2$ and $L^6$ may be bonded to form a ring.

In $Ar^1$ to $Ar^4$, $L^1$ to $L^6$, $R^1$ to $R^3$, $R^a$ and $R^b$, each of the aryl group, the fluorenyl group, the hetero ring group, the fused ring group, alkyl group, the alkenyl group, the alkylene group, the arylene group and the fluorenylene group may be further substituted with one or more substituents selected from a group consisting of deuterium; a nitro group; a nitrile group; a halogen group; an amino group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ hetero ring group; a $C_3$-$C_{20}$ cycloalkyl group; a $C_7$-$C_{20}$ aryl alkyl group; and a $C_8$-$C_{20}$ aryl alkenyl group. Accordingly, when $Ar^1$ to $Ar^4$, $L^1$ to $L^6$, $R^1$ to $R^3$, $R^a$ and $R^b$ are understood as primary substituents, the additionally substituted substituents may be understood as secondary substituents.

the additionally substituted substituents as the secondary substituents may be bonded to form a ring, and each of the substituents is further substituted with one or more substituents selected from a group consisting of deuterium; a nitro group; a nitrile group; a halogen group; an amino group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ hetero ring group; a $C_3$-$C_{20}$ cycloalkyl group; a $C_7$-$C_{20}$ aryl alkyl group; and a $C_8$-$C_{20}$ aryl alkenyl group, and the substituents are allowed to be bonded to form a ring. The additionally substituted substituents from the second substituents may be understood as third substituents.

$L^1$ to $L^6$ may be any one of Formulas a-1 to a-13 below.

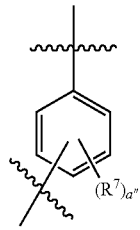

Formula a-1

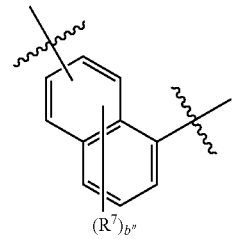

Formula a-2

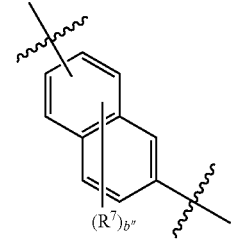

Formula a-3

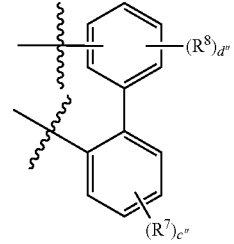

Formula a-4

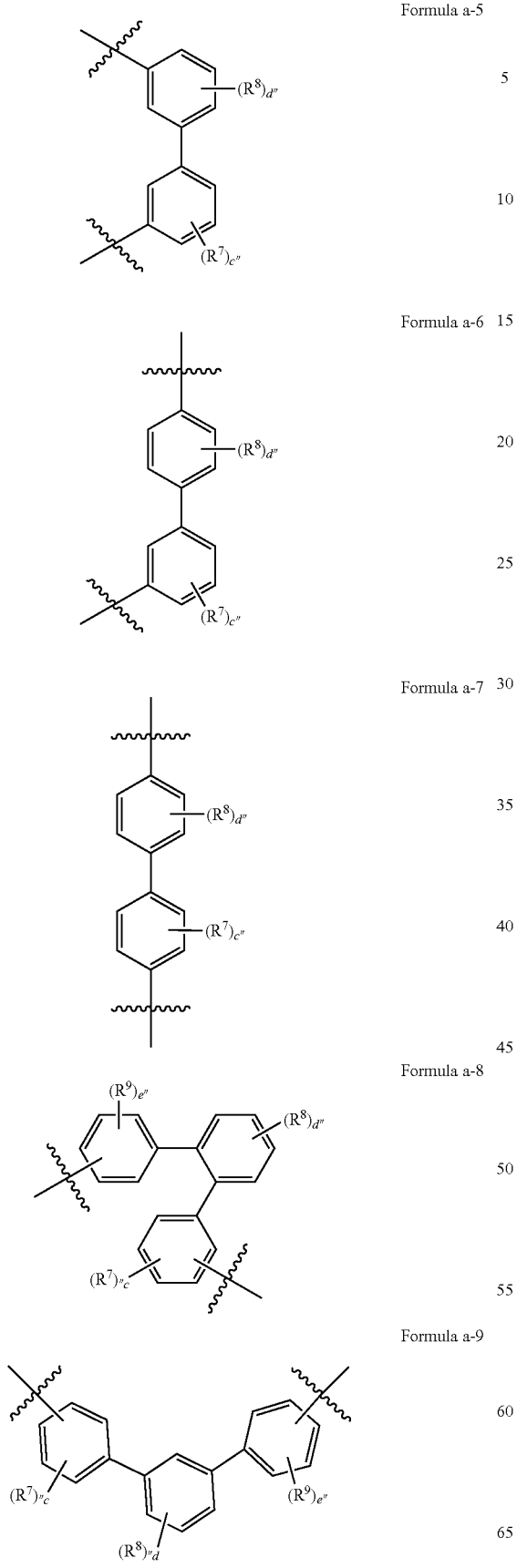

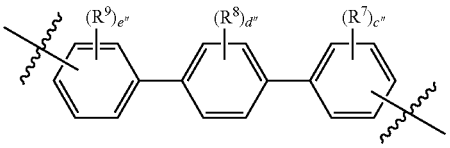

Formula a-10

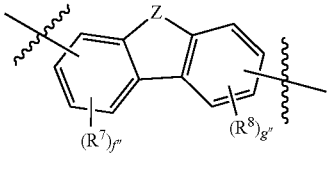

Formula a-11

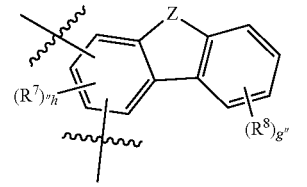

Formula a-12

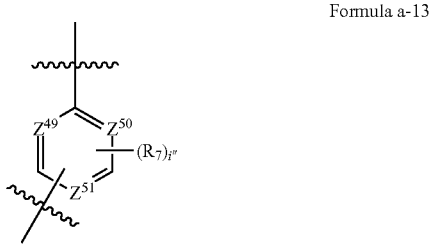

Formula a-13

The substituents of the Formulas a-1 to a-13 are as follows.

Z is O, S, $CR^dR^e$ or $NR^f$, and when Z is bonded to the Formula 1, it may be N or C.

$R^d$, $R^e$ and $R^f$ are each independently selected from the group consisting of hydrogen; deuterium; a $C_1$-$C_{50}$ alkyl group; a $C_2$-$C_{20}$ alkenyl group; a $C_6$-$C_{60}$ aryl group; fluorenyl group; a $C_2$-$C_{60}$ hetero ring group and a $C_3$-$C_{60}$ aliphatic ring and a $C_6$-$C_{60}$ aromatic ring fused ring group comprising at least one heteroatom of O, N, S, Si and P.

When $R^d$, $R^e$ and $R^f$ are an aryl group, for example, the aryl group is a $C_6$-$C_{60}$ aryl group, a $C_6$-$C_{40}$ aryl group, a $C_6$-$C_{25}$ aryl group, or a $C_6$-$C_{10}$ aryl group, and $R^d$, $R^e$ and $R^f$ may be the same as or different from each other.

When $R^d$, $R^e$ and $R^f$ are a hetero ring group, for example, the hetero ring group is a $C_2$-$C_{60}$ hetero ring group, a $C_2$-$C_{40}$ hetero ring group, or a $C_2$-$C_{20}$ hetero ring group and $R^d$, $R^e$ and $R^f$ may be the same as or different from each other.

a", c", d", and e" may be each independently an integer of 0 to 4, and b" may be an integer of 0 to 6.

f" and g" may be each independently be an integer of 0 to 3, h" may be an integer of 0 to 2, and i" may be an integer of 0 or 1.

$R^7$ to $R^9$ are each independently selected from the group consisting of deuterium; $C_6$-$C_{60}$ aryl group; fluorenyl group; a $C_2$-$C_{60}$ hetero ring group containing at least one heteroatom selected from the group consisting of O, N, S, Si and P, and may be bonded to form a ring.

When $R^7$ to $R^9$ is an aryl group, for example, the aryl group is a $C_6$-$C_{60}$ aryl group, a $C_6$-$C_{40}$ aryl group, a $C_6$-$C_{25}$ aryl group, or a $C_6$-$C_{10}$ aryl group, and $R^7$ to $R^9$ may be the same as or different from each other.

When $R^7$ to $R^9$ is a hetero ring group, for example, the hetero ring group is a $C_2$-$C_{60}$ hetero ring group, a $C_2$-$C_{40}$ hetero ring group, or a $C_2$-$C_{20}$ hetero ring group and $R^7$ to $R^9$ may be the same as or different from each other.

$Z^{49}$, $Z^{50}$, and $Z^{51}$ may each independently be CR' or N, and at least one of $Z^{49}$, $Z^{50}$, and $Z^{51}$ may be N.

R' is each independently selected from the group consisting of hydrogen; deuterium; $C_6$-$C_{60}$ aryl group; fluorenyl group; a $C_2$-$C_{60}$ hetero ring group comprising at least one heteroatom selected from the group consisting of O, N, S, Si and P, and may be bonded to form a ring.

When R' is an aryl group, for example, R' may be a $C_6$-$C_{60}$ aryl group, a $C_6$-$C_{40}$ aryl group, a $C_6$-$C_{25}$ aryl group, or a $C_6$-$C_{10}$ aryl group, and R' may be the same as or different from each other.

When R' is a hetero ring group, for example, R' may be a $C_2$-$C_{60}$ hetero ring group, a $C_2$-$C_{40}$ hetero ring group, or a $C_2$-$C_{20}$ hetero ring group, and R' may be the same as or different from each other.

The compound represented by the Formula 1 is represented by one of following Formulas 1-A to 1-T.

Formula 1-A

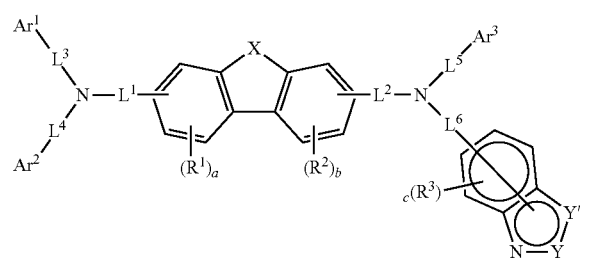

Formula 1-B

Formula 1-C

Formula 1-D

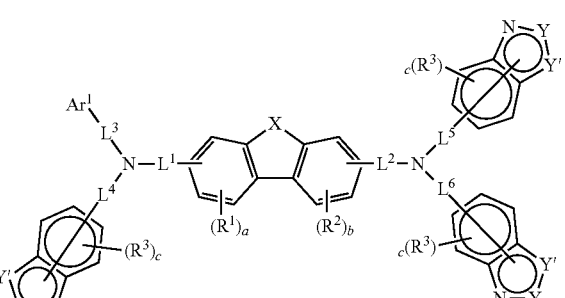

Formula 1-E

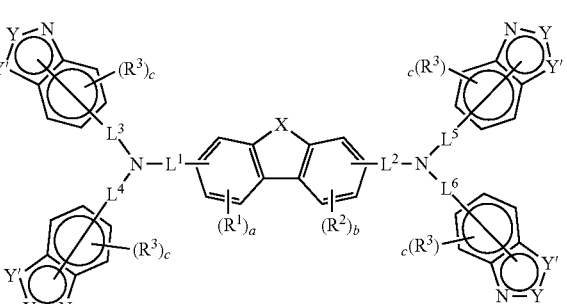

Formula 1-F

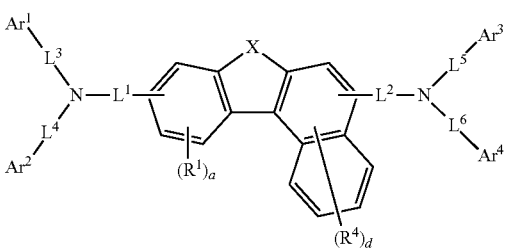

Formula 1-G

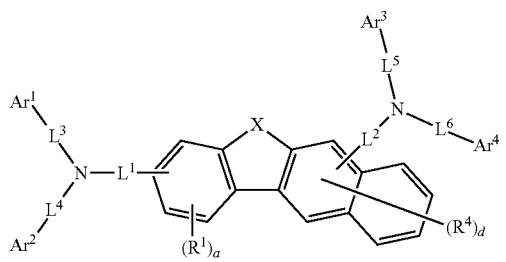

Formula 1-H

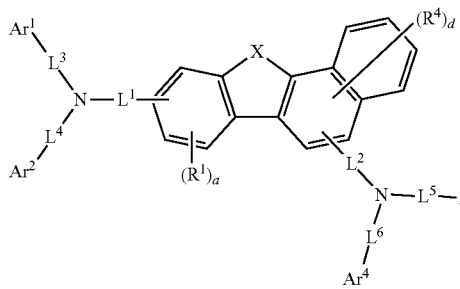

Formula 1-I
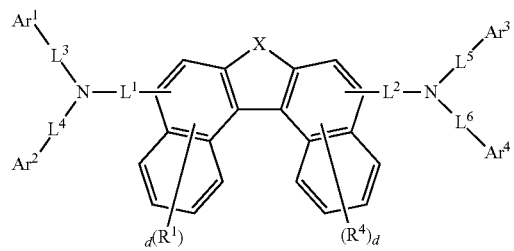
Formula 1-J
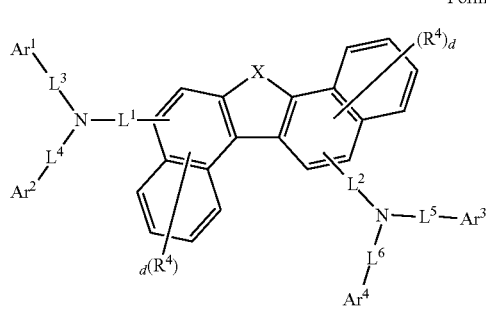
Formula 1-K
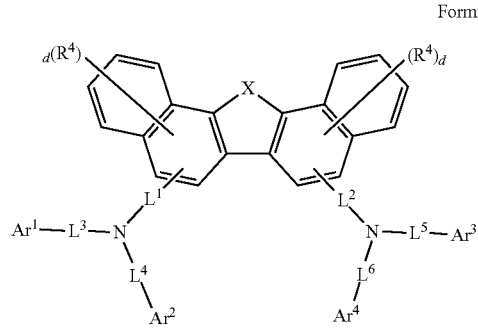
Formula 1-L
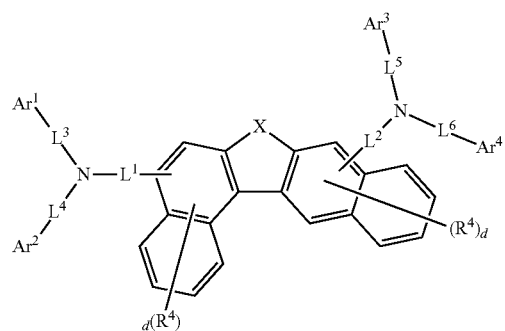
Formula 1-M
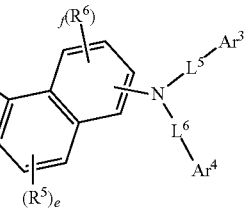
Formula 1-N
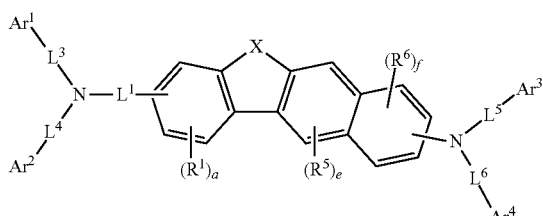
Formula 1-O
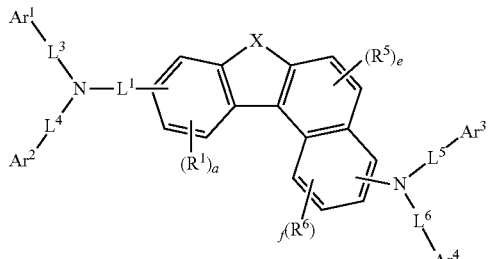
Formula 1-P
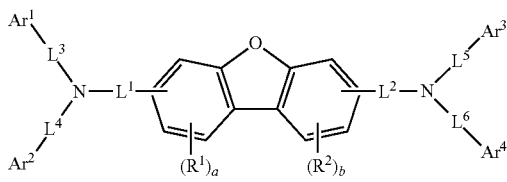
Formula 1-Q
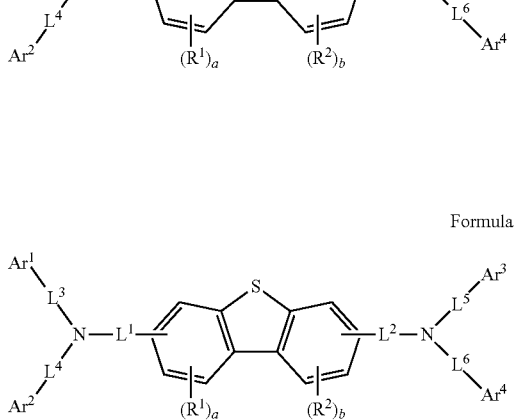

-continued

Formula 1-R

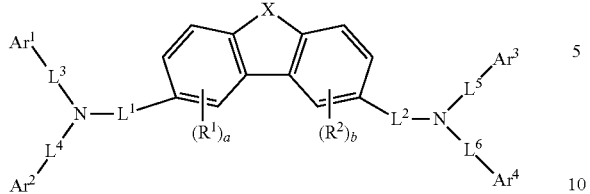

Formula 1-S

Formula 1-T

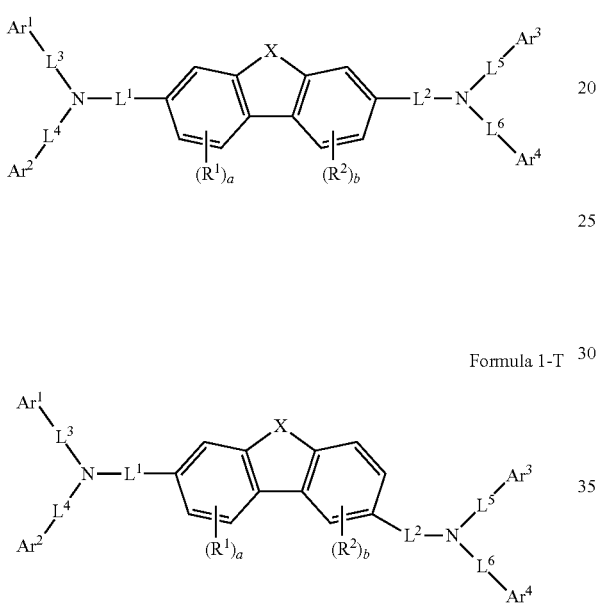

where $Ar^1$ to $Ar^4$, $R^1$ to $R^3$, L $L^6$, a, b, c, X, and in the Formulas 1-A to 1-T are the same as defined in the Formula 1, and $R^4$ to $R^6$ are the same as $R^1$ as defined in the Formula, d is an integer from 0 to 5, e is an integer from 0 to 2, f is an integer from 0 to 3, and a plurality of d's, e's f's are the same as or different from each other.

At least one of $Ar^1$ to $Ar^4$ may be represented by the following Formulas 1-1a to 1-e.

Formula 1-1a
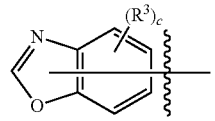

Formula 1-1b
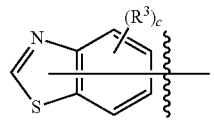

Formula 1-1c
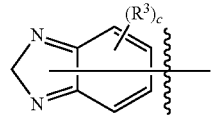

Formula 1-1d
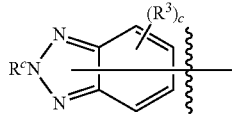

Formula 1-1e
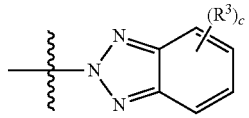

In the Formulas 1-1a to 1-1e, $R^3$ and c are the same as defined in Formula 1.

The compound represented by the Formula 1 comprises one of following compounds, but it is not limited thereto.

P-1
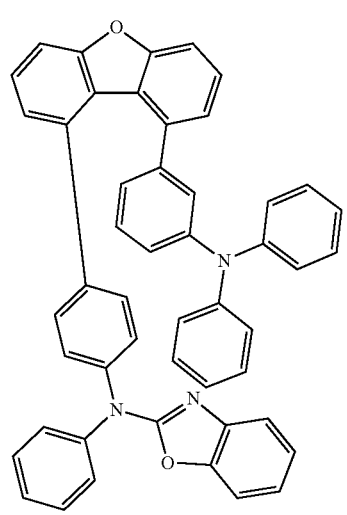

P-2
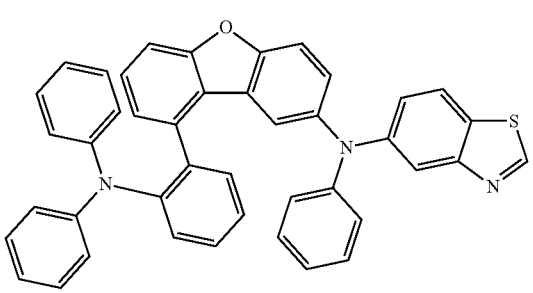

-continued
P-3
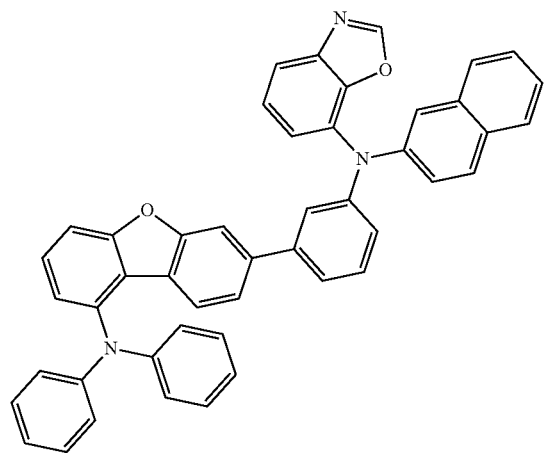
P-4
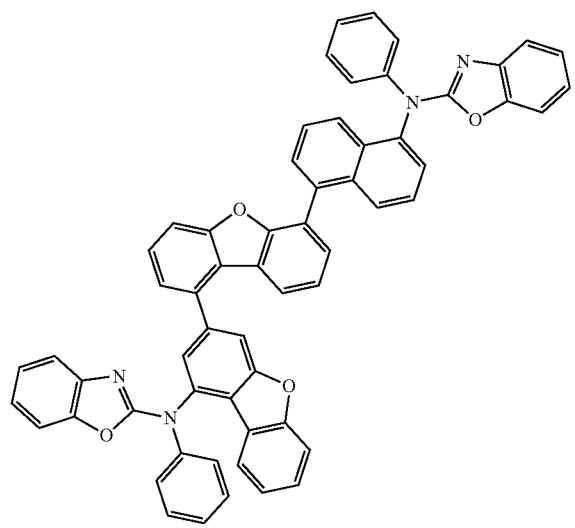
P-5
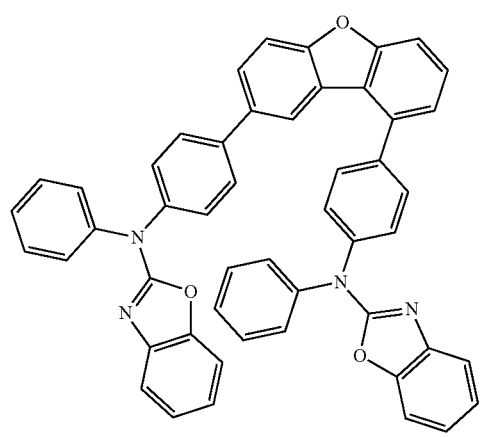
P-6
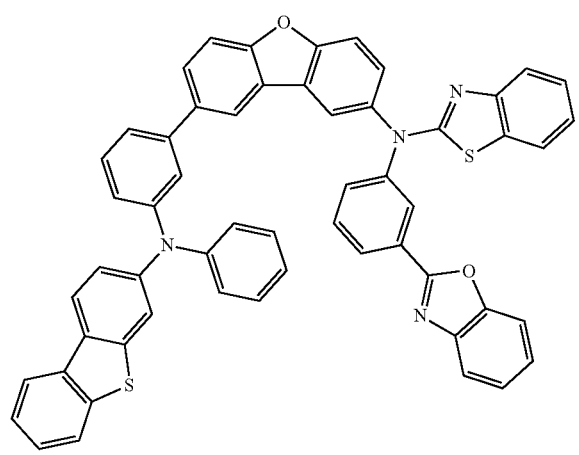
P-7
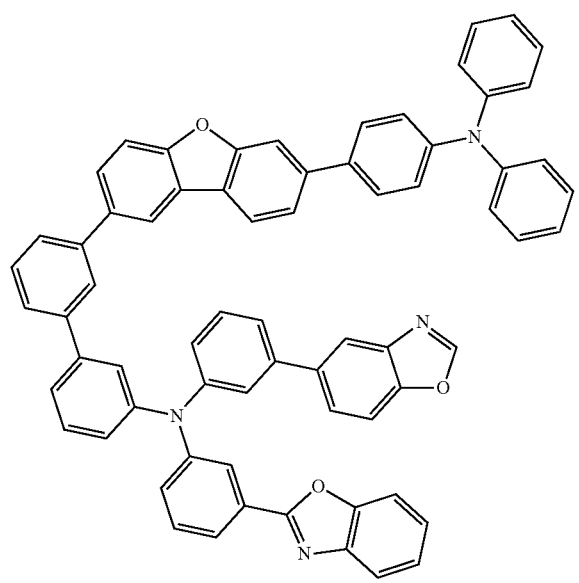
P-8
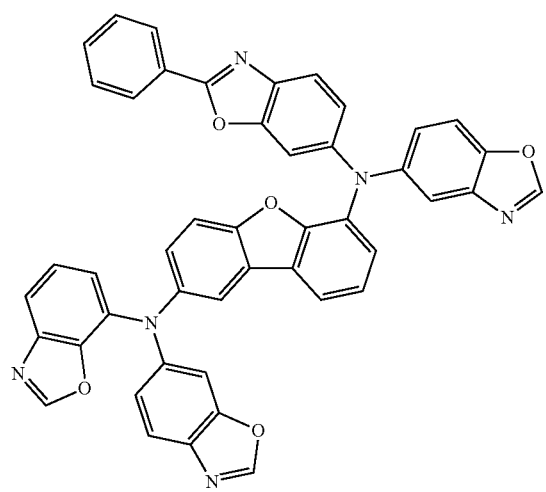

-continued
P-9
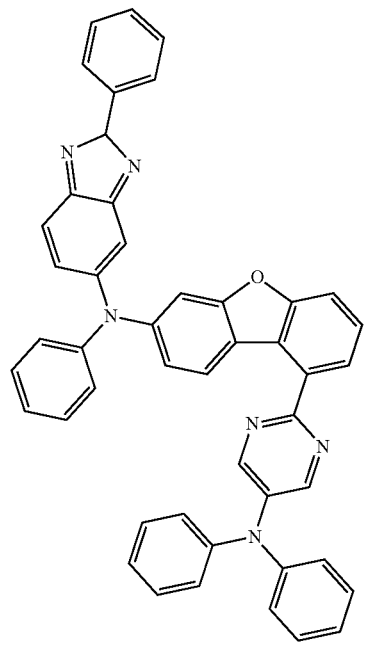
P-10
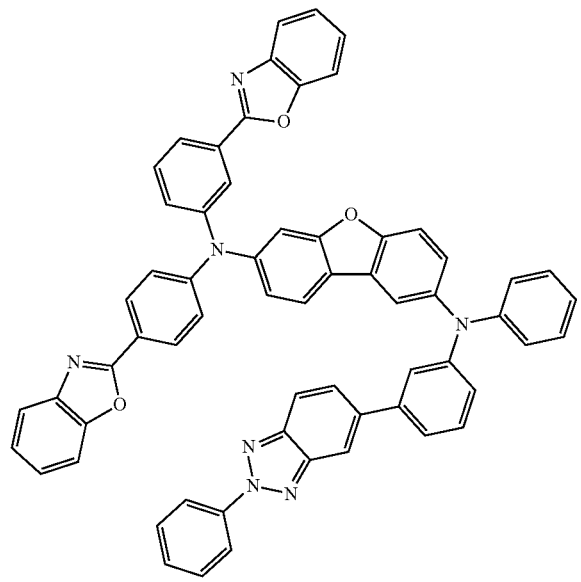
P-11
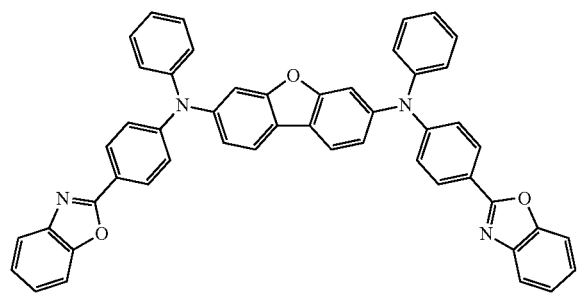
P-12
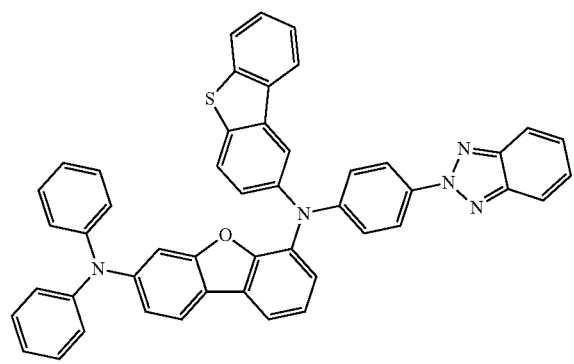
P-13
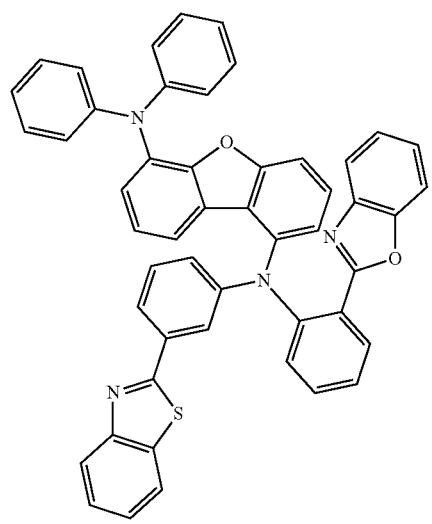
P-14
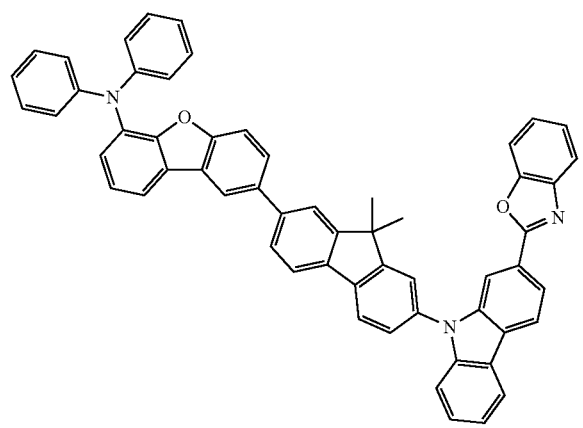

-continued
P-15
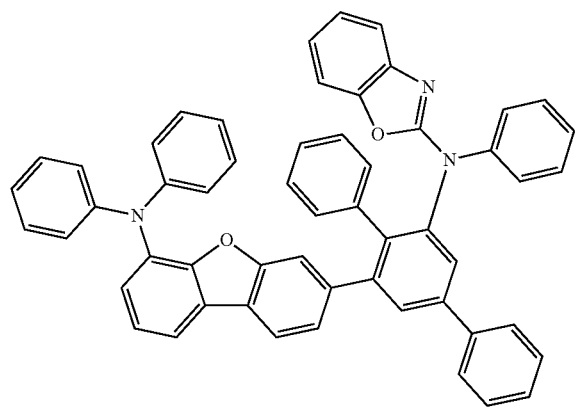
P-16
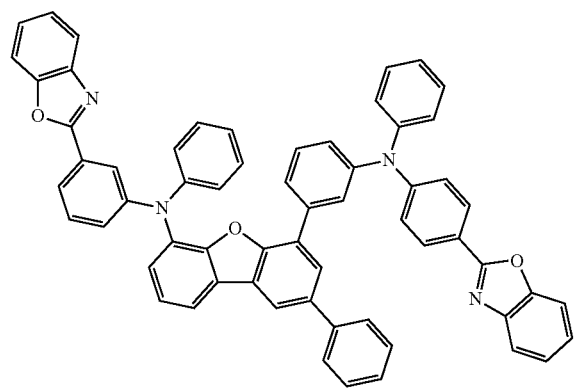
P-17
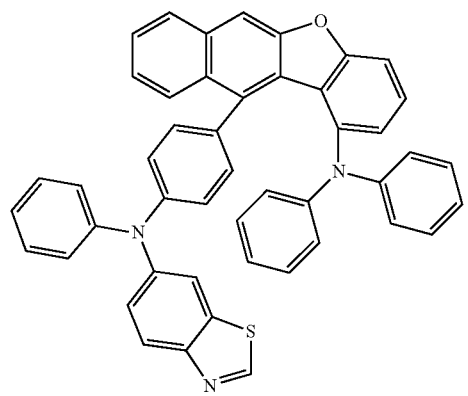
P-18
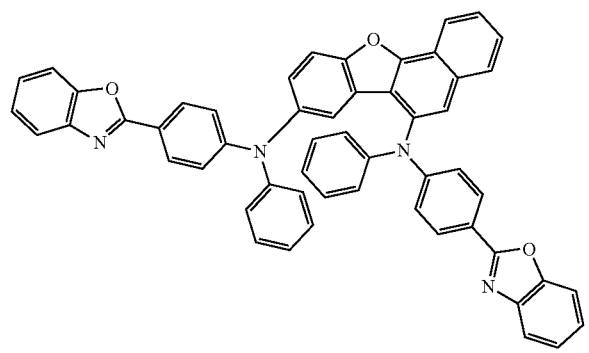
P-19
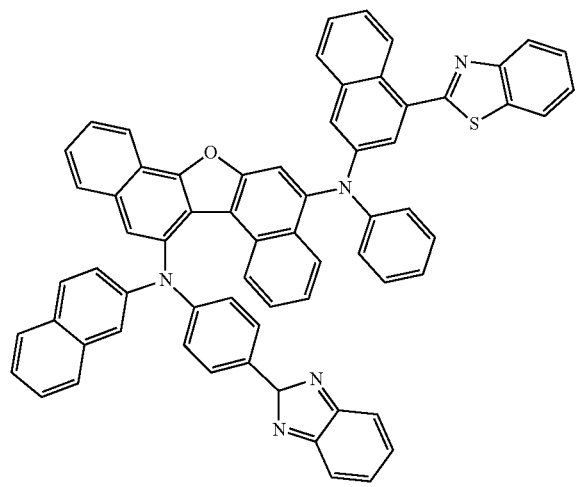
P-20
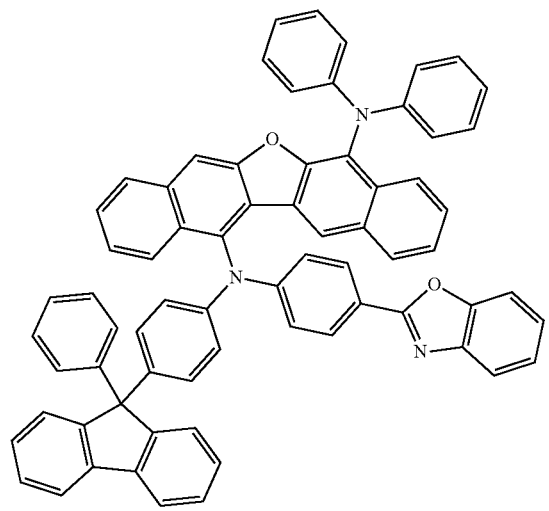

-continued
P-21
P-22
P-23
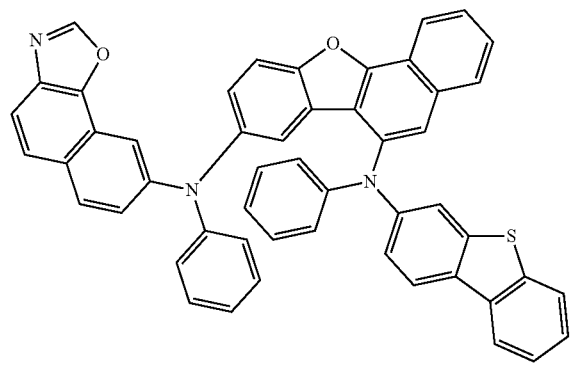

-continued
P-24
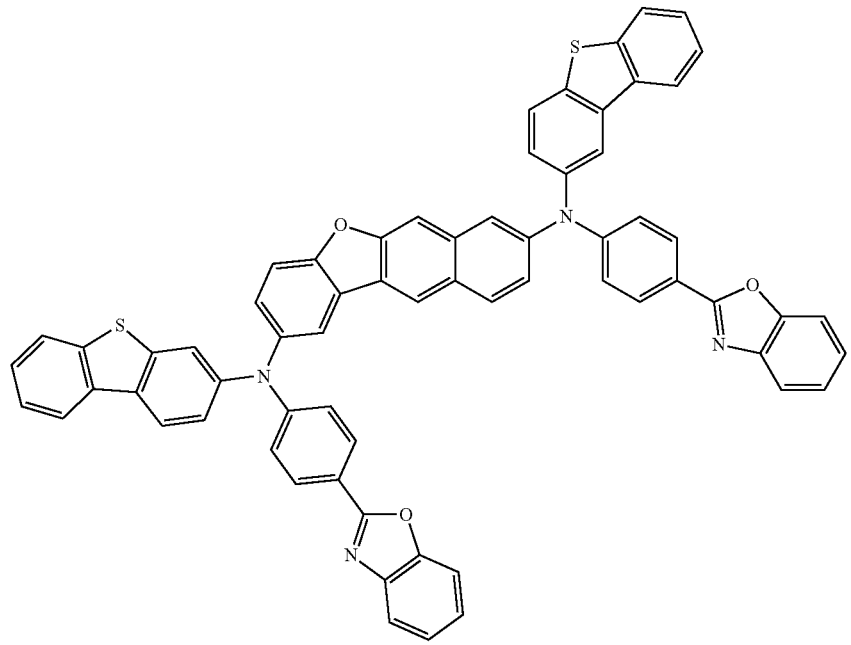
P-25
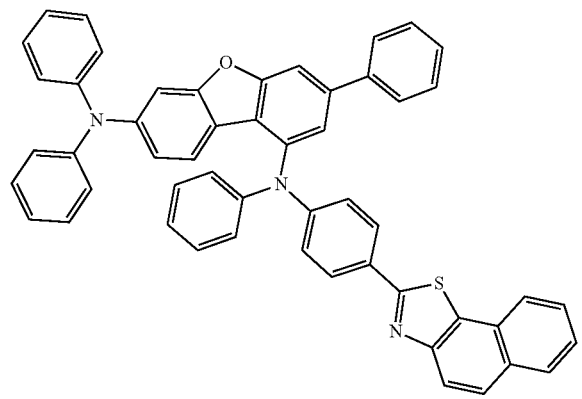
P-26
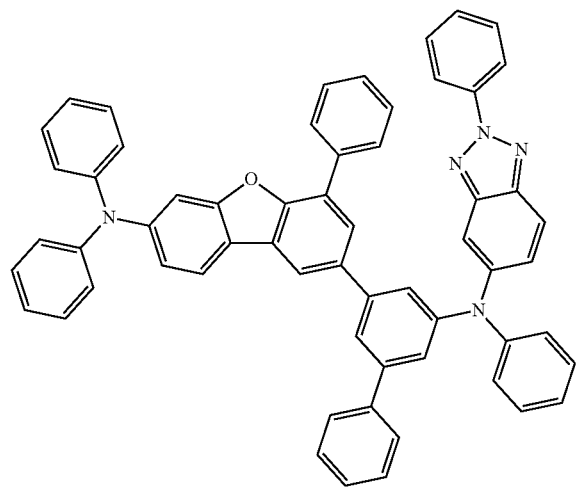
P-27
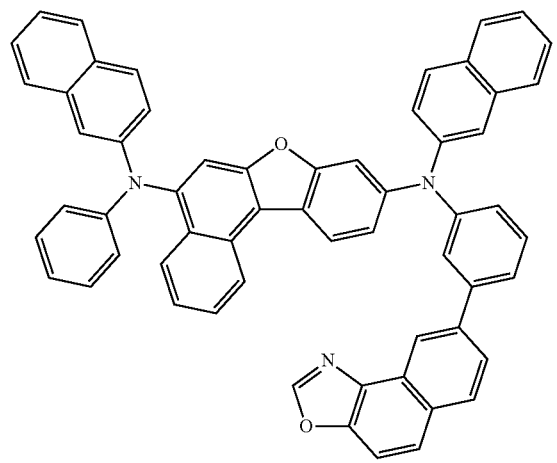
P-28
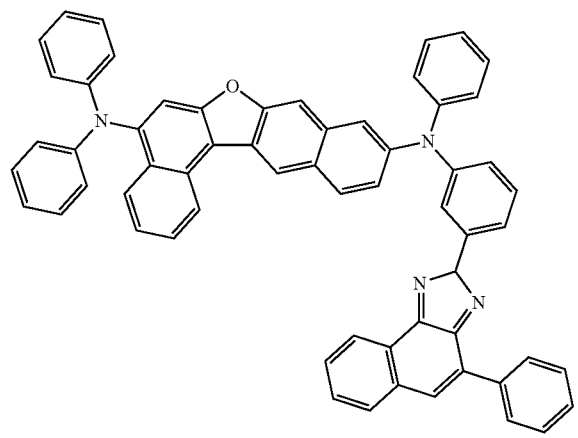

-continued
P-29
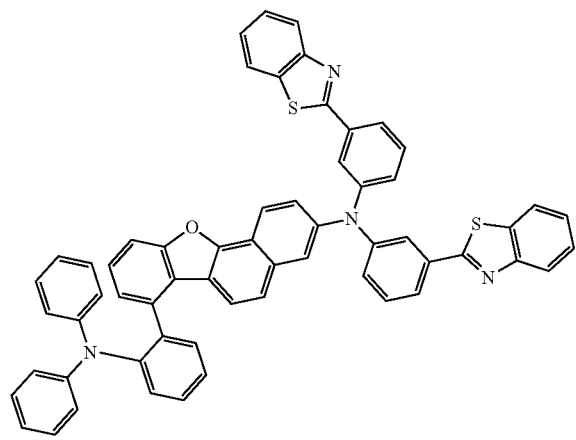
P-30
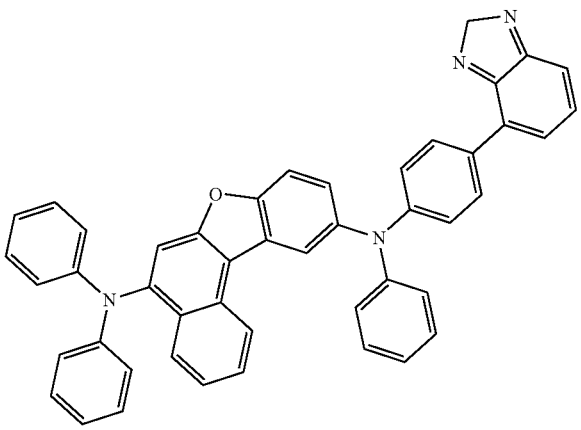
P-31
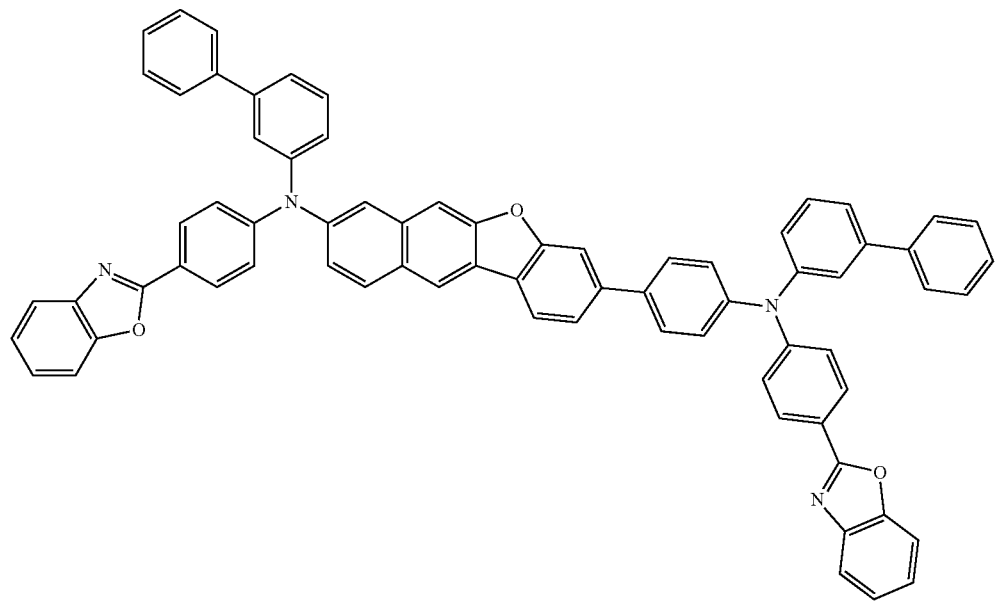
P-32
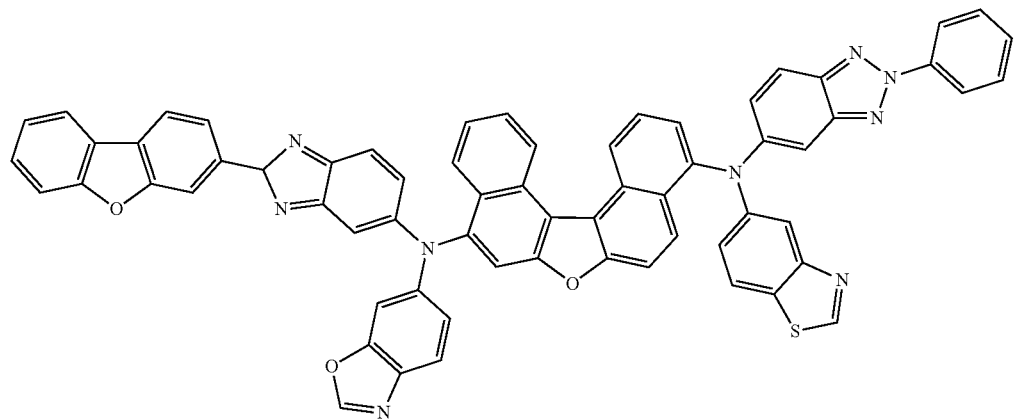

-continued
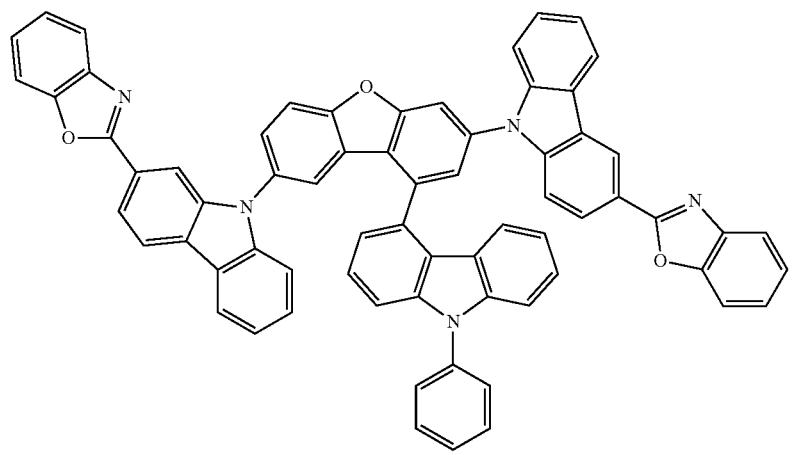
P-33
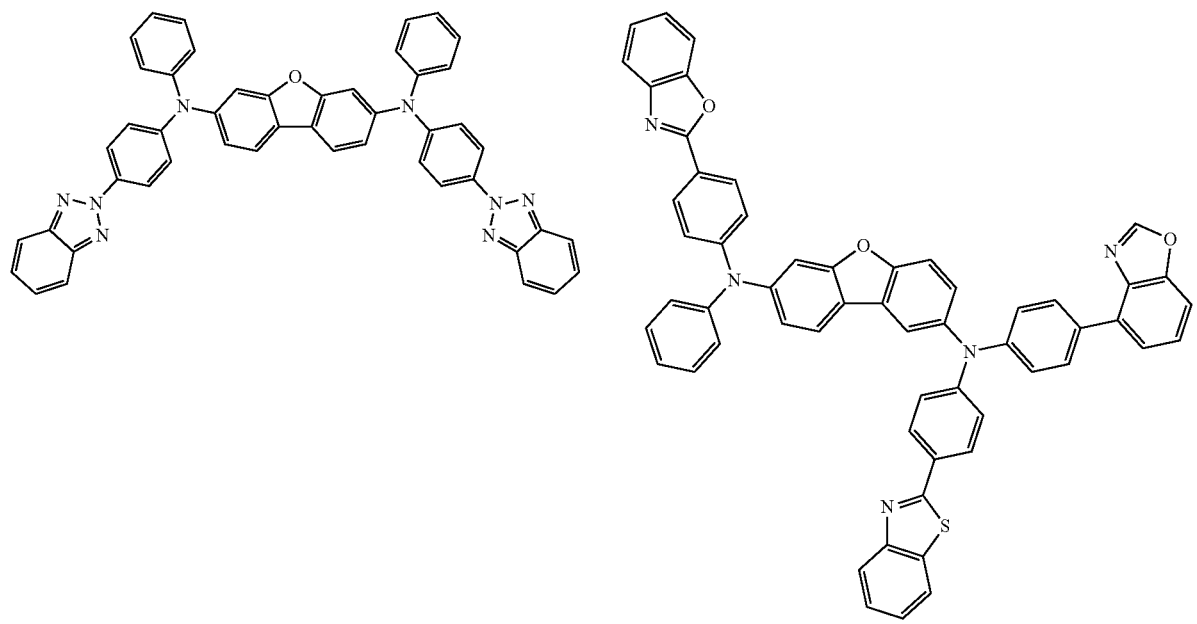
P-34
P-35
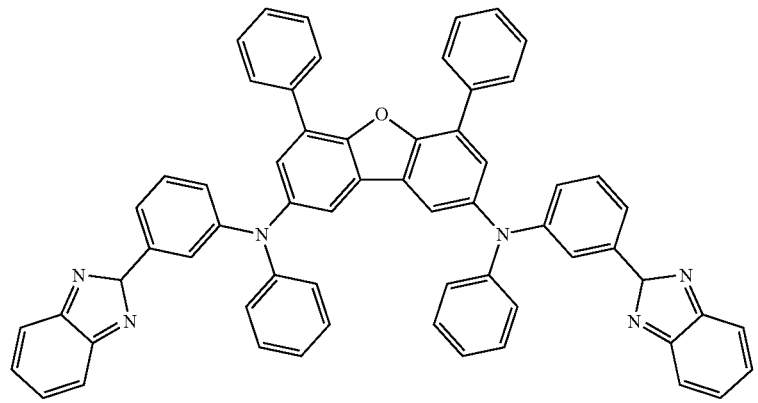
P-36

-continued
P-37
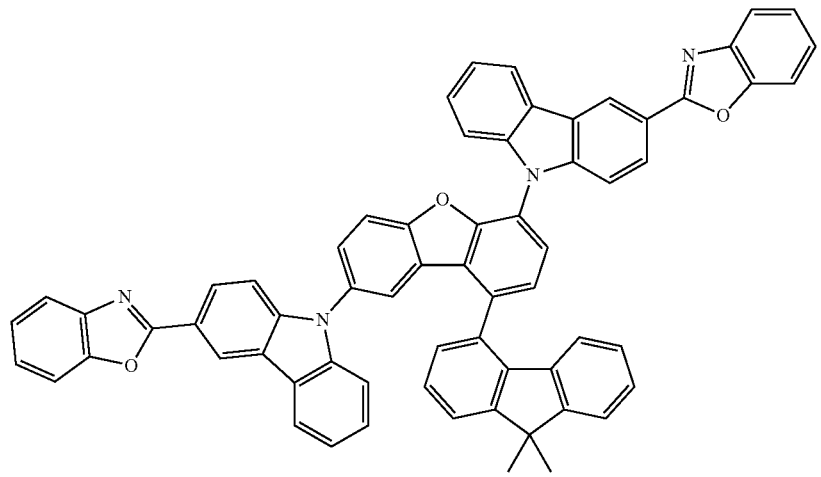
P-38
P-39
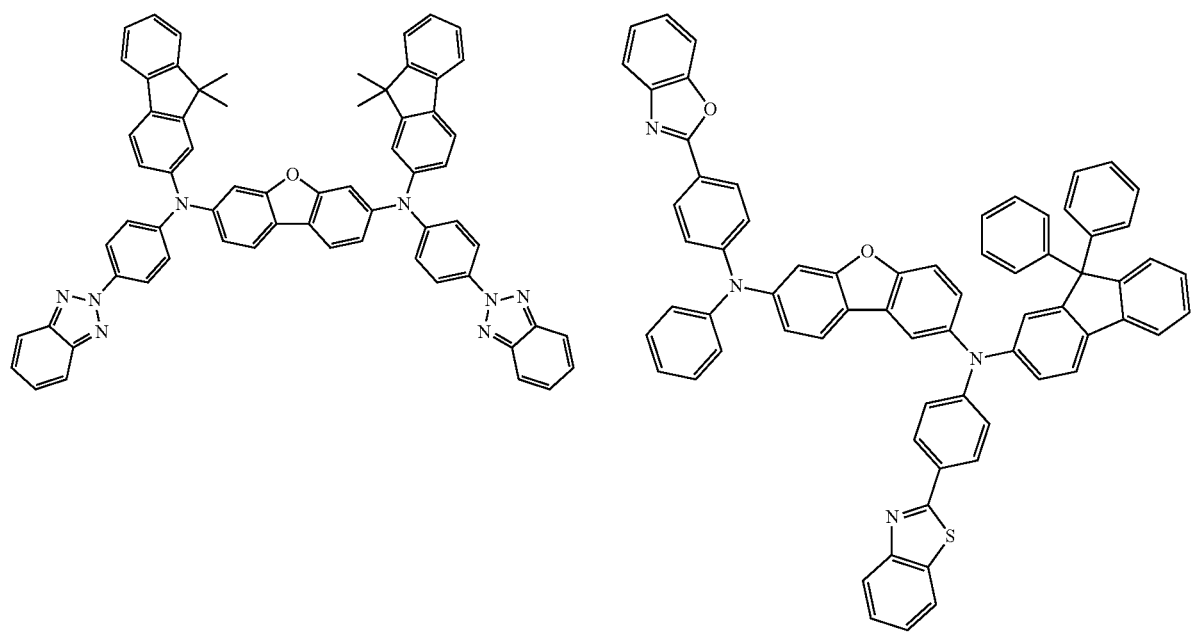
P-40
P-41
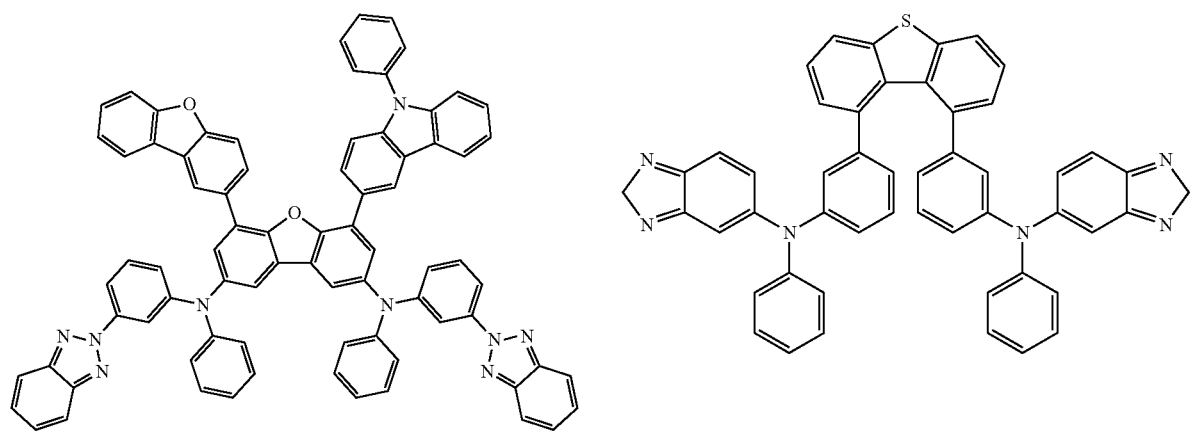

-continued
P-42
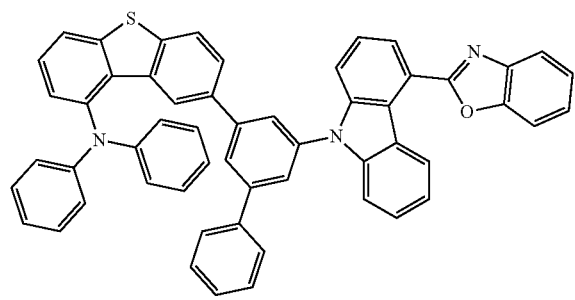
P-43
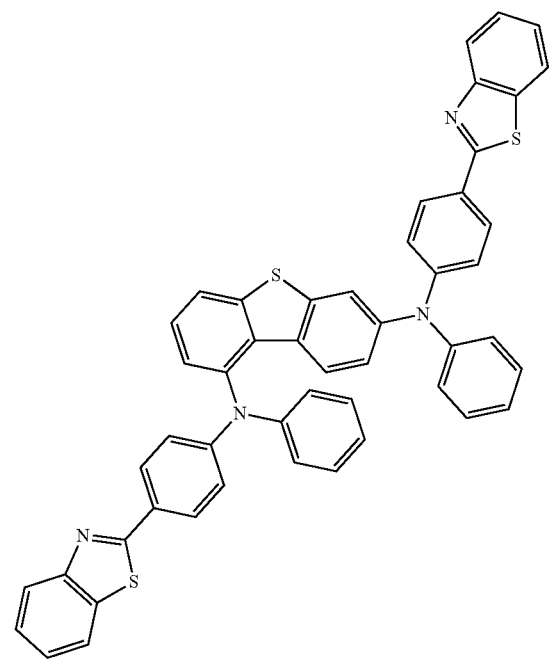
P-44
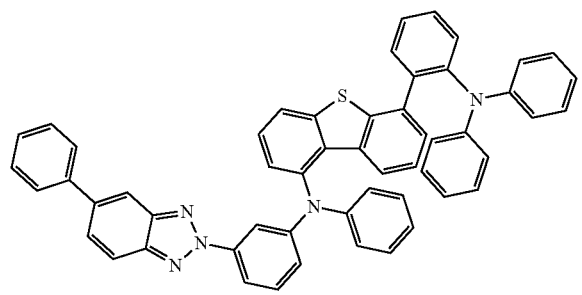
P-45
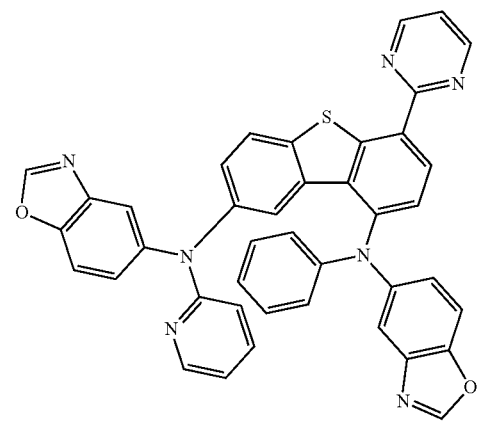
P-46
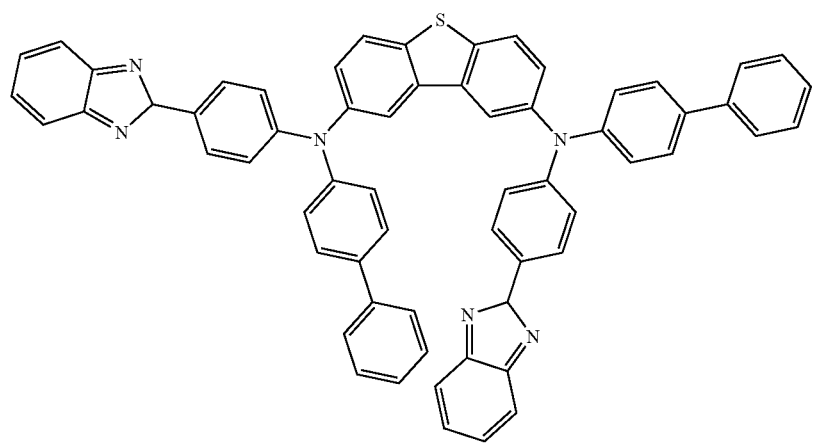

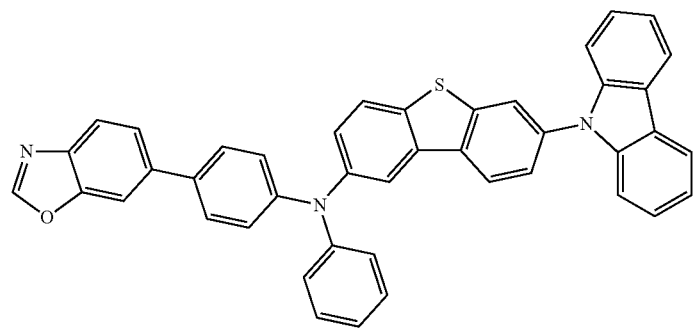
P-47
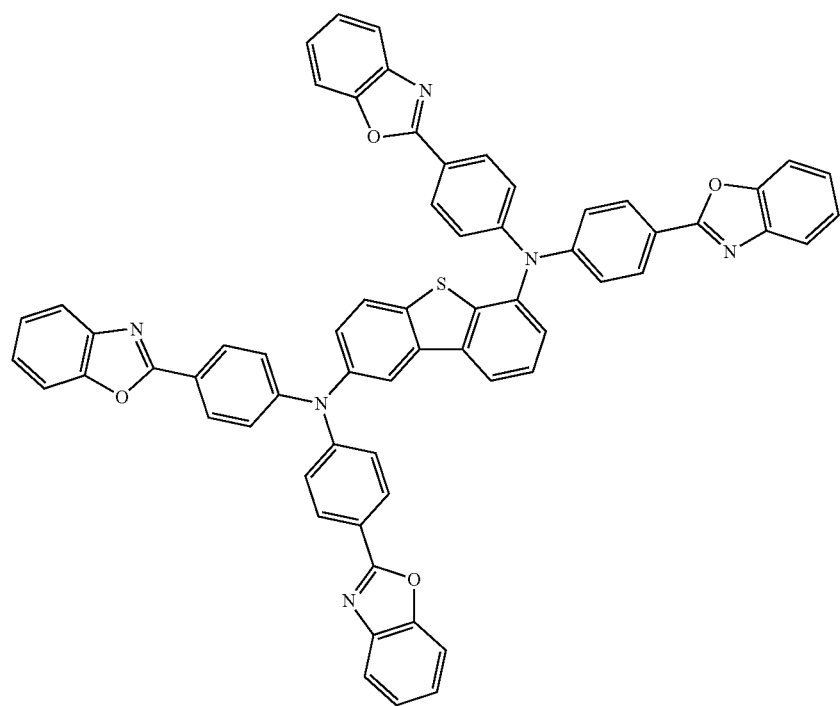
P-48
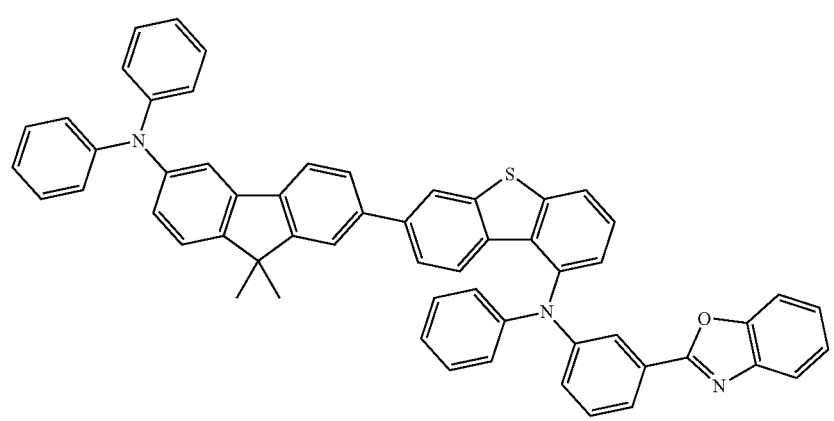
P-49

-continued
P-50
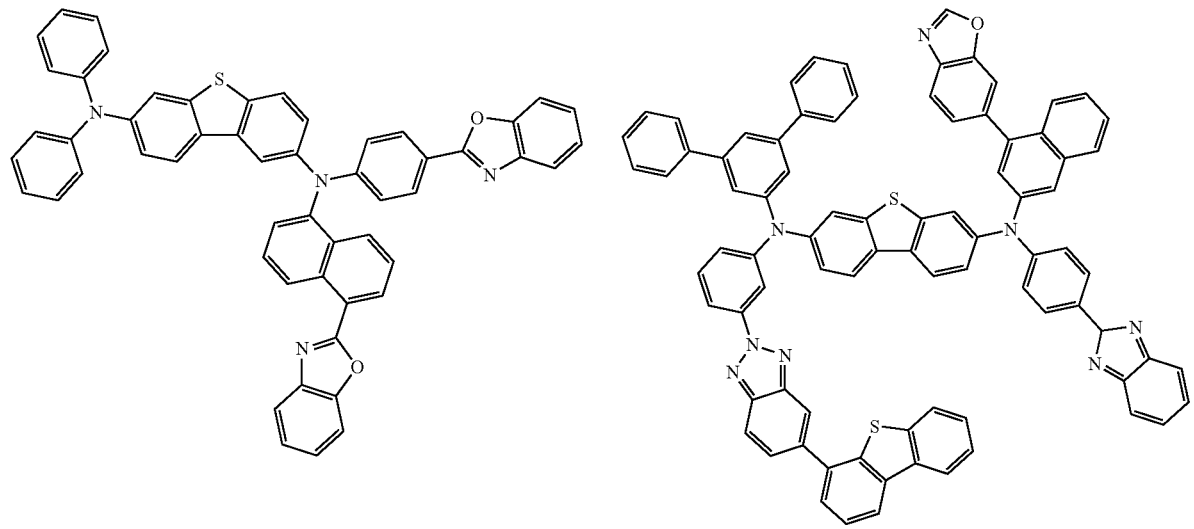
P-51
P-52
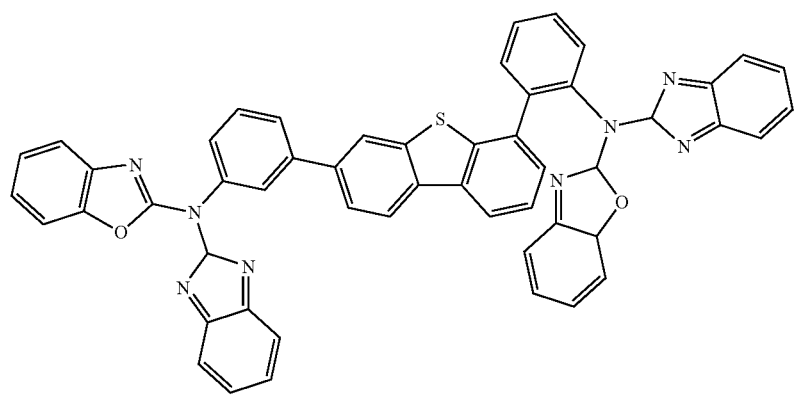
P-53
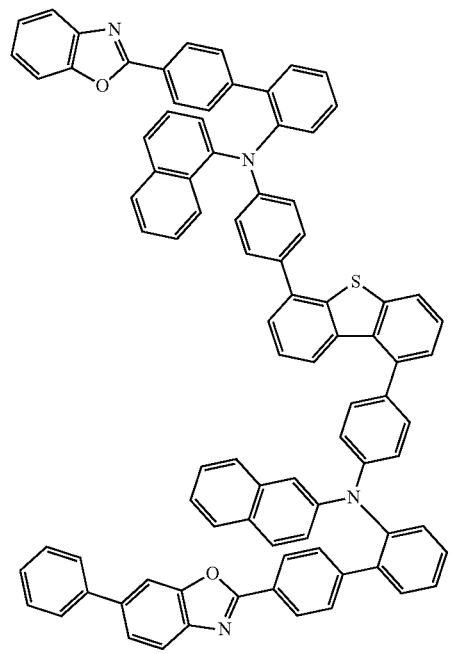
P-54
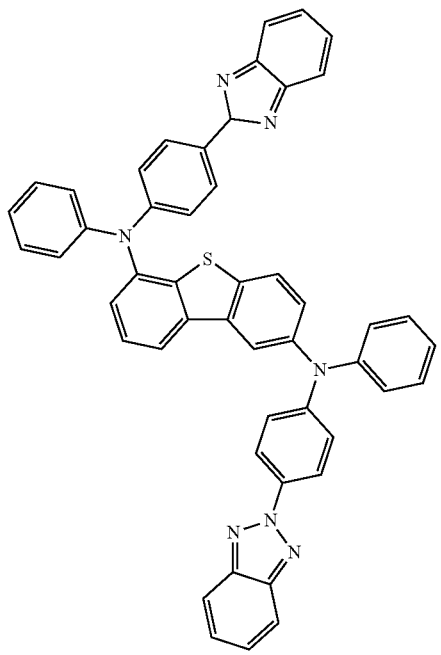

-continued
P-55
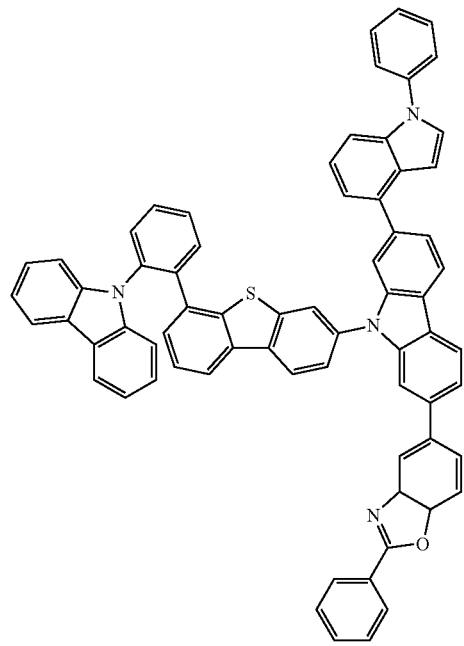
P-56
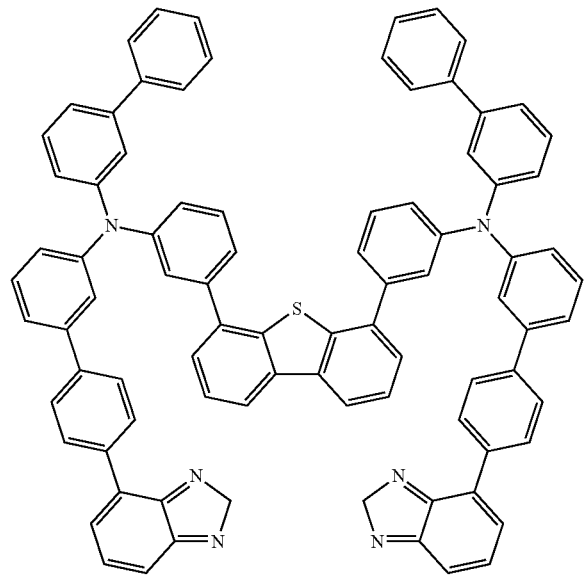
P-57
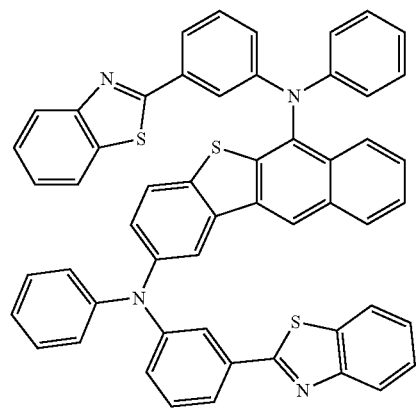
P-58
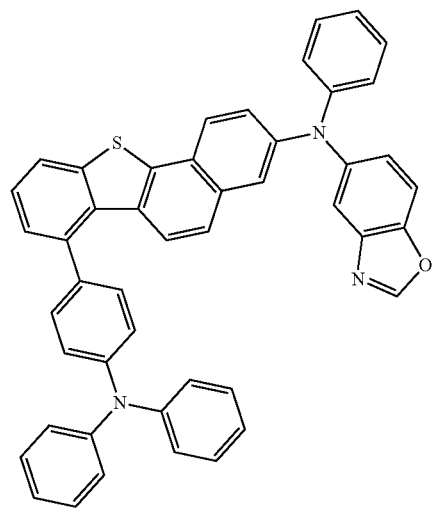
P-59
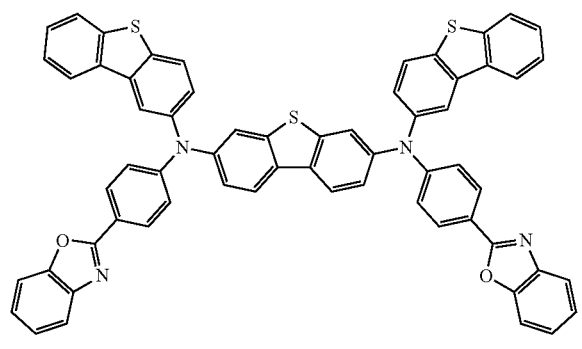
P-60
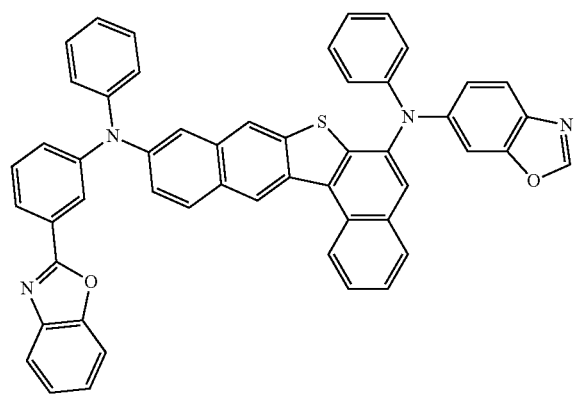

P-61
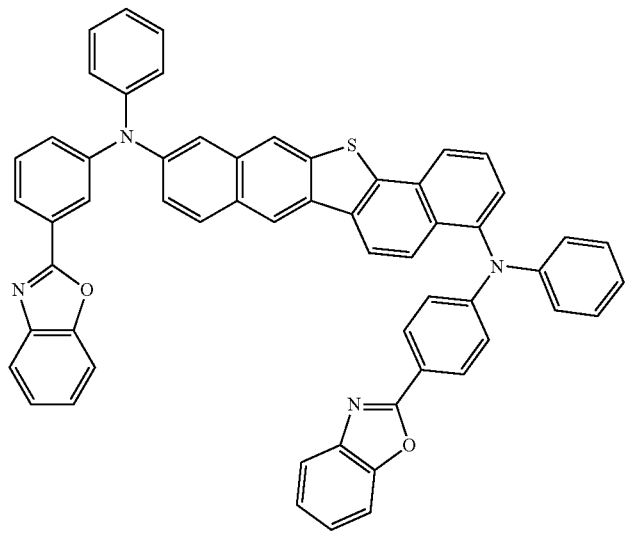
P-62
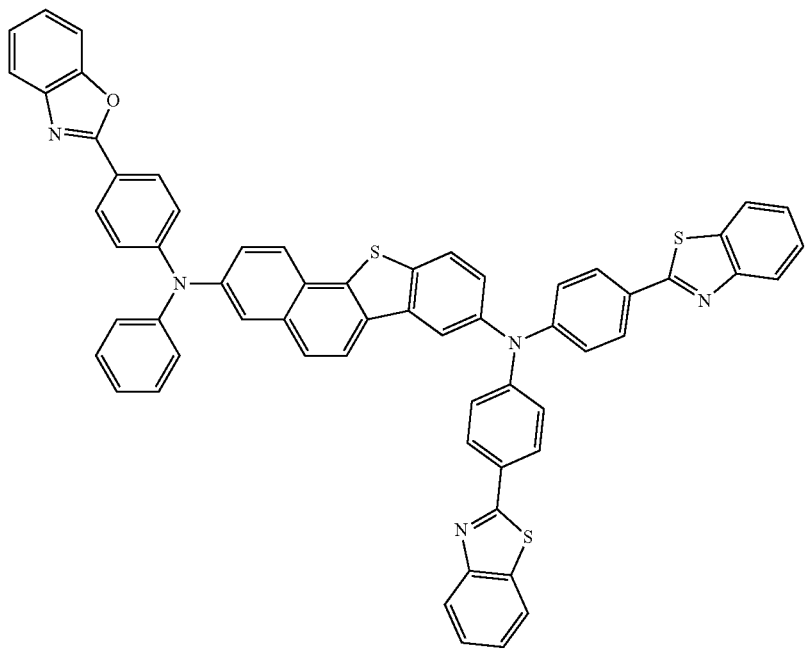
P-63 P-64
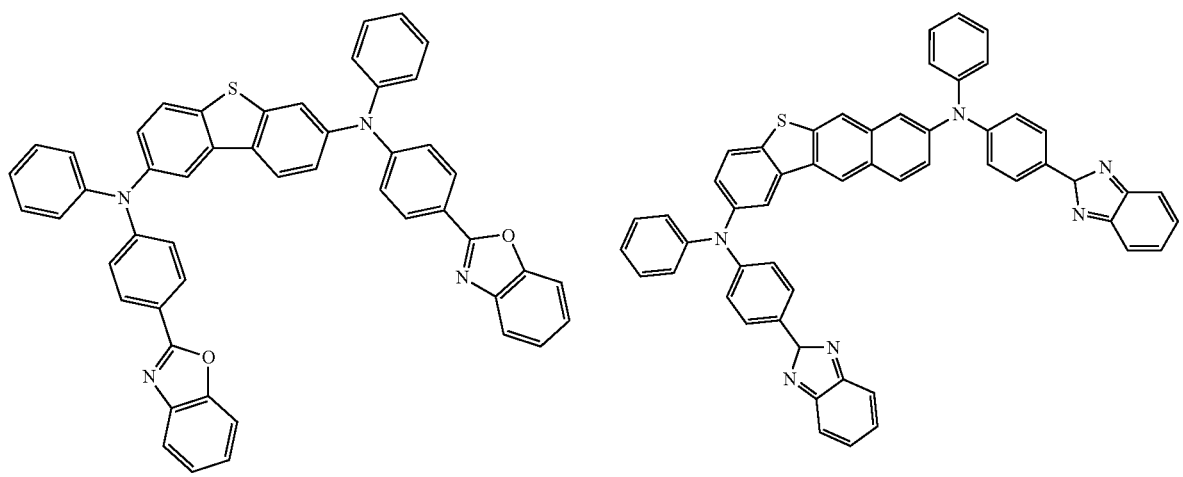

-continued
P-65
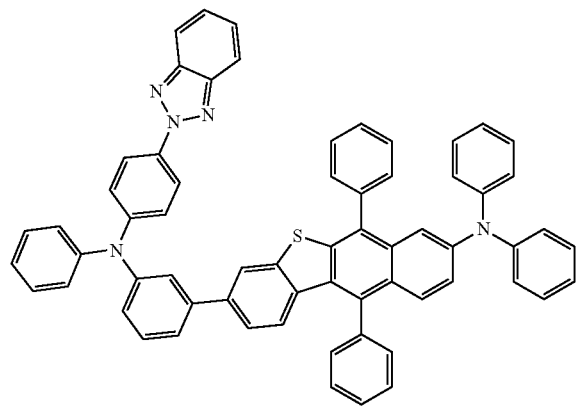
P-66
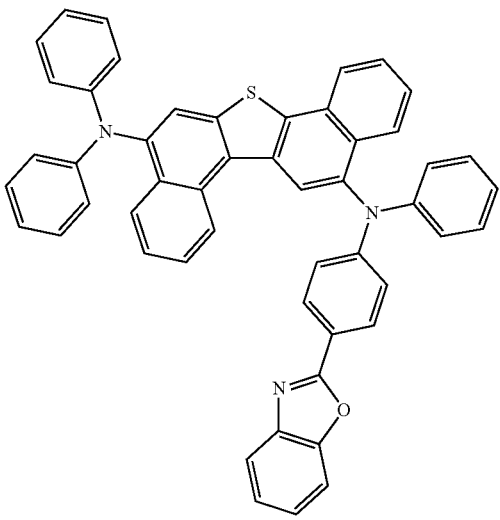
P-67
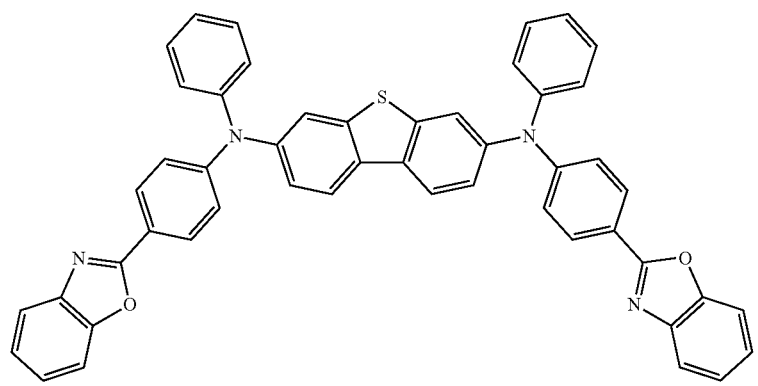
P-68
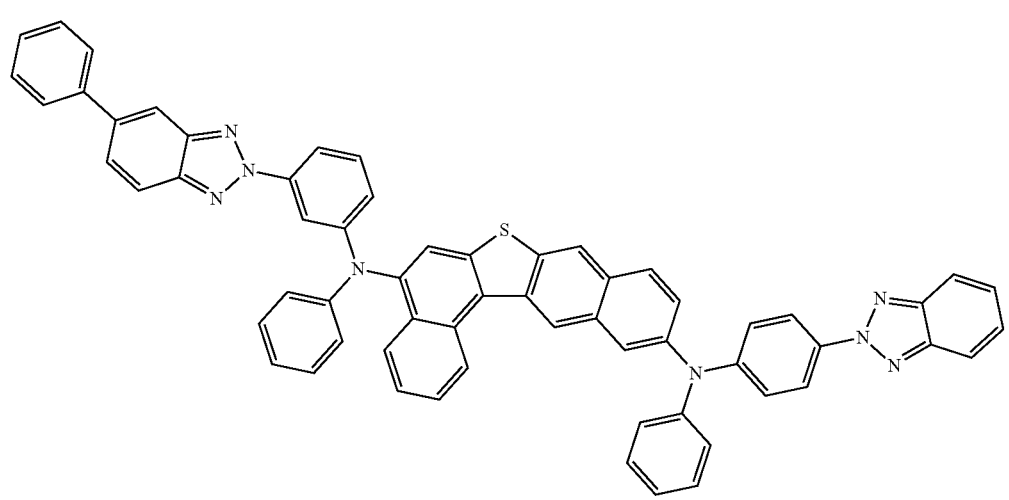

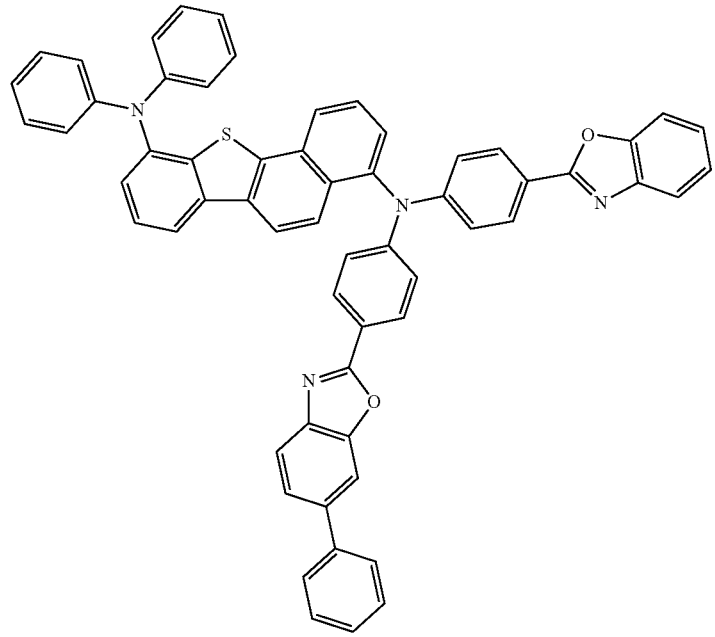
P-69
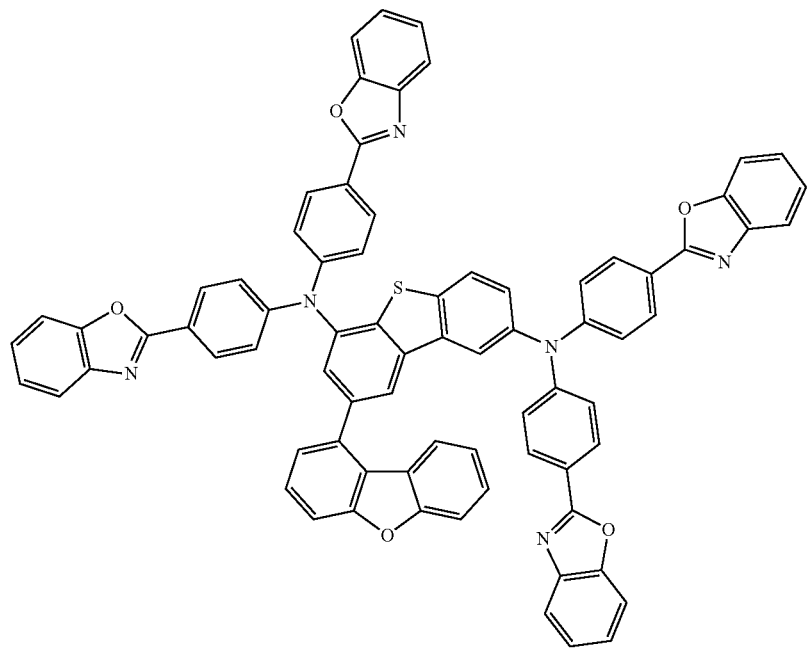
P-70

-continued
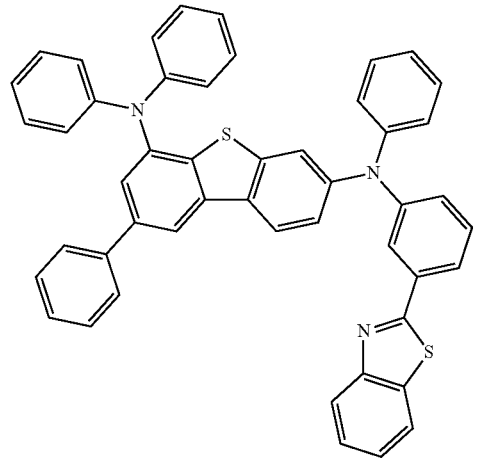
P-71
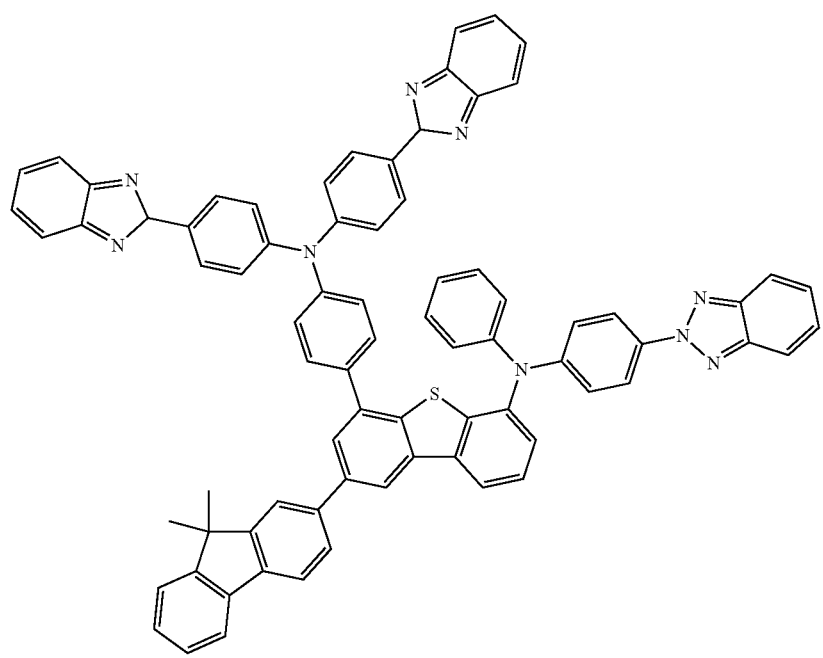
P-72

P-73
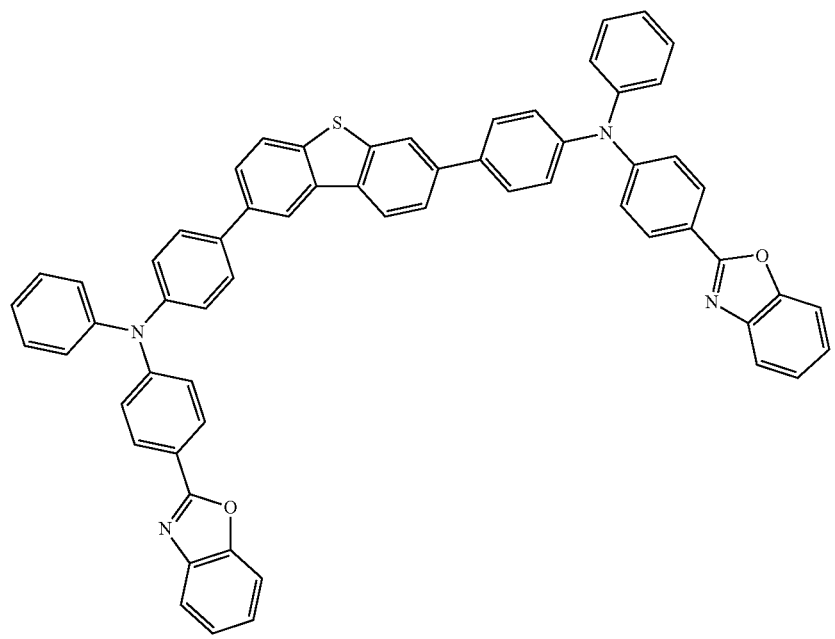
P-74
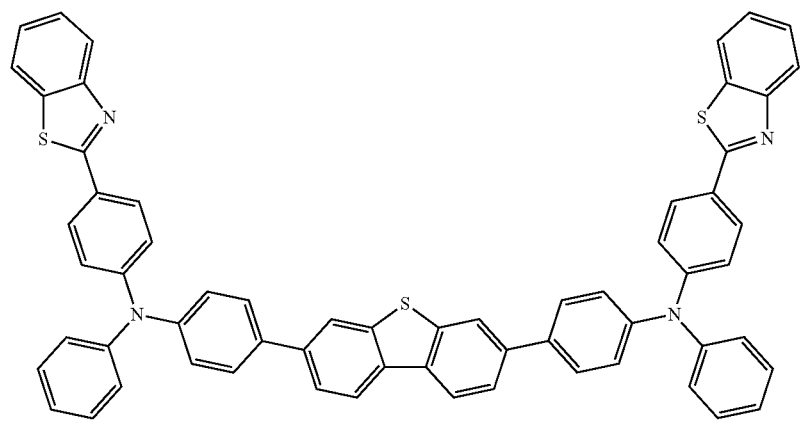
P-75
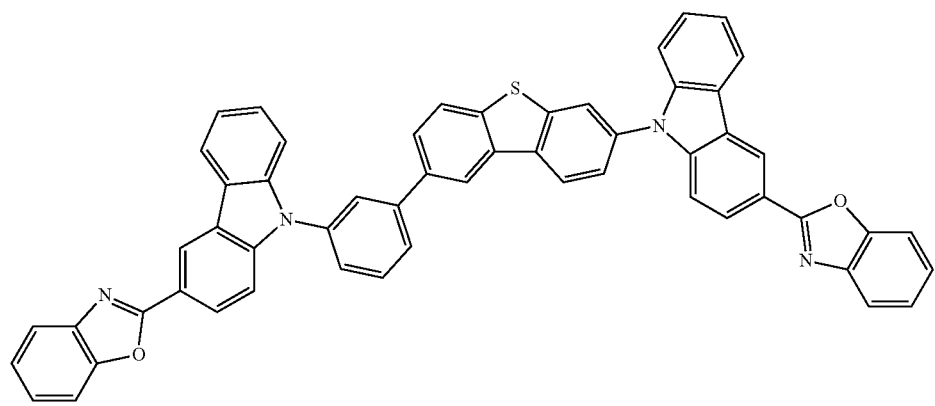

-continued
P-76
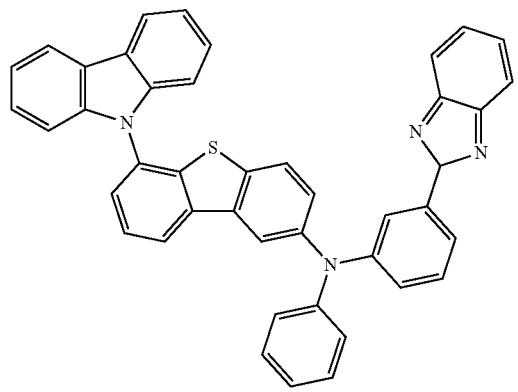
P-77
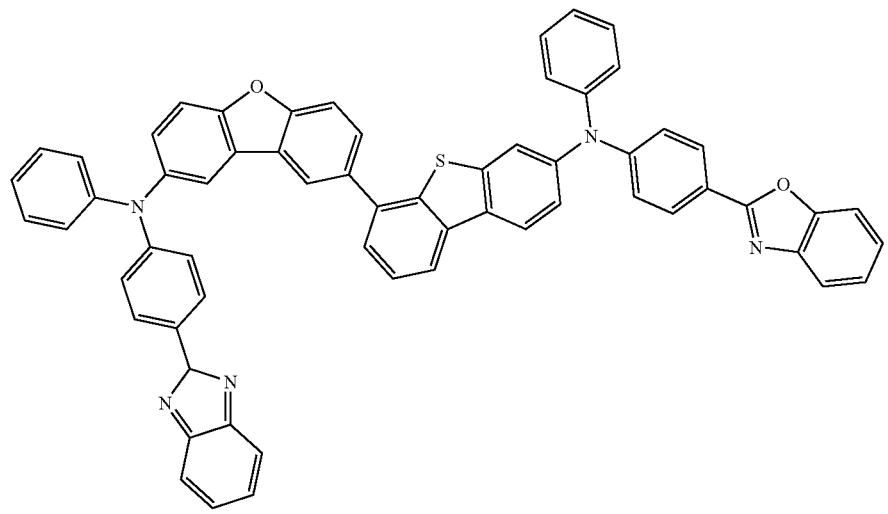
P-78
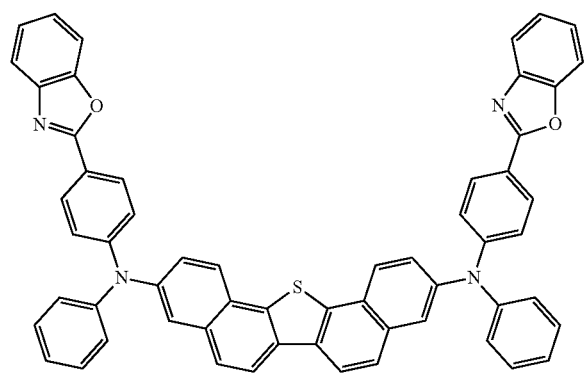
P-79
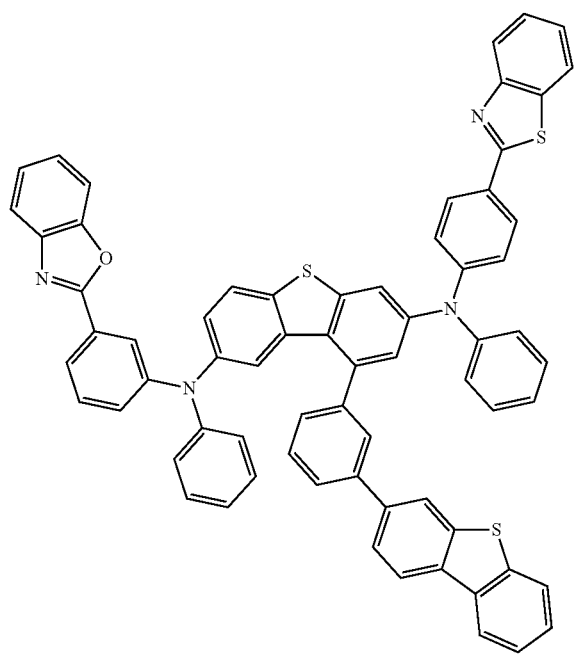

-continued
P-80
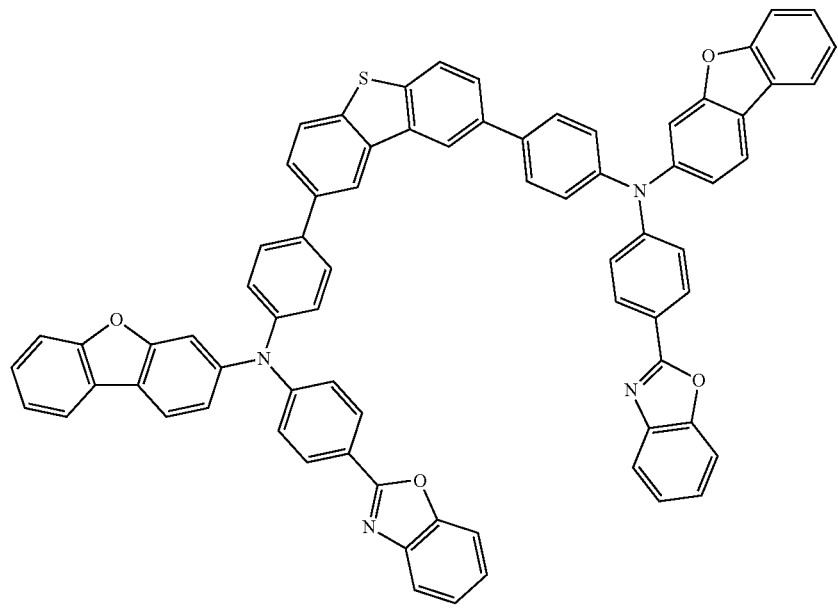
P-81
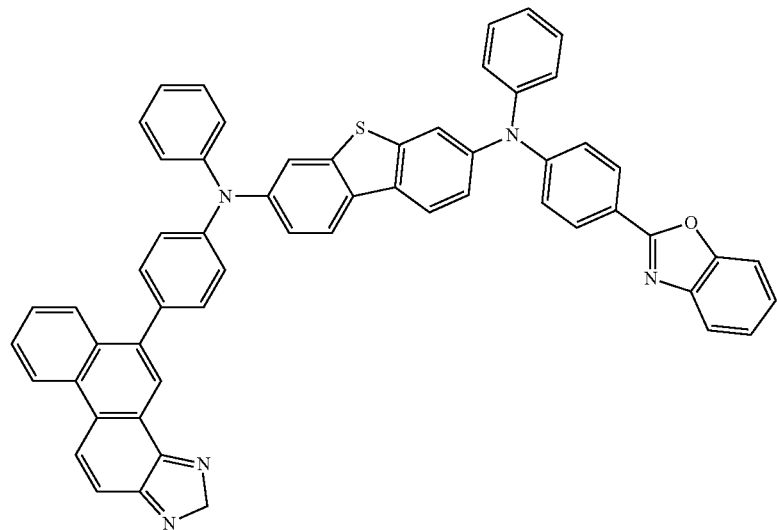
P-82
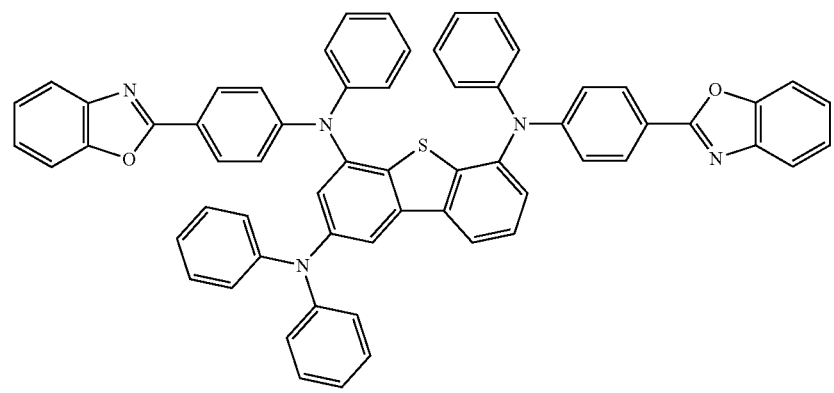

P-83
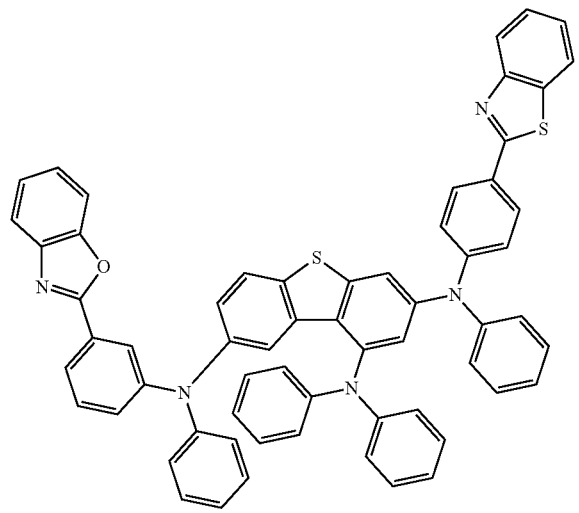
P-84
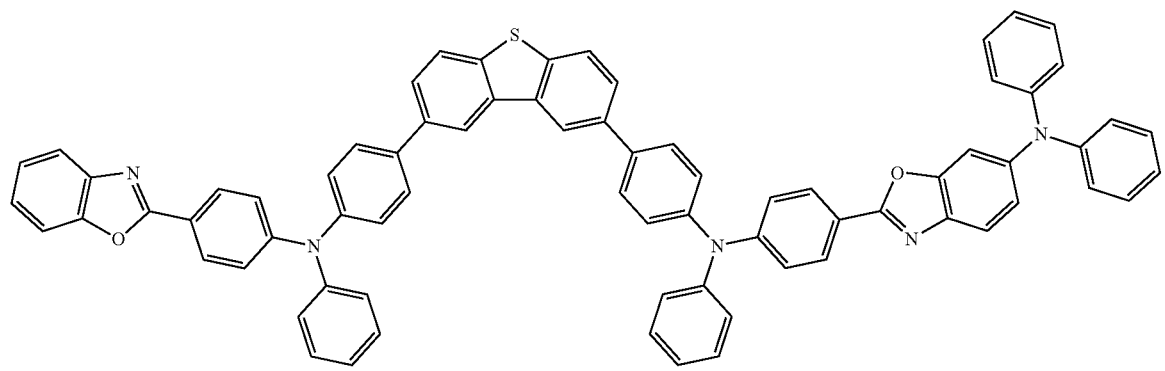
P-85
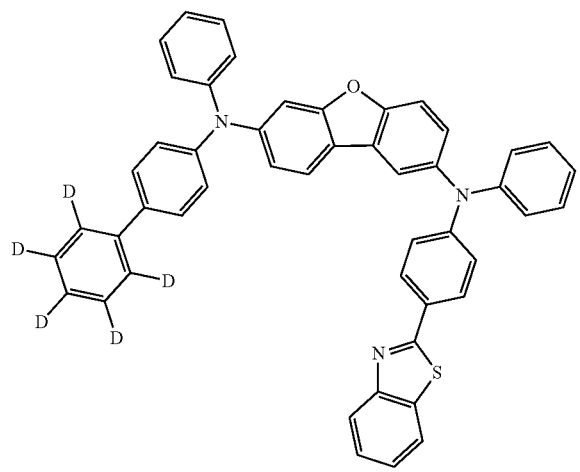
P-86
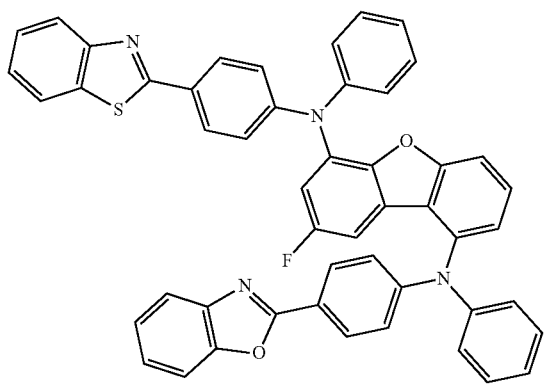

P-87

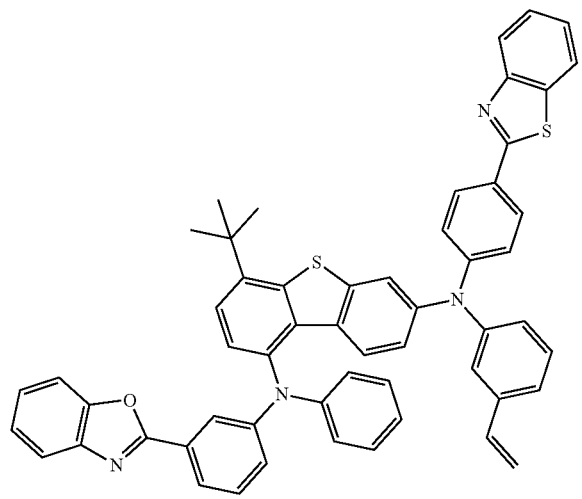

P-88

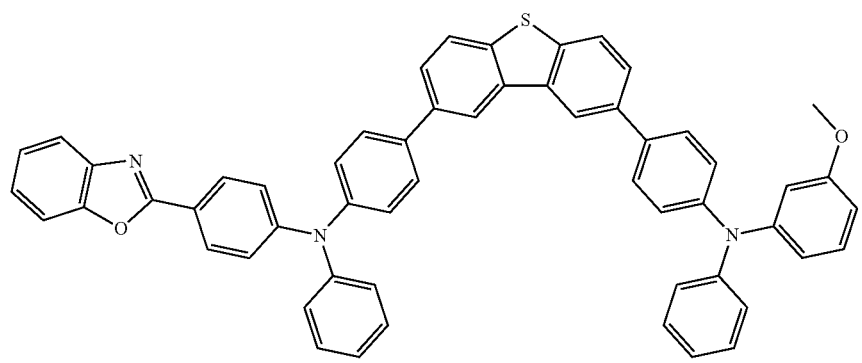

The compound included in each of the capping layer and the organic material layer may be a single compound or two or more types of compounds having different structures.

For example, in the organic material layer, two types of compounds having different structures from among the above-described compounds may be mixed at a mole ratio of from 99:1 to 1:99.

Synthesis examples of the compound represented by the Formula 1 and fabrication examples of the organic electric element according to embodiments of the present disclosure will be described in detail hereinafter, but the present disclosure is not limited thereto.

Synthesis Examples

The compound (or final products) represented by Formula 1 according to the present disclosure is synthesized by reacting Sub 1 and Sub 2 as in Reaction Scheme 1 below but is not limited thereto. In the Reaction Scheme 1 below, X, $L^1$ to $L^6$, $Ar^1$ to $Ar^4$, $R^1$, $R^2$, a, and b are the same as those described above regarding Formula 1, and Hal1 is Br, Cl or I.

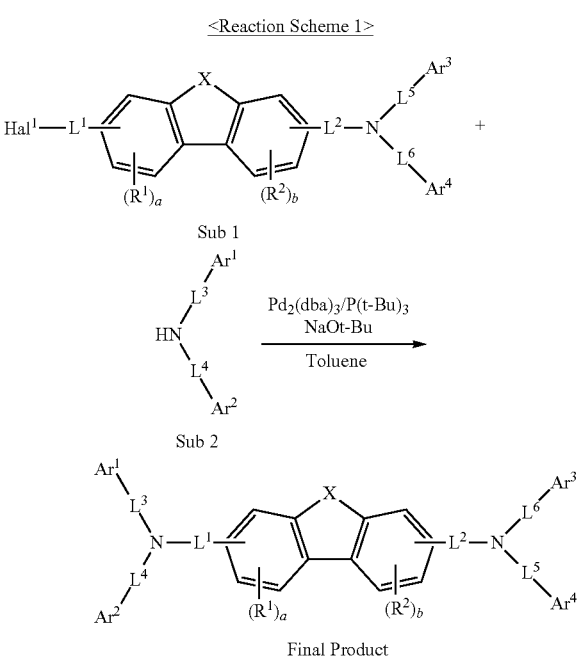

<Reaction Scheme 1>

However, if the amino group of Sub 1 is the same as Sub 2, the final product may be directly synthesized through Sub 1a and Sub 2

Synthesis Example of Sub 1

Sub 1 of the Reaction Scheme 1 may be synthesized by a reaction path of Reaction Scheme 2 below, but it is not limited thereto.

Hale is Br, Cl or I.

<Reaction Scheme 2>

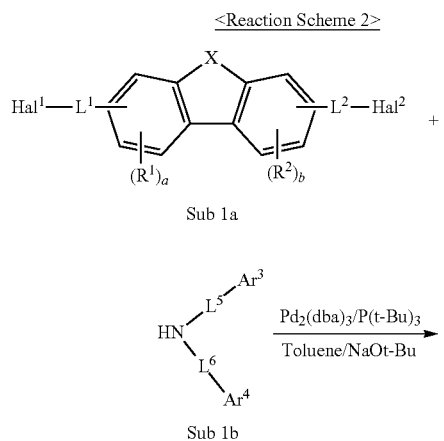

Sub 1

1. Synthesis Example of Sub 1-2

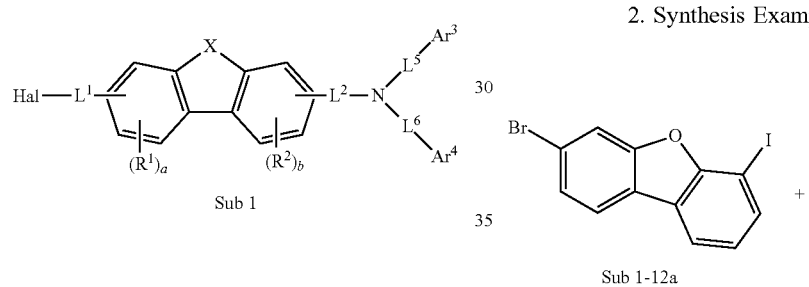

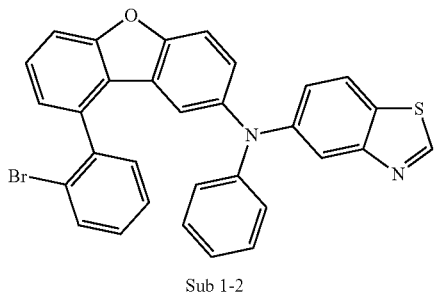

Sub 1-2

Sub 1-2a (50 g, 111.3 mmol), Sub 1-2b (25.2 g, 111.3 mmol), Pd$_2$(dba)$_3$ (3.1 g, 3.3 mmol), P(t-Bu)$_3$ (1.4 g, 6.7 mmol), NaOt-Bu (21.4 g, 222.7 mmol), and toluene (557 mL) in a round bottom flask were added, and then the reaction was carried out at 50° C. Upon completion of the reaction, the mixture was extracted with CH$_2$Cl$_2$ and water, the organic material layer was dried over MgSO$_4$, concentrated, and the resulting organic material was recrystallized by silicagel column to obtain 45.1 g of a product. (Yield: 74%)

2. Synthesis Example of Sub 1-12

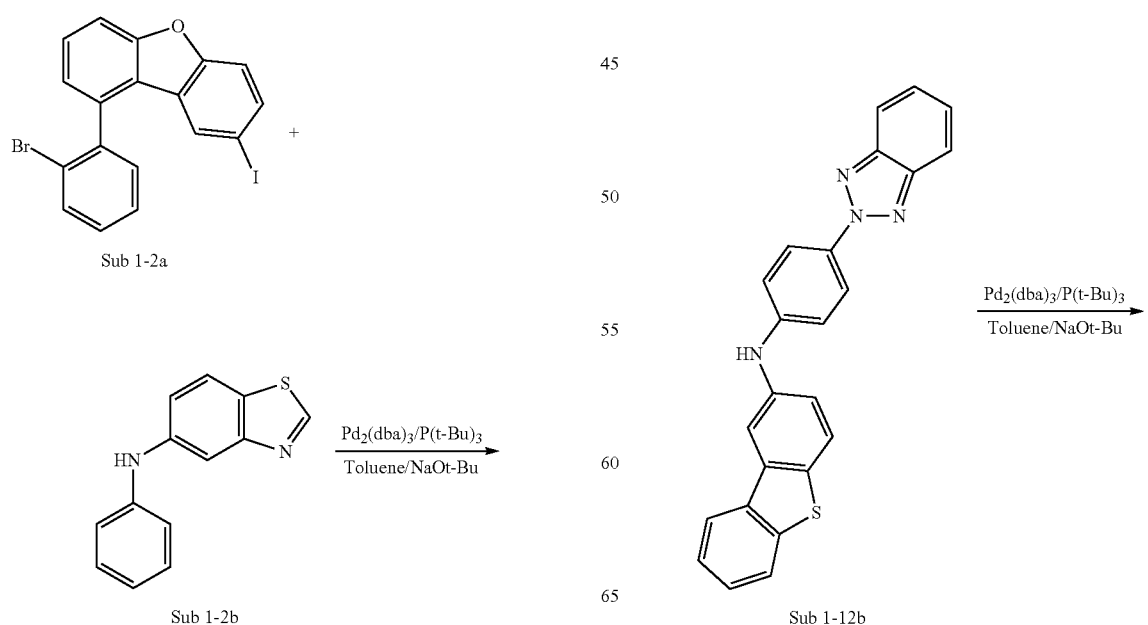

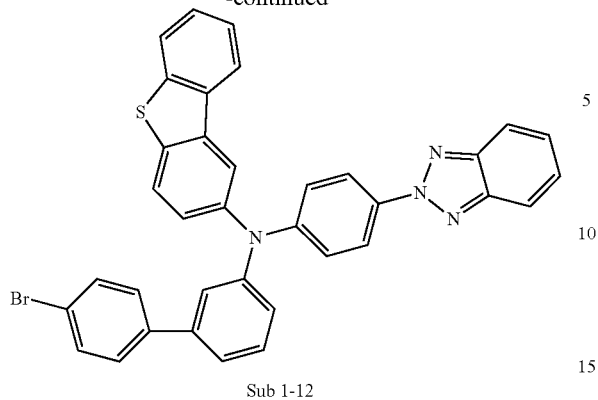
Sub 1-12

Sub 1-12a (50 g, 134.1 mmol), Sub 1-12b (52.6 g, 134.1 mmol), Pd$_2$(dba)$_3$ (3.7 g, 4.0 mmol), P(t-Bu)$_3$ (1.6 g, 8.0 mmol), NaOt-Bu (25.8 g, 268.1 mmol), and toluene (670 mL) in a round bottom flask were used in the same manner as in Sub 1-2 to obtain 52.8 g of the product. (Yield: 72%)

In addition, compounds belonging to Sub 1 may be, but are not limited to, the following compounds. Table 1 represents field desorption-mass spectrometry (FD-MS) values of the compounds belonging to Sub 1.

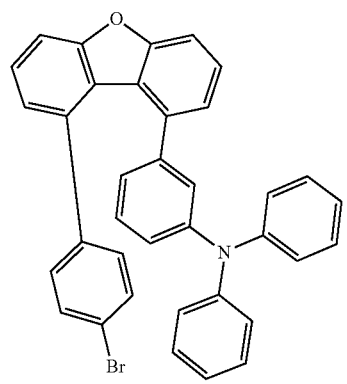
Sub 1-1

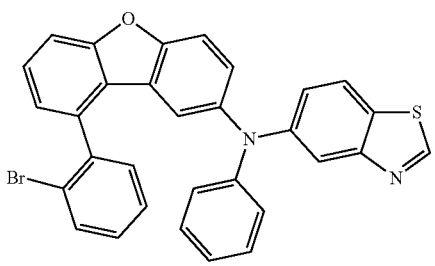
Sub 1-2

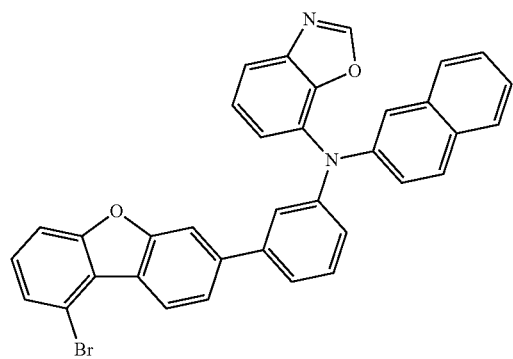
Sub 1-3

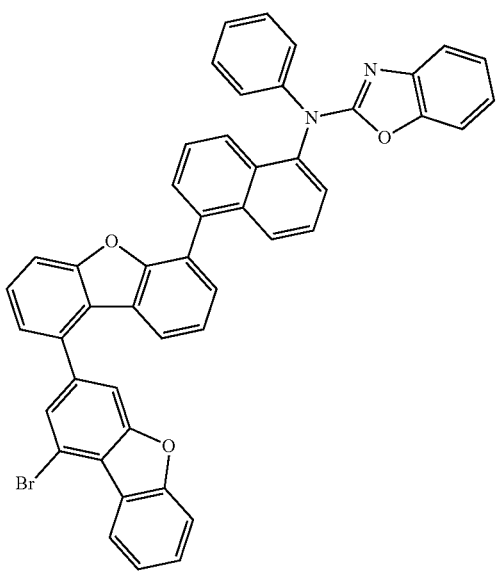
Sub 1-4

-continued
Sub 1-5
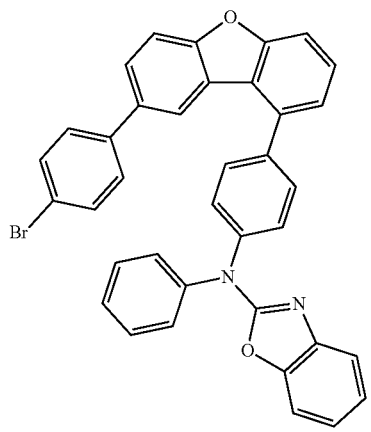
Sub 1-6
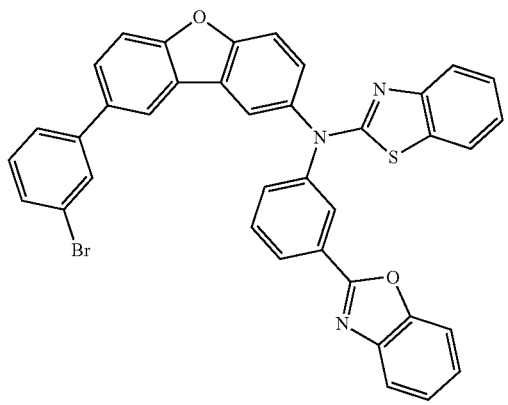
Sub 1-7
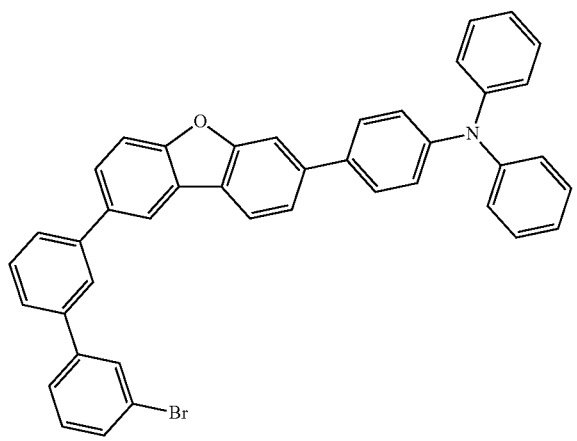
Sub 1-8
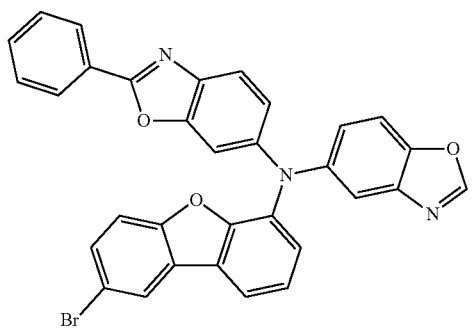
Sub 1-9
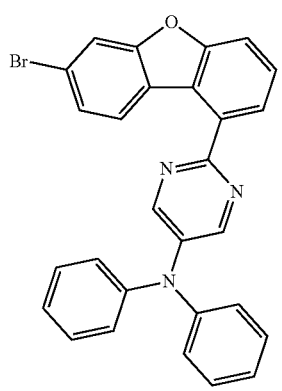
Sub 1-10
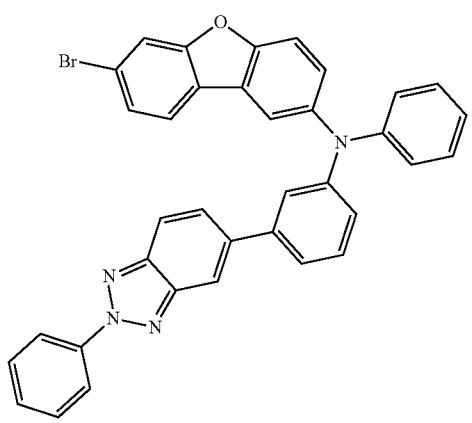

-continued
Sub 1-11
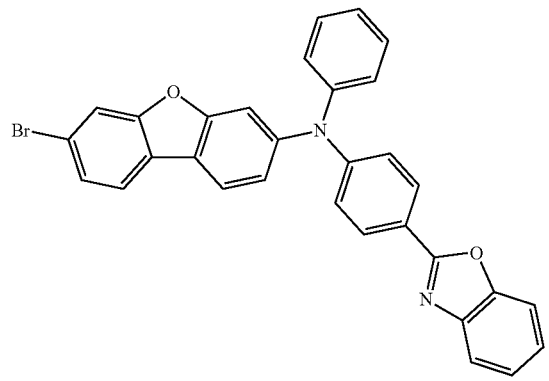
Sub 1-12
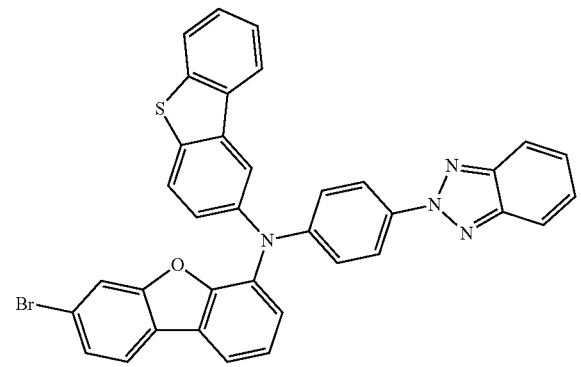
Sub 1-13
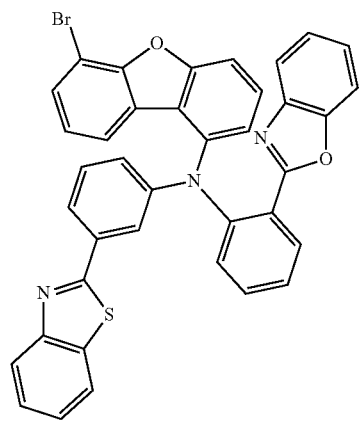
Sub 1-14
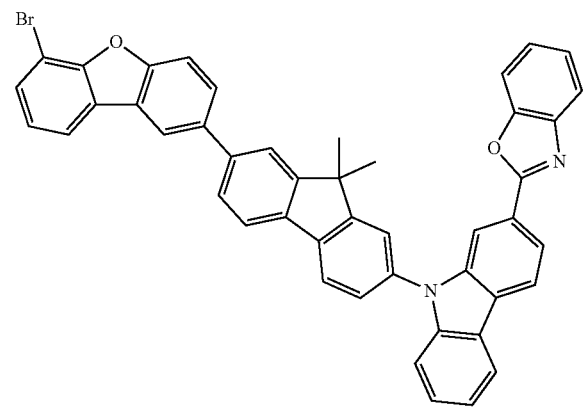
Sub 1-15
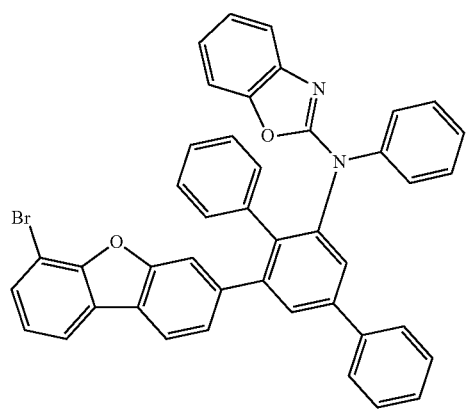
Sub 1-16
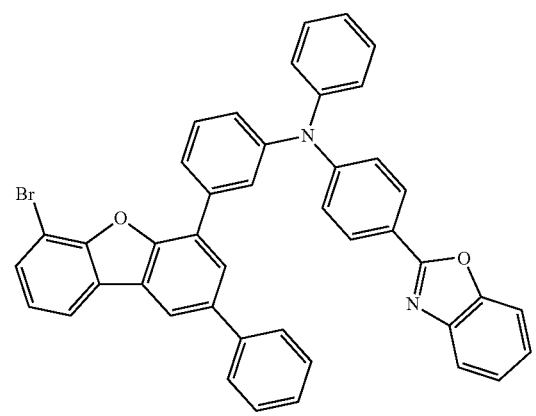

Sub 1-17
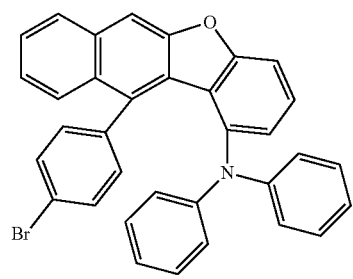
Sub 1-18
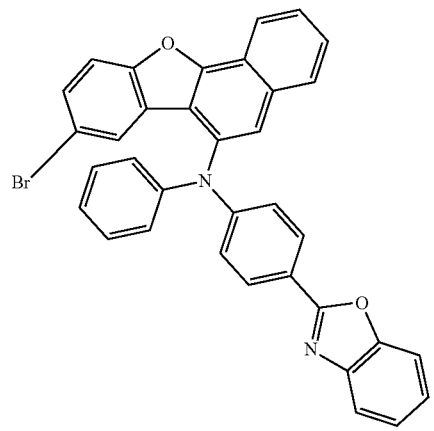
Sub 1-19
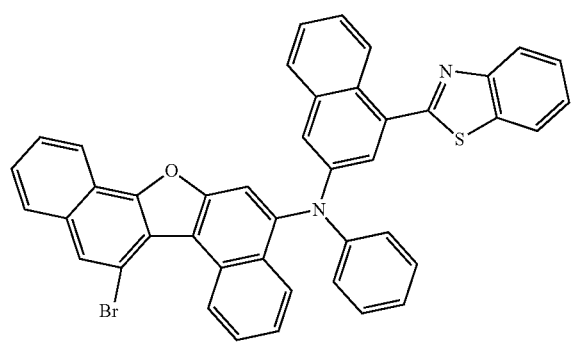
Sub 1-20
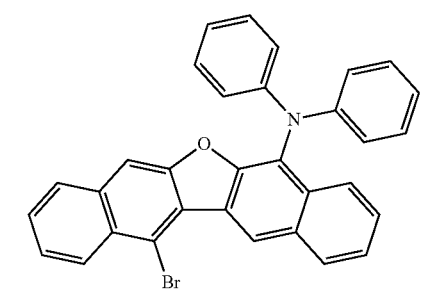
Sub 1-21
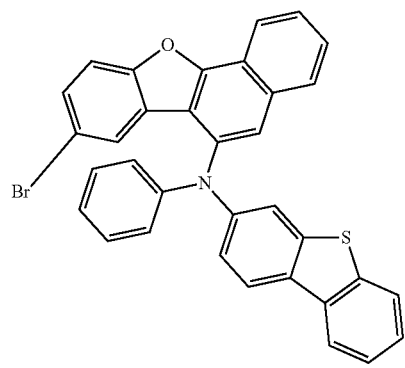
Sub 1-22
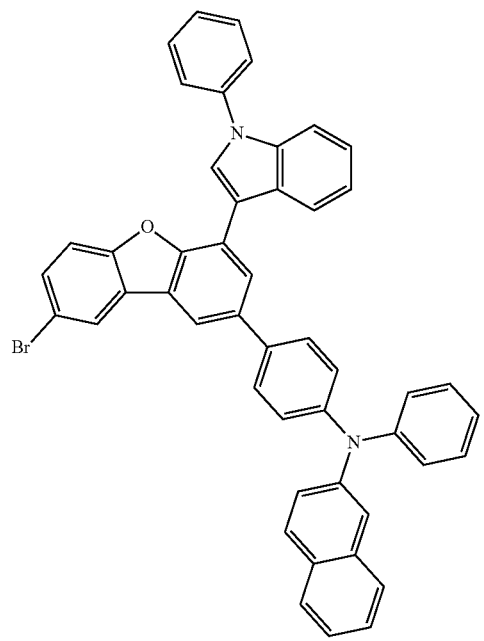

-continued
Sub 1-23
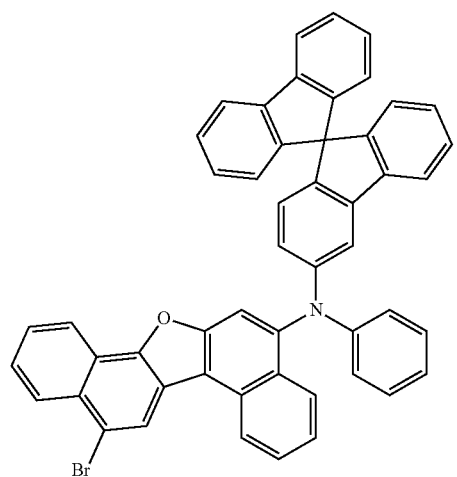
Sub 1-24
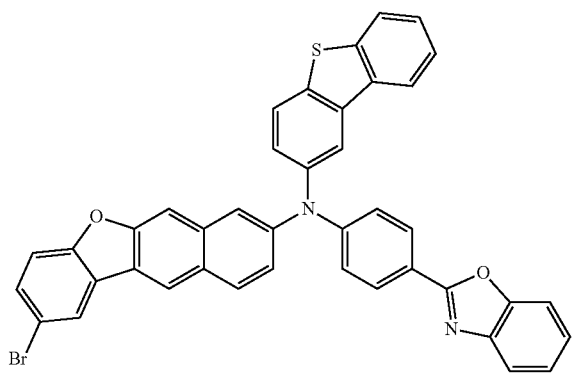
Sub 1-25
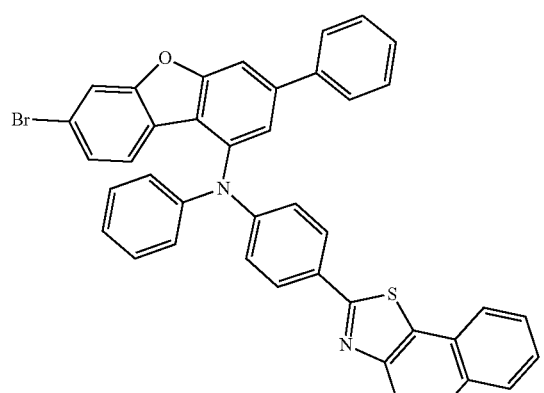
Sub 1-26
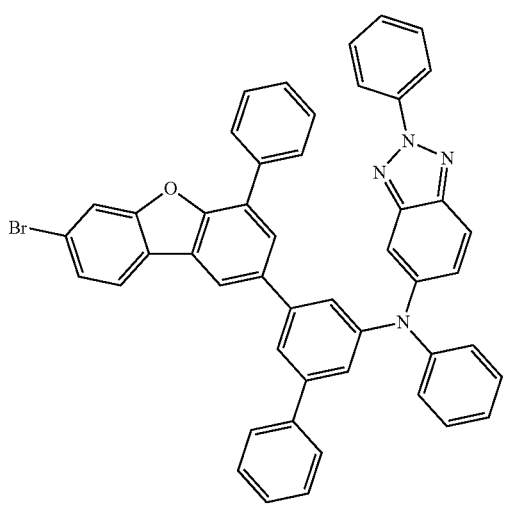
Sub 1-27
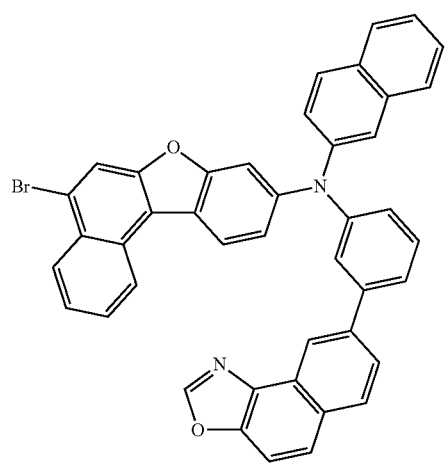
Sub 1-28
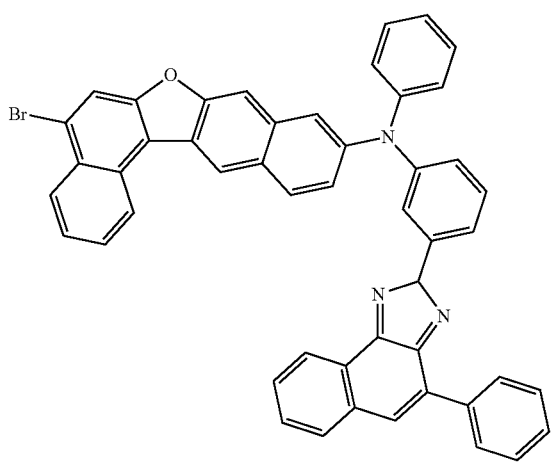

-continued
Sub 1-29
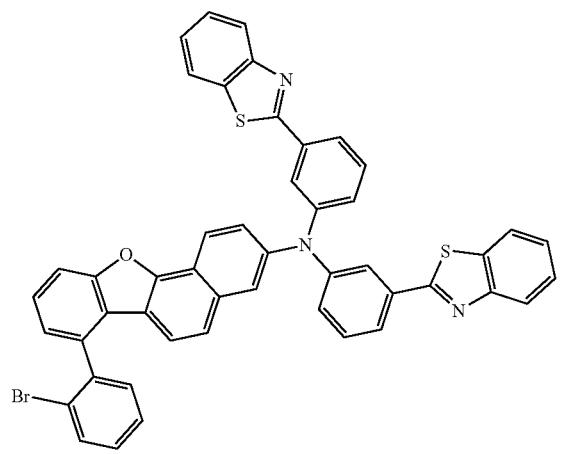
Sub 1-30
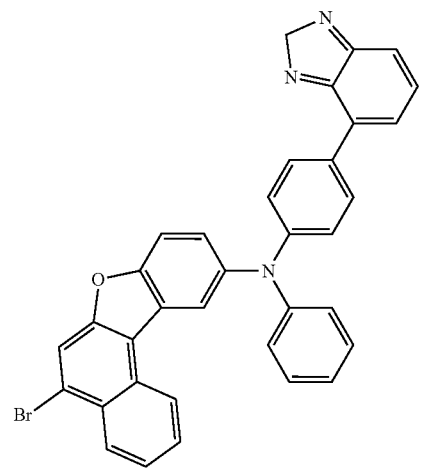
Sub 1-31
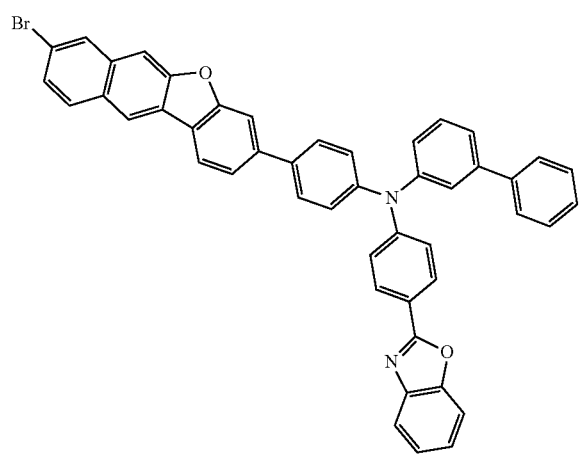
Sub 1-32
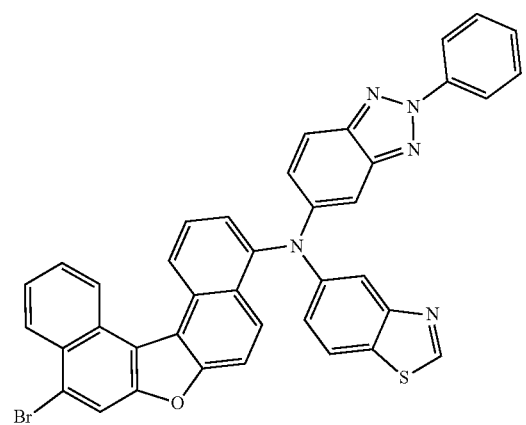
Sub 1-33
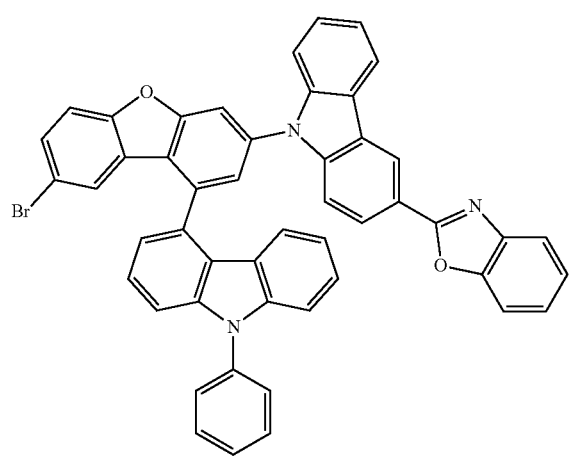
Sub 1-34
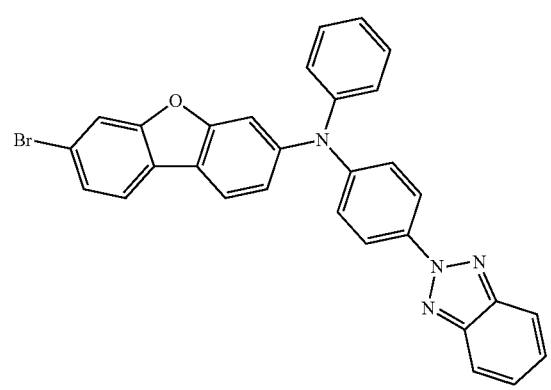

Sub 1-35
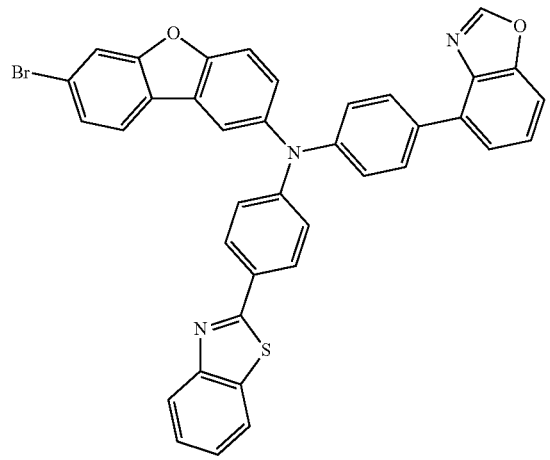
Sub 1-36
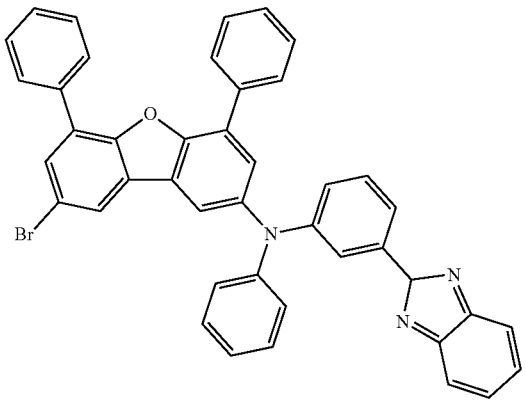
Sub 1-37
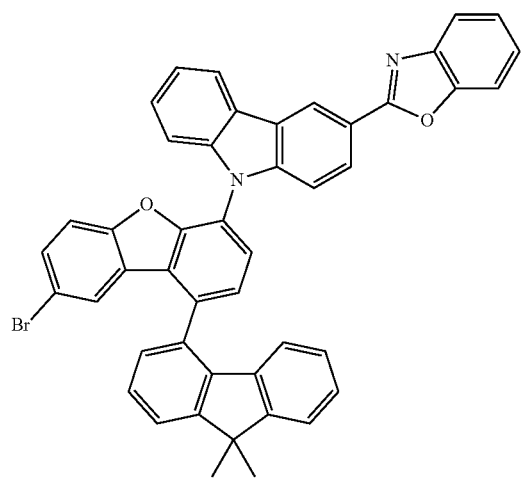
Sub 1-38
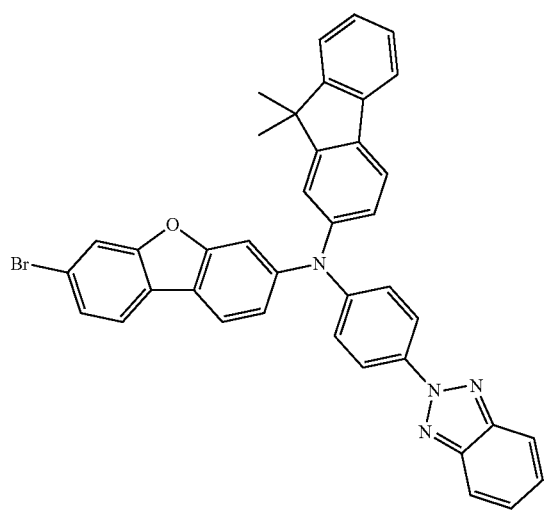
Sub 1-39
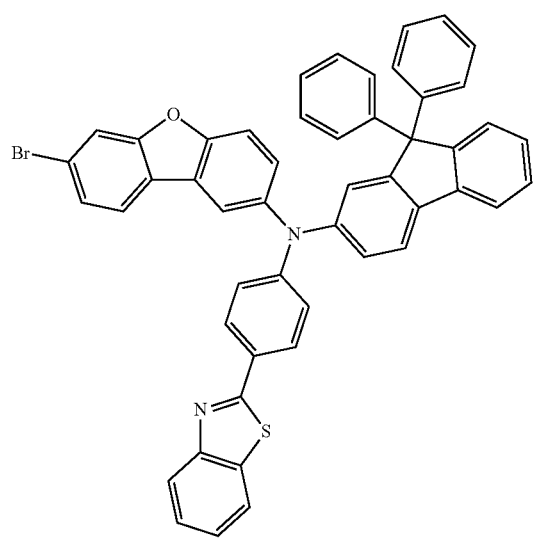
Sub 1-40
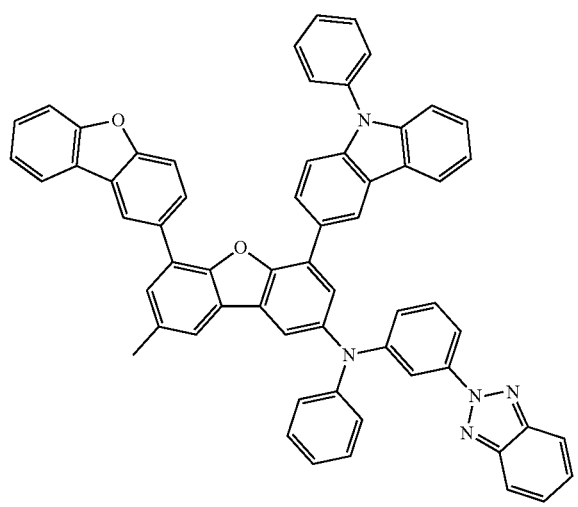

-continued
Sub 1-41
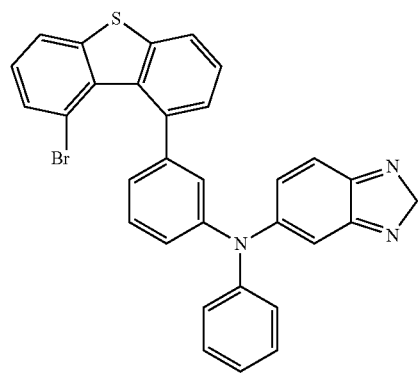
Sub 1-42
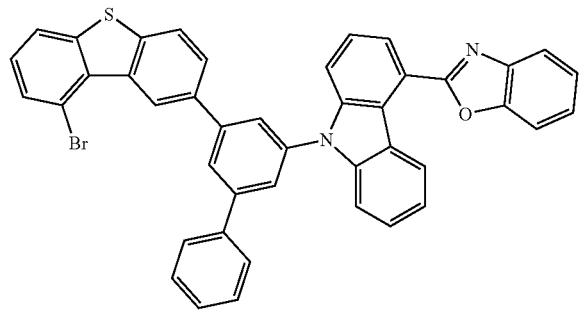
Sub 1-43
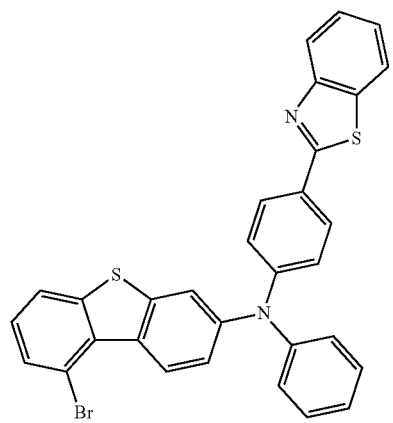
Sub 1-44
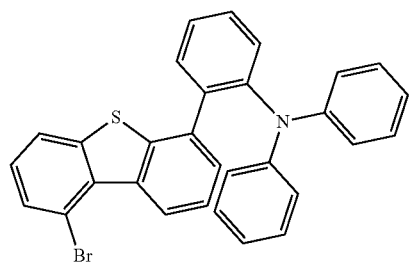
Sub 1-45
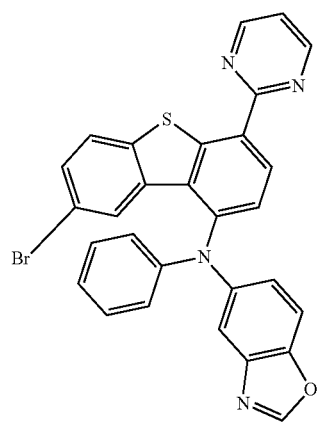
Sub 1-46
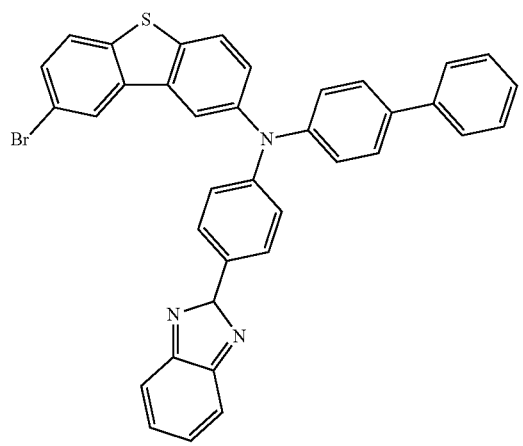

Sub 1-47
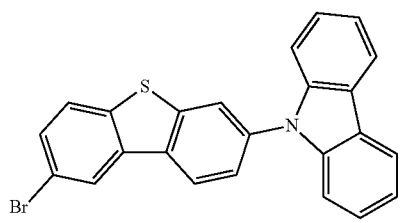
Sub 1-48
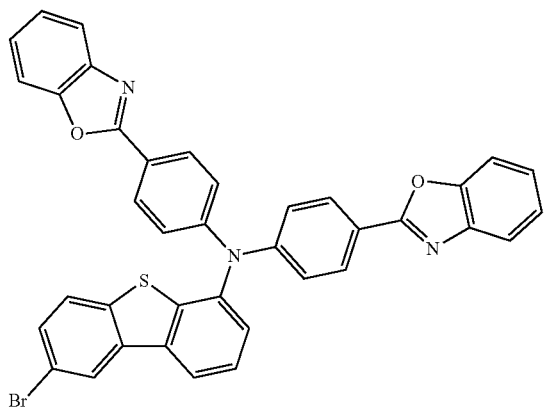
Sub 1-49
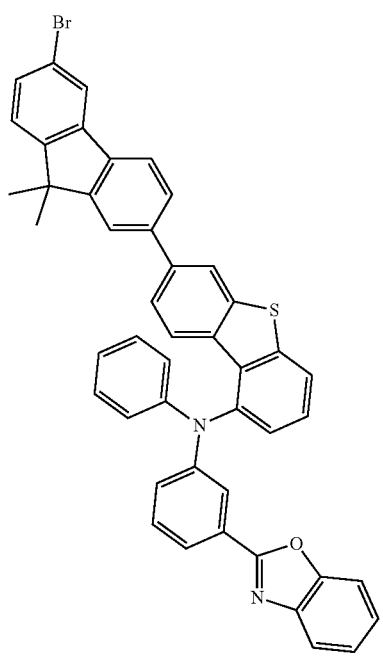
Sub 1-50
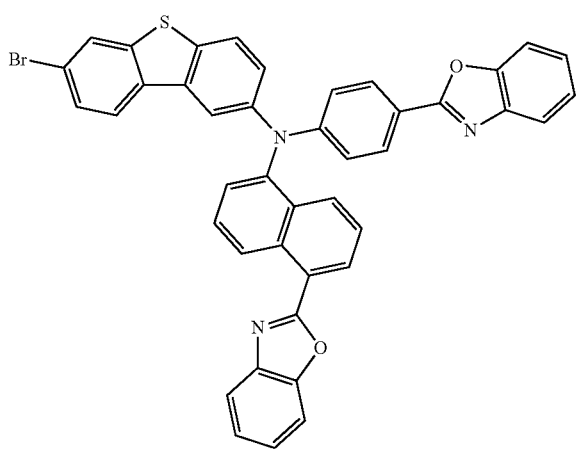
Sub 1-51
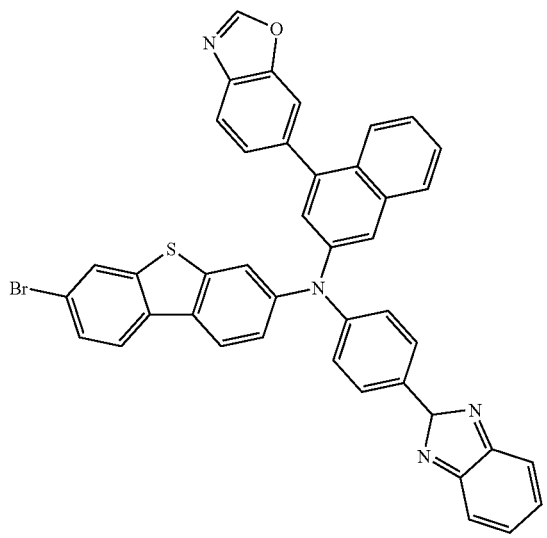
Sub 1-52
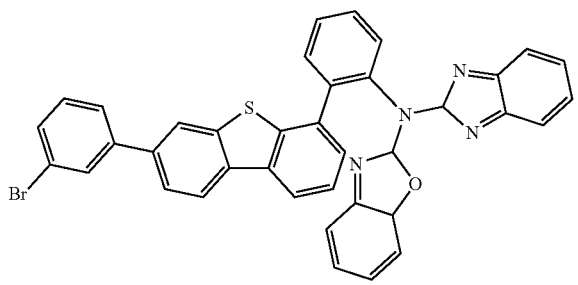

Sub 1-53
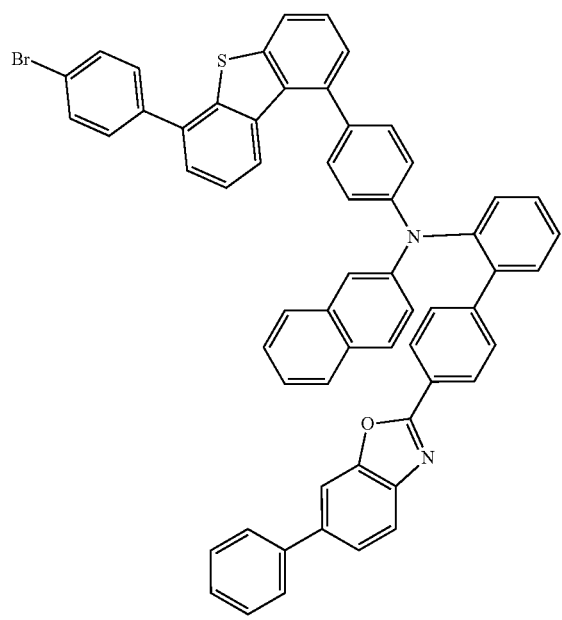
Sub1-54
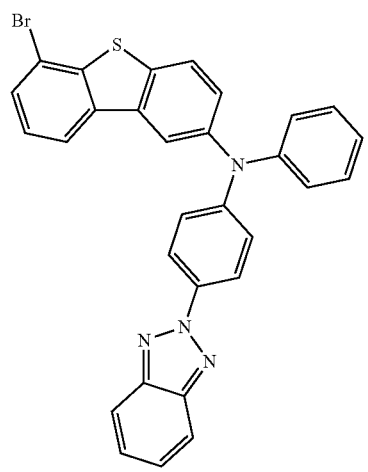
Sub 1-55
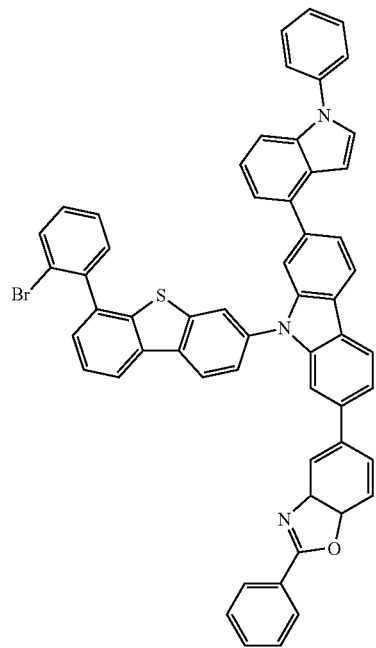
Sub 1-56
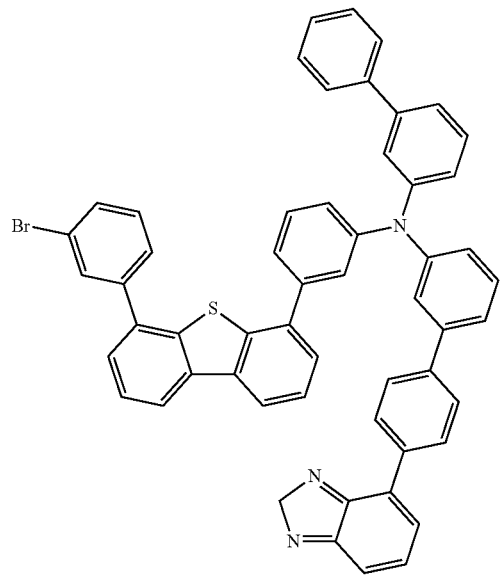

-continued
Sub 1-57
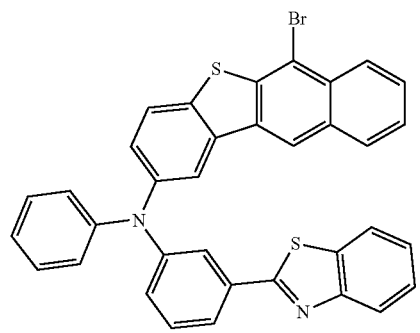
Sub 1-58
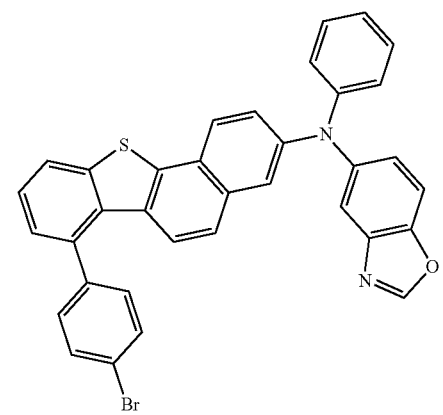
Sub 1-59
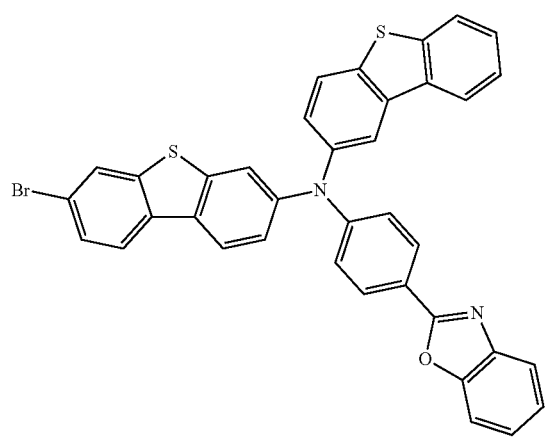
Sub 1-60
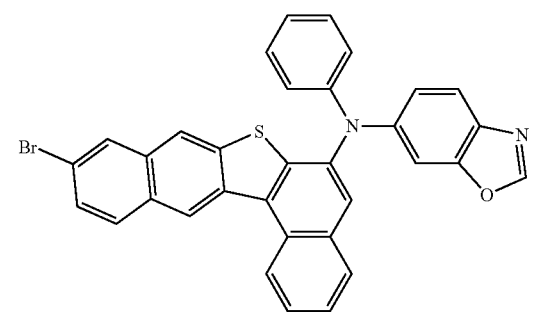
Sub 1-61
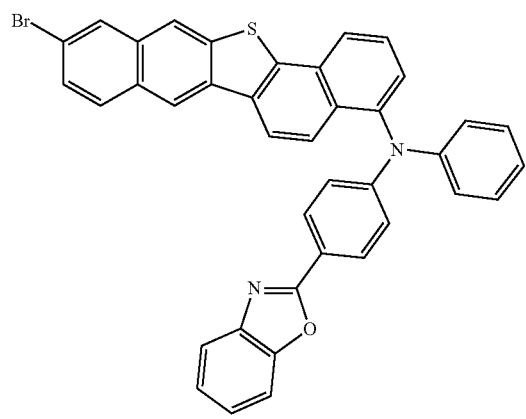
Sub 1-62
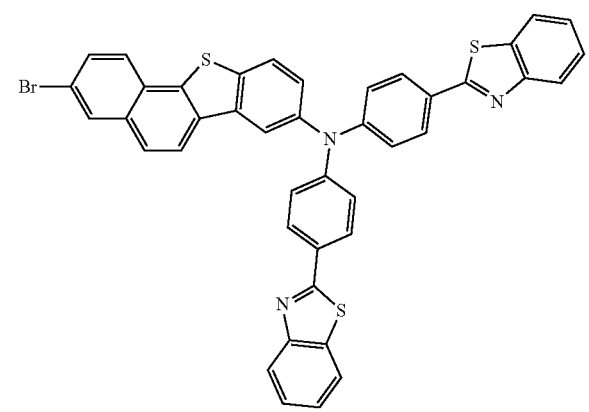

Sub 1-63
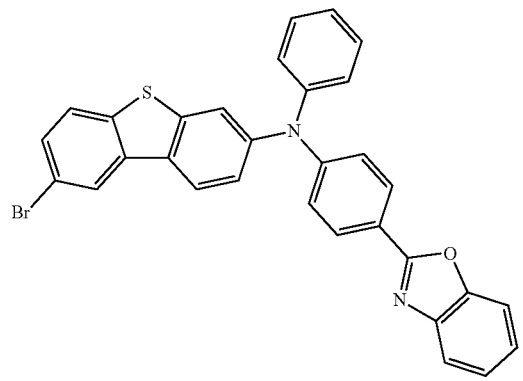
Sub 1-64
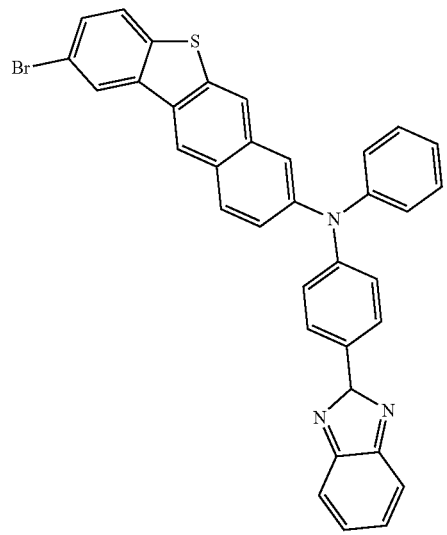
Sub 1-65
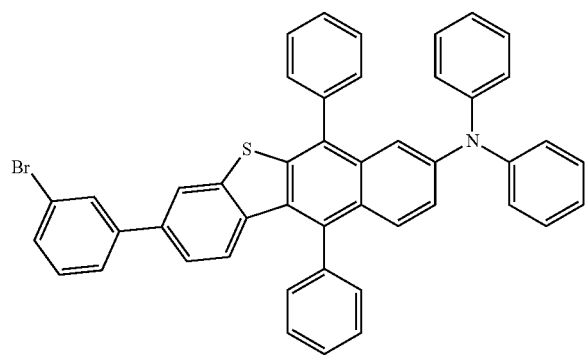
Sub 1-66
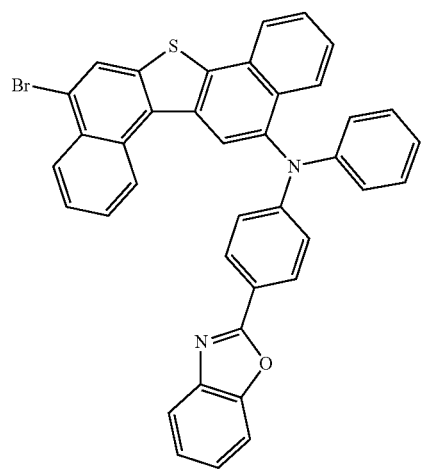
Sub 1-67
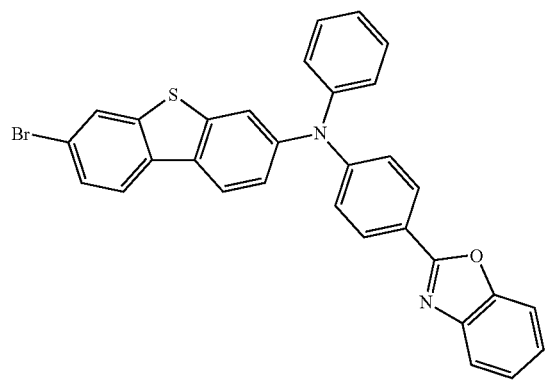
Sub 1-68
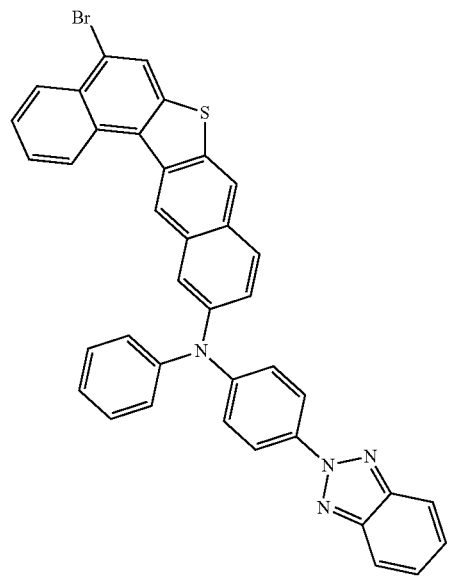

Sub 1-69
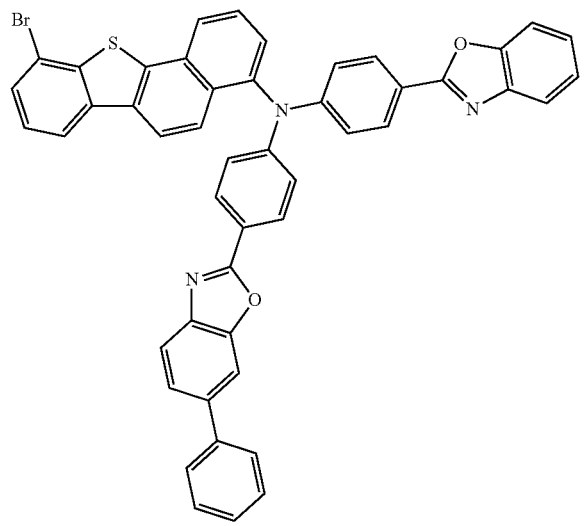
Sub 1-70
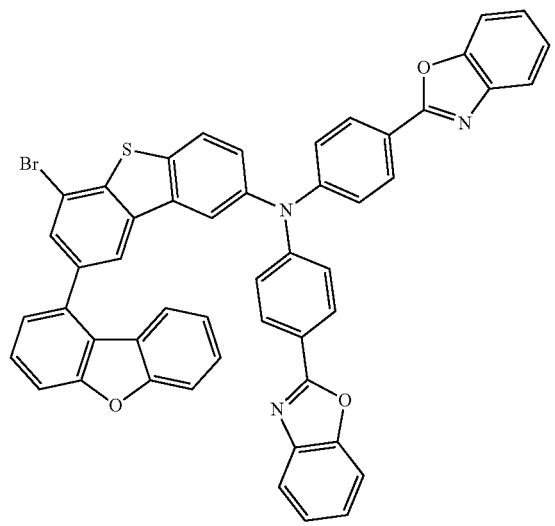
Sub 1-71
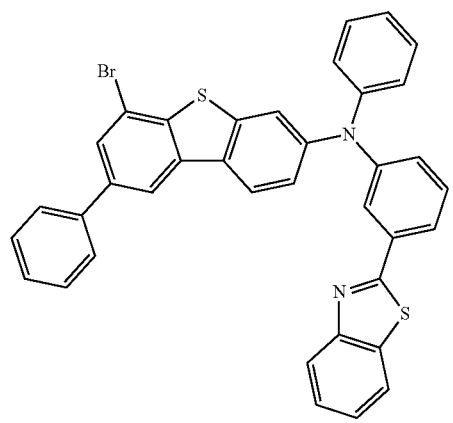
Sub 1-72
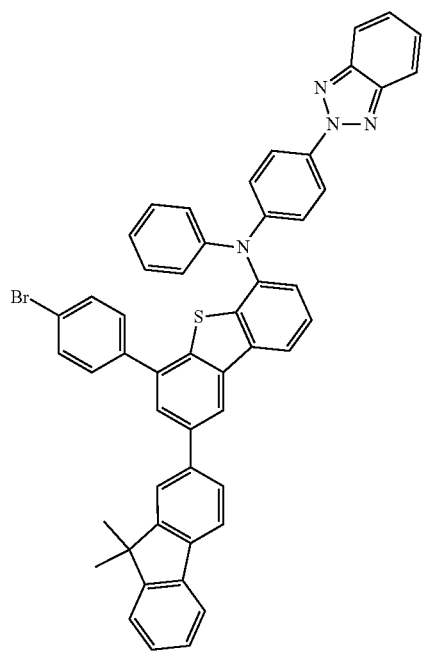

-continued
Sub 1-73
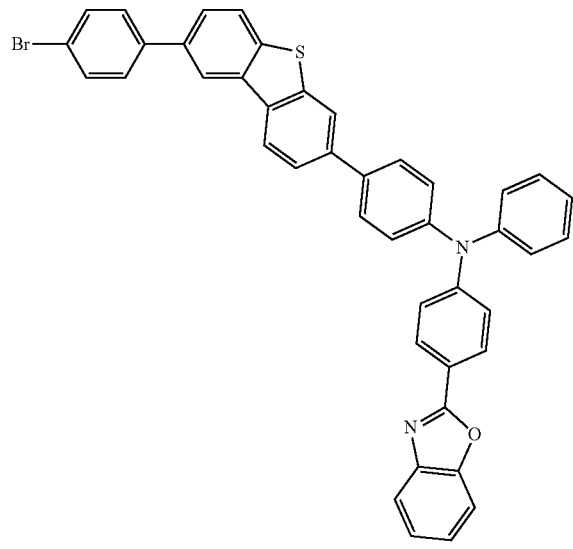
Sub 1-74
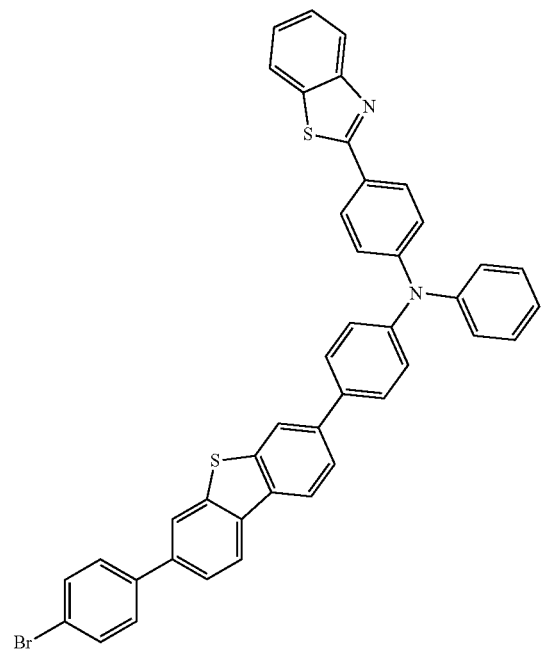
Sub 1-75
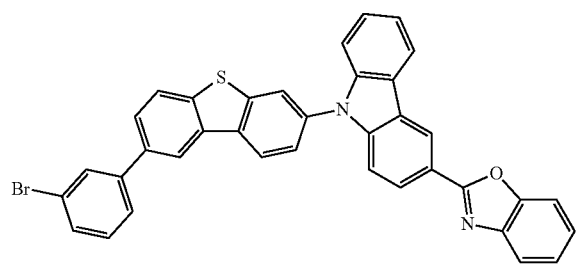
Sub 1-76
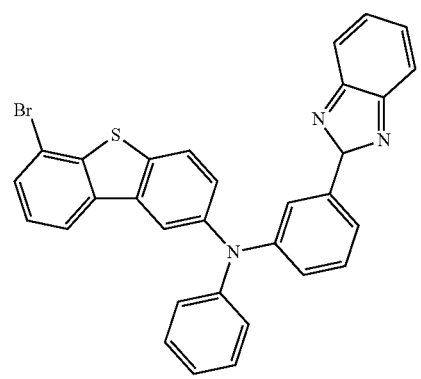

-continued
Sub 1-77
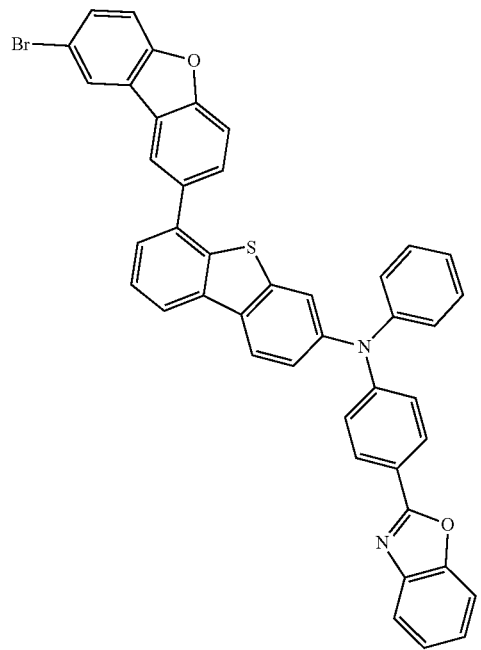
Sub 1-78
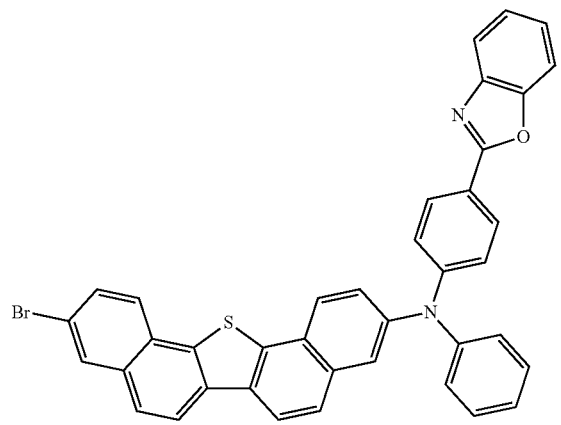
Sub 1-79
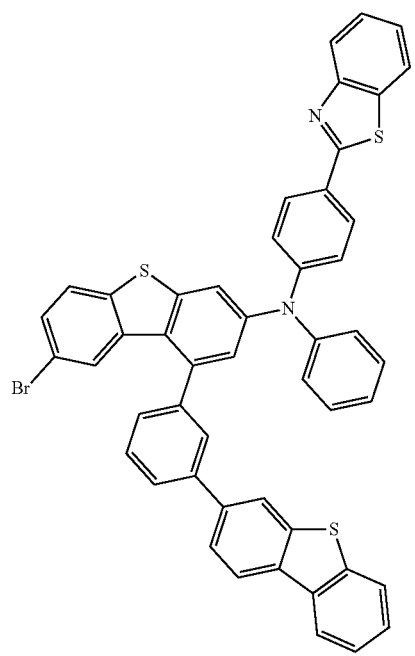
Sub 1-80
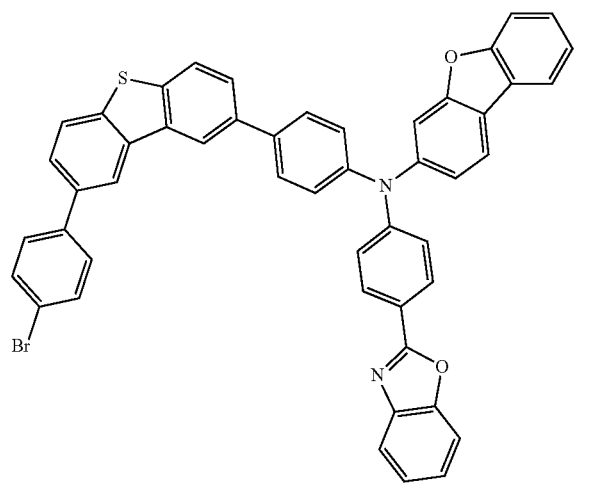

-continued
Sub 1-81
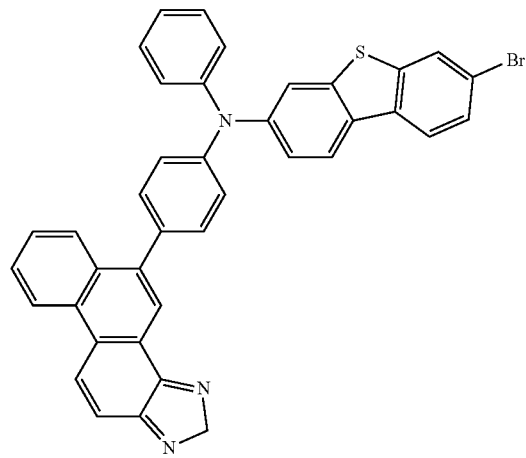
Sub 1-82
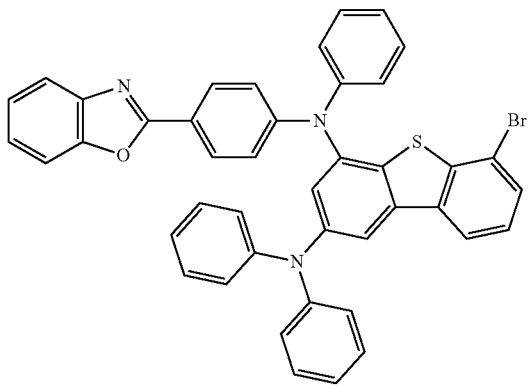
Sub 1-83
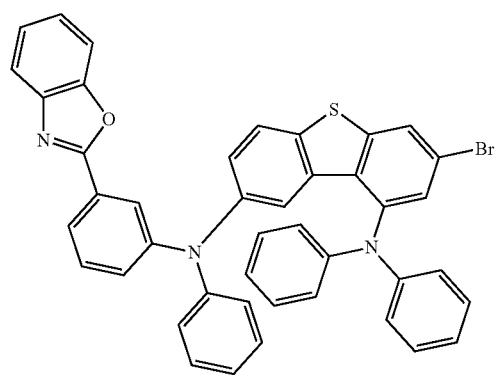
Sub 1-84
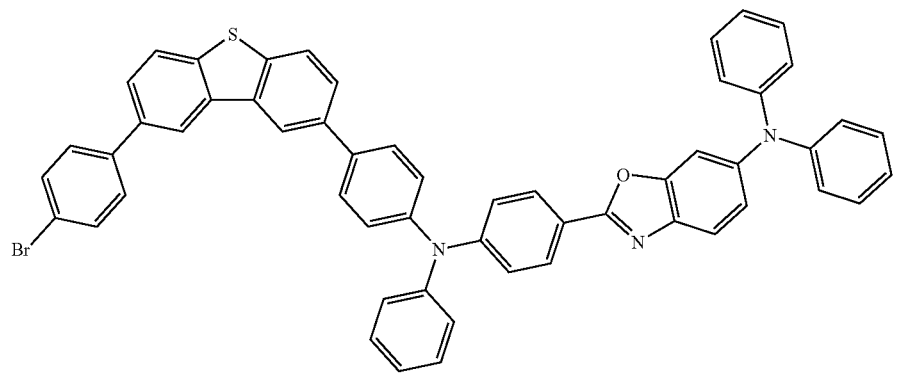
Sub 1-85
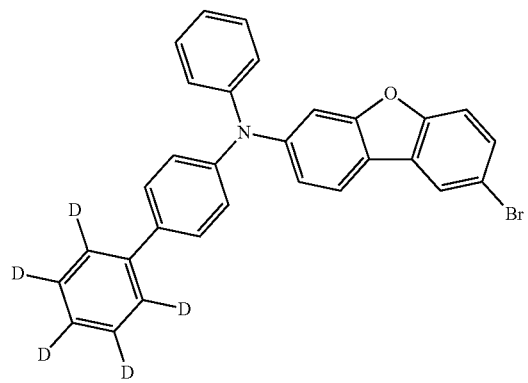
Sub 1-86
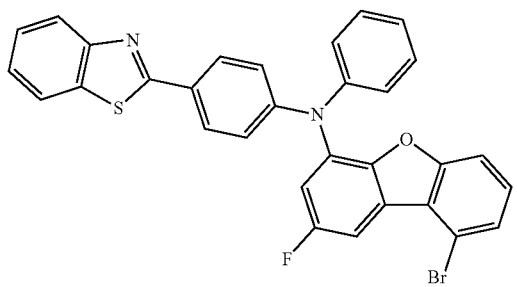

-continued

Sub 1-87

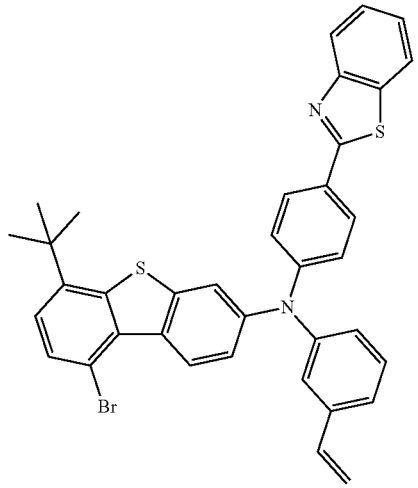

Sub 1-88

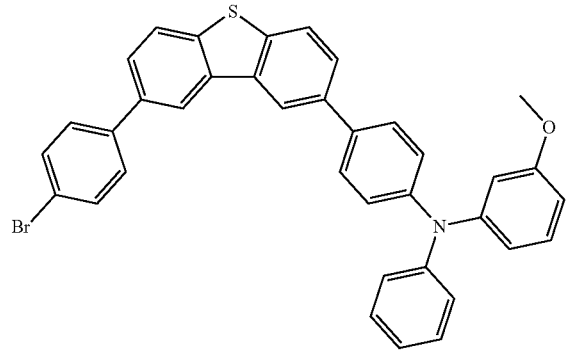

TABLE 1

| Compound | FD-MS | Compound | FD-MS |
|---|---|---|---|
| Sub 1-1 | m/z = 565.1 ($C_{36}H_{24}BrNO$ = 566.5) | Sub 1-2 | m/z = 546.04 ($C_{31}H_{19}BrN_2OS$ = 547.47) |
| Sub 1-3 | m/z = 580.08 ($C_{35}H_{21}BrN_2O_2$ = 581.47) | Sub 1-4 | m/z = 746.12 ($C_{47}H_{27}BrN_2O_3$ = 747.65) |
| Sub 1-5 | m/z = 606.09 ($C_{37}H_{23}BrN_2O_2$ = 607.51) | Sub 1-6 | m/z = 663.06 ($C_{38}H_{22}BrN_3O_2S$ = 664.58) |
| Sub 1-7 | m/z = 641.14 ($C_{42}H_{28}BrNO$ = 642.6) | Sub 1-8 | m/z = 571.05 ($C_{32}H_{18}BrN_3O_3$ = 572.42) |
| Sub 1-9 | m/z = 491.06 ($C_{28}H_{18}BrN_3O$ = 492.38) | Sub 1-10 | m/z = 606.11 ($C_{36}H_{23}BrN_4O$ = 607.51) |
| Sub 1-11 | m/z = 530.06 ($C_{31}H_{19}BrN_2O_2$ = 531.41) | Sub 1-12 | m/z = 636.06 ($C_{36}H_{21}BrN_4OS$ = 637.56) |
| Sub 1-13 | m/z = 663.06 ($C_{38}H_{22}BrN_3O_2S$ = 664.58) | Sub 1-14 | m/z = 720.14 ($C_{46}H_{29}BrN_2O_2$ = 721.65) |
| Sub 1-15 | m/z = 682.13 ($C_{43}H_{27}BrN_2O_2$ = 683.61) | Sub 1-16 | m/z = 682.13 ($C_{43}H_{27}BrN_2O_2$ = 683.61) |
| Sub 1-17 | m/z = 539.09 ($C_{34}H_{22}BrNO$ = 540.46) | Sub 1-18 | m/z = 580.08 ($C_{35}H_{21}BrN_2O_2$ = 581.47) |
| Sub 1-19 | m/z = 696.09 ($C_{43}H_{25}BrN_2OS$ = 697.65) | Sub 1-20 | m/z = 513.07 ($C_{32}H_{20}BrNO$ = 514.42) |
| Sub 1-21 | m/z = 569.04 ($C_{34}H_{20}BrNOS$ = 570.5) | Sub 1-22 | m/z = 730.16 ($C_{48}H_{31}BrN_2O$ = 731.69) |
| Sub 1-23 | m/z = 751.15 ($C_{51}H_{30}BrNO$ = 752.71) | Sub 1-24 | m/z = 686.07 ($C_{41}H_{23}BrN_2O_2S$ = 687.61) |
| Sub 1-25 | m/z = 672.09 ($C_{41}H_{25}BrN_2OS$ = 673.63) | Sub 1-26 | m/z = 758.17 ($C_{48}H_{31}BrN_4O$ = 759.71) |
| Sub 1-27 | m/z = 680.11 ($C_{43}H_{25}BrN_2O_2$ = 681.59) | Sub 1-28 | m/z = 755.16 ($C_{49}H_{30}BrN_3O$ = 756.7) |
| Sub 1-29 | m/z = 805.09 ($C_{48}H_{28}BrN_3OS_2$ = 806.8) | Sub 1-30 | m/z = 579.09 ($C_{35}H_{22}BrN_3O$ = 580.49) |
| Sub 1-31 | m/z = 732.14 ($C_{47}H_{29}BrN_2O_2$ = 733.67) | Sub 1-32 | m/z = 687.07 ($C_{39}H_{22}BrN_5OS$ = 688.6) |
| Sub 1-33 | m/z = 769.14 ($C_{49}H_{28}BrN_3O_2$ = 770.69) | Sub 1-34 | m/z = 530.07 ($C_{30}H_{19}BrN_4O$ = 531.41) |
| Sub 1-35 | m/z = 663.06 ($C_{38}H_{22}BrN_3O_2S$ = 664.58) | Sub 1-36 | m/z = 681.14 ($C_{43}H_{28}BrN_3O$ = 682.62) |
| Sub 1-37 | m/z = 720.14 ($C_{46}H_{29}BrN_2O_2$ = 721.65) | Sub 1-38 | m/z = 646.14 ($C_{39}H_{27}BrN_4O$ = 647.58) |
| Sub 1-39 | m/z = 786.13 ($C_{50}H_{31}BrN_2OS$ = 787.78) | Sub 1-40 | m/z = 873.31 ($C_{61}H_{39}N_5O_2$ = 874.02) |
| Sub 1-41 | m/z = 545.06 ($C_{31}H_{20}BrN_3S$ = 546.49) | Sub 1-42 | m/z = 696.09 ($C_{43}H_{25}BrN_2OS$ = 697.65) |
| Sub 1-43 | m/z = 562.02 ($C_{31}H_{19}BrN_2S_2$ = 563.53) | Sub 1-44 | m/z = 505.05 ($C_{30}H_{20}BrNS$ = 506.46) |
| Sub 1-45 | m/z = 548.03 ($C_{29}H_{17}BrN_4OS$ = 549.45) | Sub 1-46 | m/z = 621.09 ($C_{37}H_{24}BrN_3S$ = 622.58) |
| Sub 1-47 | m/z = 427 ($C_{24}H_{14}BrNS$ = 428.35) | Sub 1-48 | m/z = 663.06 ($C_{38}H_{22}BrN_3O_2S$ = 664.58) |
| Sub 1-49 | m/z = 738.13 ($C_{46}H_{31}BrN_2OS$ = 739.73) | Sub 1-50 | m/z = 713.08 ($C_{42}H_{24}BrN_3O_2S$ = 714.64) |
| Sub 1-51 | m/z = 712.09 ($C_{42}H_{25}BrN_4OS$ = 713.65) | Sub 1-52 | m/z = 664.09 ($C_{38}H_{25}BrN_4OS$ = 665.61) |
| Sub 1-53 | m/z = 900.18 ($C_{59}H_{37}BrN_2OS$ = 901.92) | Sub 1-54 | m/z = 546.05 ($C_{30}H_{19}BrN_4S$ = 547.47) |
| Sub 1-55 | m/z = 889.18 ($C_{57}H_{36}BrN_3OS$ = 890.9) | Sub 1-56 | m/z = 849.18 ($C_{55}H_{36}BrN_3S$ = 850.88) |
| Sub 1-57 | m/z = 612.03 ($C_{35}H_{21}BrN_2S_2$ = 613.59) | Sub 1-58 | m/z = 596.06 ($C_{35}H_{21}BrN_2OS$ = 597.53) |
| Sub 1-59 | m/z = 652.03 ($C_{37}H_{21}BrN_2OS_2$ = 653.61) | Sub 1-60 | m/z = 570.04 ($C_{33}H_{19}BrN_2OS$ = 571.49) |
| Sub 1-61 | m/z = 646.07 ($C_{39}H_{23}BrN_2OS$ = 647.59) | Sub 1-62 | m/z = 745.03 ($C_{42}H_{24}BrN_3S_3$ = 746.76) |
| Sub 1-63 | m/z = 546.04 ($C_{31}H_{19}BrN_2OS$ = 547.47) | Sub 1-64 | m/z = 595.07 ($C_{35}H_{22}BrN_3S$ = 596.55) |
| Sub 1-65 | m/z = 707.13 ($C_{46}H_{30}BrNS$ = 708.72) | Sub 1-66 | m/z = 646.07 ($C_{39}H_{23}BrN_2OS$ = 647.59) |
| Sub 1-67 | m/z = 546.04 ($C_{31}H_{19}BrN_2OS$ = 547.47) | Sub 1-68 | m/z = 646.08 ($C_{38}H_{23}BrN_4S$ = 647.59) |
| Sub 1-69 | m/z = 789.11 ($C_{48}H_{28}BrN_3O_2S$ = 790.74) | Sub 1-70 | m/z = 829.1 ($C_{50}H_{28}BrN_3O_3S$ = 830.76) |
| Sub 1-71 | m/z = 638.05 ($C_{37}H_{23}BrN_2S_2$ = 639.63) | Sub 1-72 | m/z = 814.18 ($C_{51}H_{35}BrN_4S$ = 815.83) |
| Sub 1-73 | m/z = 698.1 ($C_{43}H_{27}BrN_2OS$ = 699.67) | Sub 1-74 | m/z = 714.08 ($C_{43}H_{27}BrN_2S_2$ = 715.73) |
| Sub 1-75 | m/z = 620.06 ($C_{37}H_{21}BrN_2OS$ = 621.55) | Sub 1-76 | m/z = 545.06 ($C_{31}H_{20}BrN_3S$ = 546.49) |
| Sub 1-77 | m/z = 712.08 ($C_{43}H_{25}BrN_2O_2S$ = 713.65) | Sub 1-78 | m/z = 646.07 ($C_{39}H_{23}BrN_2OS$ = 647.59) |
| Sub 1-79 | m/z = 820.07 ($C_{49}H_{29}BrN_2S_3$ = 821.87) | Sub 1-80 | m/z = 788.11 ($C_{49}H_{29}BrN_2O_2S$ = 789.75) |
| Sub 1-81 | m/z = 645.09 ($C_{39}H_{24}BrN_3S$ = 646.61) | Sub 1-82 | m/z = 713.11 ($C_{43}H_{28}BrN_3OS$ = 714.68) |
| Sub 1-83 | m/z = 713.11 ($C_{43}H_{28}BrN_3OS$ = 714.68) | Sub 1-84 | m/z = 865.18 ($C_{55}H_{36}BrN_3OS$ = 866.88) |
| Sub 1-85 | m/z = 494.10 ($C_{30}H_{15}D_5BrNO$ = 495.43) | Sub 1-86 | m/z = 564.03 ($C_{31}H_{18}BrFN_2OS$ = 565.46) |
| Sub 1-87 | m/z = 644.10 ($C_{37}H_{29}BrN_2S_2$ = 645.68) | Sub 1-88 | m/z = 611.09 ($C_{37}H_{26}BrNOS$ = 612.59) |

II. Synthesis of Sub 2

Sub 2 of the Reaction Scheme 1 may be synthesized according to, but not limited to, Reaction Scheme 3 below.

<Reaction Scheme 3>

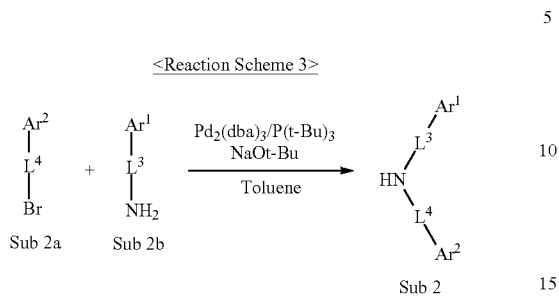

1. Synthesis Example of Sub 2-2

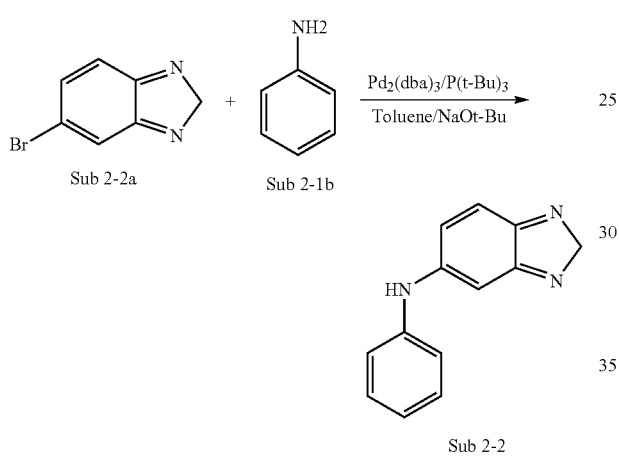

Sub 2-2a (50 g, 253.8 mmol), Sub 2-1b (23.6 g, 253.8 mmol), Pd₂(dba)₃ (7.0 g, 7.6 mmol), P(t-Bu)₃(3.1 g, 15.2 mmol), NaOt-Bu (48.8 g, 507.5 mmol), and toluene (1269 mL) in a round bottom flask were added, and then the reaction was carried out at 80° C. After completion of the reaction, the reaction was extracted with CH₂Cl₂ and water, the organic material layer was dried over MgSO₄, concentrated, and the resulting organic material was recrystallized using silicagel column to obtain 29.0 g of a product. (Yield: 76%)

2. Synthesis Example of Sub 2-8

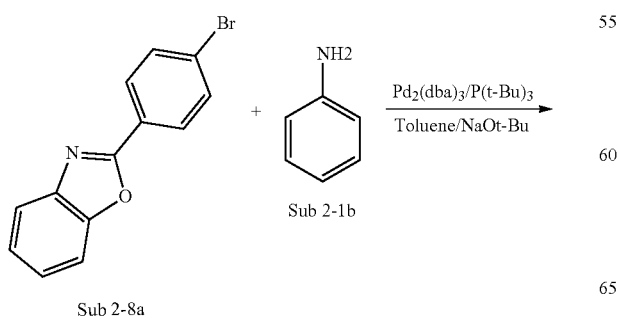

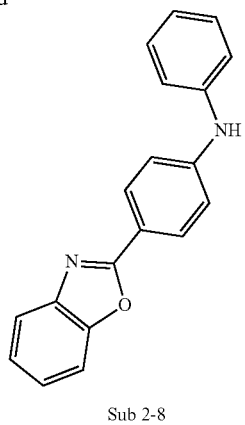

Sub 2-8a (50 g, 182.4 mmol), Sub 2-1b (17.0 g, 182.4 mmol), Pd₂(dba)₃ (5.0 g, 5.5 mmol), P(t-Bu)₃ (2.2 g, 10.9 mmol), NaOt-Bu (35.1 g, 364.8 mmol), and toluene (912 mL) in a round bottom flask were used in the same manner as in Sub 2-2 to obtain 38.6 g of the product. (Yield: 74%)

3. Synthesis Example of Sub 2-44

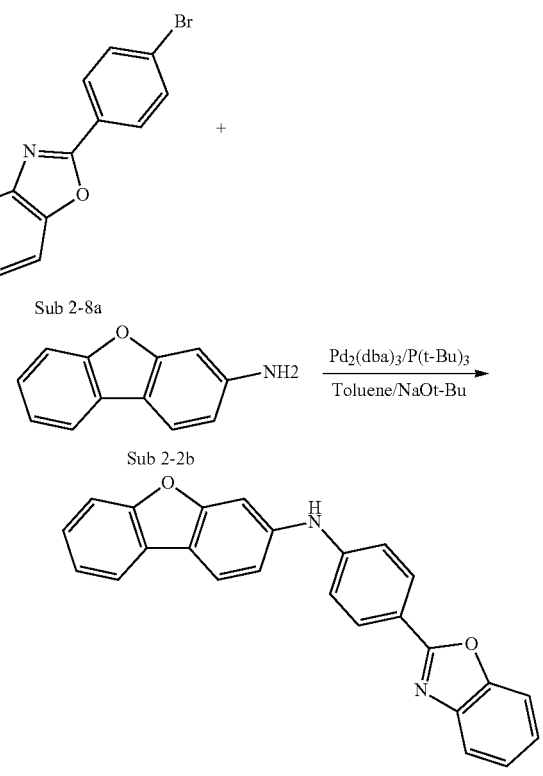

Sub 2-8a (50 g, 182.4 mmol), Sub 2-2b (33.4 g, 182.4 mmol), Pd₂(dba)₃ (5.0 g, 5.5 mmol), P(t-Bu)₃ (2.2 g, 10.9 mmol), NaOt-Bu (35.1 g, 346.8 mmol), and toluene (912 mL) in a round bottom flask were used in the same manner as in Sub 2-2 to obtain 48.1 g of the product. (Yield: 70%)

Compounds belonging to Sub 2 may be, but are not limited to, the following compounds. Table 2 represents FD-MS values of the compounds belonging to Sub 2.

Sub 2-1
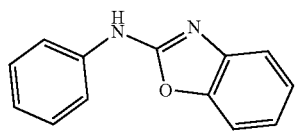
Sub 2-2
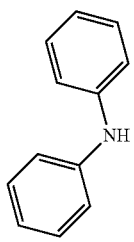
Sub 2-3
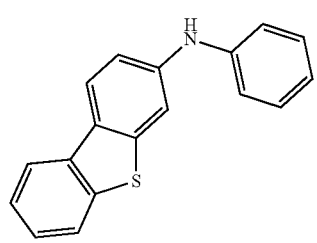
Sub 2-4
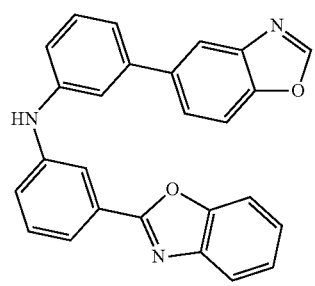
Sub 2-5
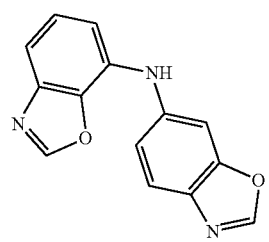
Sub 2-6
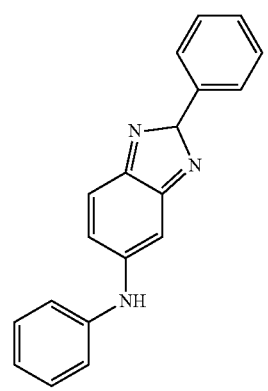
-continued
Sub 2-7
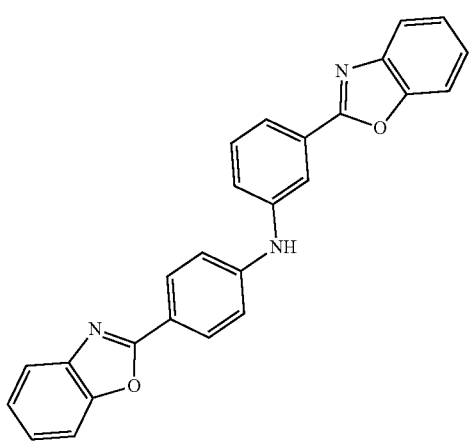
Sub 2-8
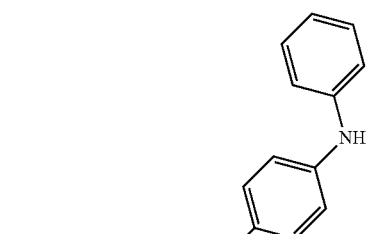
Sub 2-9
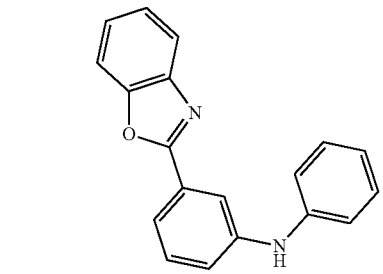
Sub 2-10
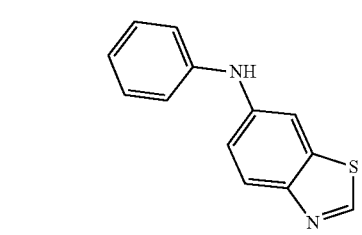
Sub 2-11
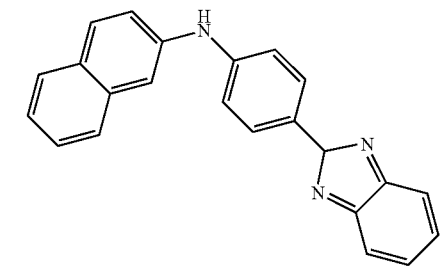

Sub 2-12
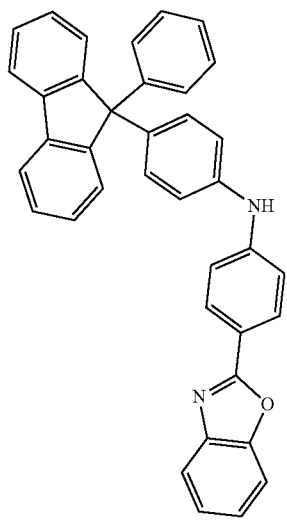
Sub 2-13
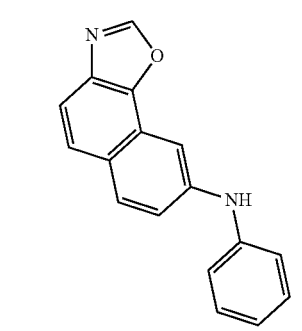
Sub 2-14
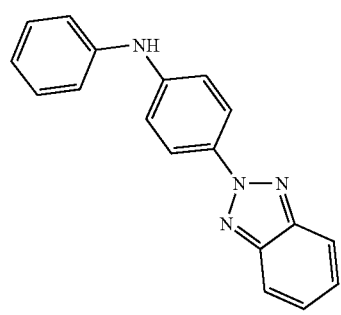
Sub 2-15
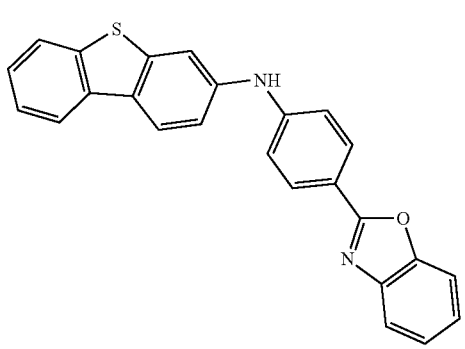
Sub 2-16
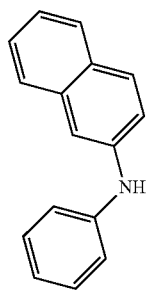
Sub 2-17
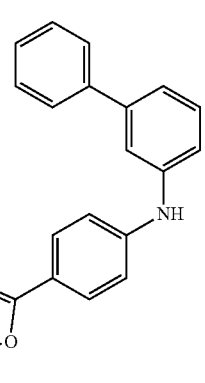
Sub 2-18
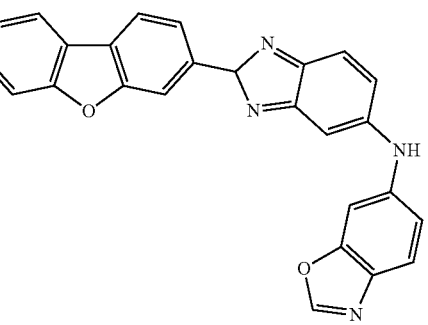
Sub 2-19
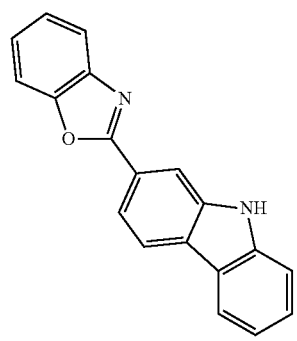
Sub 2-20
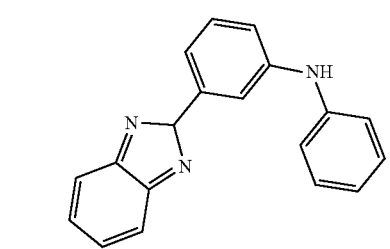

Sub 2-21
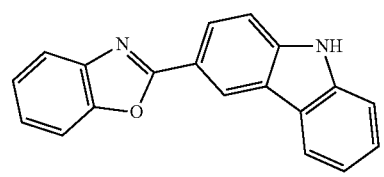
Sub 2-22
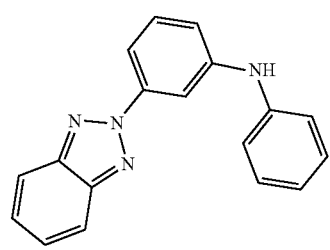
Sub 2-23
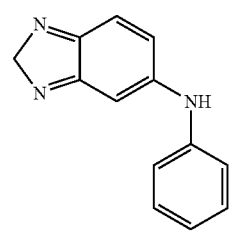
Sub 2-24
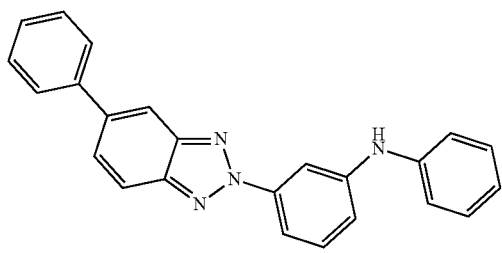
Sub 2-25
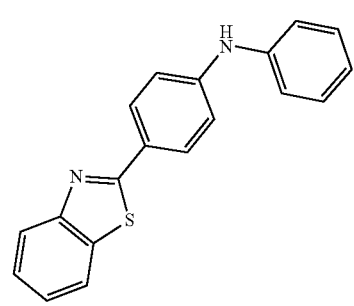
Sub 2-26
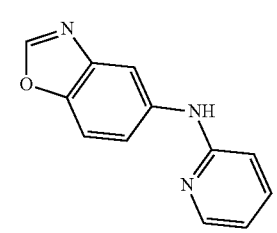
Sub 2-27
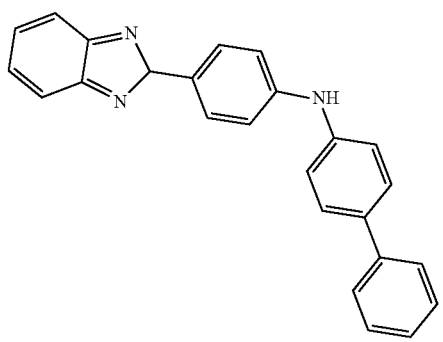
Sub 2-28
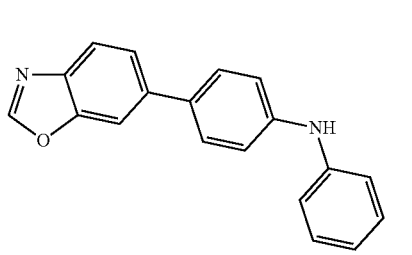
Sub 2-29
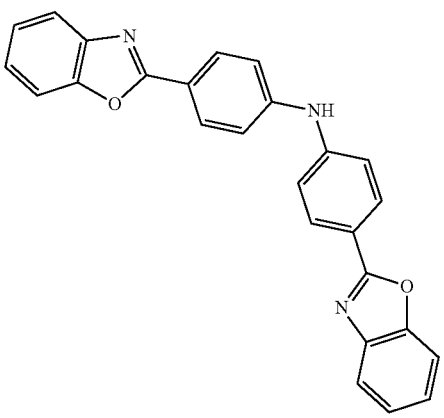
Sub 2-30
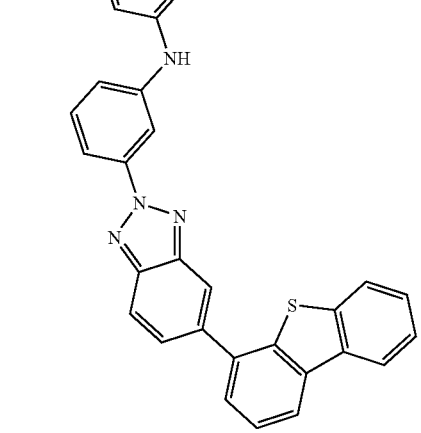

Sub 2-31
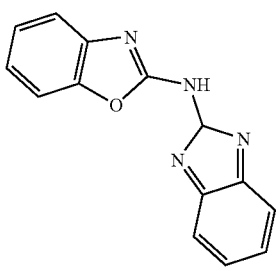
Sub 2-36
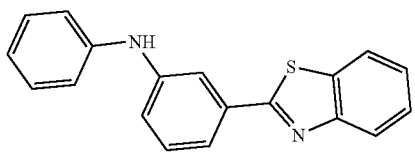
Sub 2-32
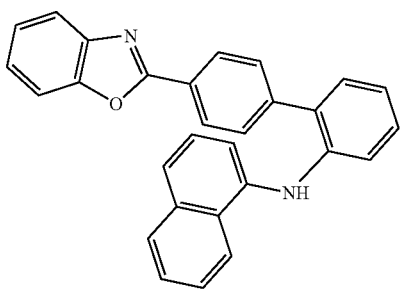
Sub 2-37
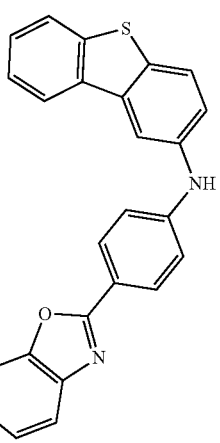
Sub 2-33
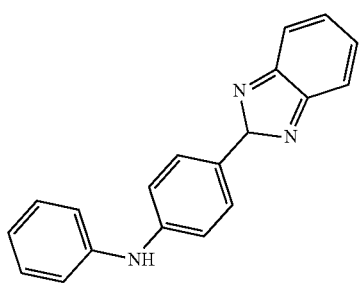
Sub 2-34
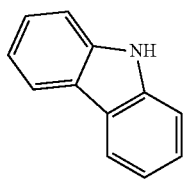
Sub 2-38
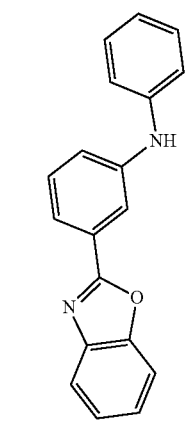
Sub 2-35
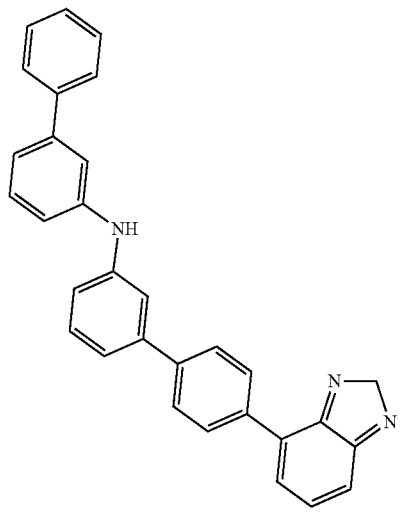
Sub 2-39
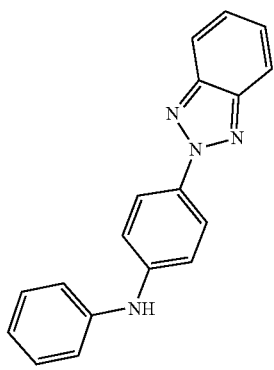

Sub 2-40
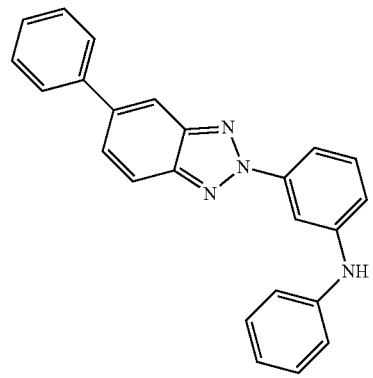

Sub 2-41
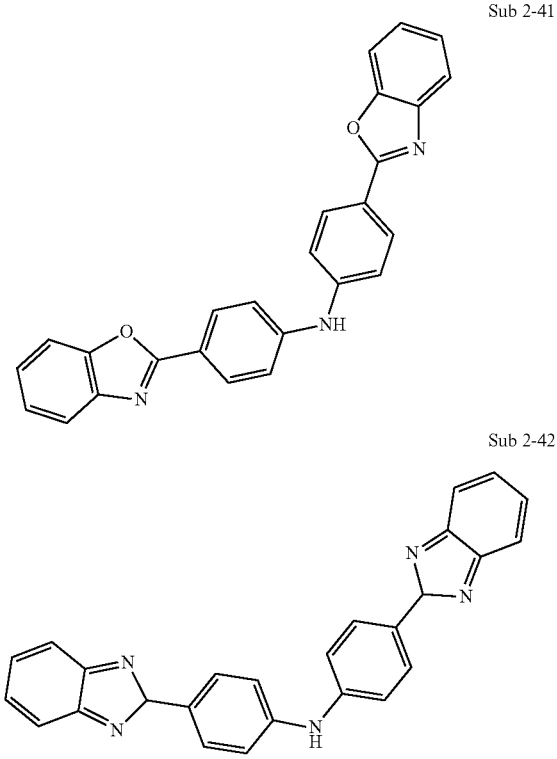

Sub 2-42

Sub 2-43
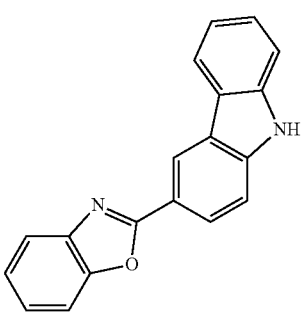

Sub 2-44
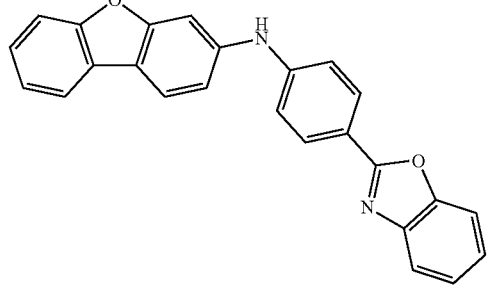

TABLE 2

| Compound | FD-MS | Compound | FD-MS |
| --- | --- | --- | --- |
| Sub 2-1 | m/z = 210.08 ($C_{13}H_{10}N_2O$ = 210.24) | Sub 2-2 | m/z = 169.09 ($C_{12}H_{11}N$ = 169.23) |
| Sub 2-3 | m/z = 275.08 ($C_{18}H_{13}NS$ = 275.37) | Sub 2-4 | m/z = 403.13 ($C_{26}H_{17}N_3O_2$ = 403.44) |
| Sub 2-5 | m/z = 251.07 ($C_{14}H_9N_3O_2$ = 251.25) | Sub 2-6 | m/z = 285.13 ($C_{19}H_{15}N_3$ = 285.35) |
| Sub 2-7 | m/z = 403.13 ($C_{26}H_{17}N_3O_2$ = 403.44) | Sub 2-8 | m/z = 286.11 ($C_{19}H_{14}N_2O$ = 286.33) |
| Sub 2-9 | m/z = 286.11 ($C_{19}H_{14}N_2O$ = 286.33) | Sub 2-10 | m/z = 226.06 ($C_{13}H_{10}N_2S$ = 226.3) |
| Sub 2-11 | m/z = 335.14 ($C_{23}H_{17}N_3$ = 335.41) | Sub 2-12 | m/z = 526.2 ($C_{38}H_{26}N_2O$ = 526.64) |
| Sub 2-13 | m/z = 260.09 ($C_{17}H_{12}N_2O$ = 260.3) | Sub 2-14 | m/z = 286.12 ($C_{18}H_{14}N_4$ = 286.34) |
| Sub 2-15 | m/z = 392.1 ($C_{25}H_{16}N_2OS$ = 392.48) | Sub 2-16 | m/z = 219.1 ($C_{16}H_{13}N$ = 219.29) |
| Sub 2-17 | m/z = 362.14 ($C_{25}H_{18}N_2O$ = 362.43) | Sub 2-18 | m/z = 416.13 ($C_{26}H_{16}N_4O_2$ = 416.44) |
| Sub 2-19 | m/z = 284.09 ($C_{19}H_{12}N_2O$ = 284.32) | Sub 2-20 | m/z = 285.13 ($C_{19}H_{15}N_3$ = 285.35) |
| Sub 2-21 | m/z = 284.09 ($C_{19}H_{12}N_2O$ = 284.32) | Sub 2-22 | m/z = 286.12 ($C_{18}H_{14}N_4$ = 286.34) |
| Sub 2-23 | m/z = 209.1 ($C_{13}H_{11}N_3$ = 209.25) | Sub 2-24 | m/z = 362.15 ($C_{24}H_{18}N_4$ = 362.44) |
| Sub 2-25 | m/z = 302.09 ($C_{19}H_{14}N_2S$ = 302.4) | Sub 2-26 | m/z = 211.07 ($C_{12}H_9N_3O$ = 211.22) |
| Sub 2-27 | m/z = 361.16 ($C_{25}H_{19}N_3$ = 361.45) | Sub 2-28 | m/z = 286.11 ($C_{19}H_{14}N_2O$ = 286.33) |
| Sub 2-29 | m/z = 403.13 ($C_{26}H_{17}N_3O_2$ = 403.44) | Sub 2-30 | m/z = 620.2 ($C_{42}H_{28}N_4S$ = 620.77) |
| Sub 2-31 | m/z = 250.09 ($C_{14}H_{10}N_4O$ = 250.26) | Sub 2-32 | m/z = 412.16 ($C_{29}H_{20}N_2O$ = 412.49) |
| Sub 2-33 | m/z = 285.13 ($C_{19}H_{15}N_3$ = 285.35) | Sub 2-34 | m/z = 167.07 ($C_{12}H_9N$ = 167.21) |
| Sub 2-35 | m/z = 437.19 ($C_{31}H_{23}N_3$ = 437.55) | Sub 2-36 | m/z = 302.09 ($C_{19}H_{14}N_2S$ = 302.4) |
| Sub 2-37 | m/z = 392.1 ($C_{25}H_{16}N_2OS$ = 392.48) | Sub 2-38 | m/z = 286.11 ($C_{19}H_{14}N_2O$ = 286.33) |
| Sub 2-39 | m/z = 286.12 ($C_{18}H_{14}N_4$ = 286.34) | Sub 2-40 | m/z = 362.15 ($C_{24}H_{18}N_4$ = 362.44) |

TABLE 2-continued

| Compound | FD-MS | Compound | FD-MS |
|---|---|---|---|
| Sub 2-41 | m/z = 403.13 ($C_{26}H_{17}N_3O_2$ = 403.44) | Sub 2-42 | m/z = 401.16 ($C_{26}H_{19}N_5$ = 401.47) |
| Sub 2-43 | m/z = 284.09 ($C_{19}H_{12}N_2O$ = 284.32) | Sub 2-44 | m/z = 376.12 ($C_{25}H_{16}N_2O_2$ = 376.42) |

III. Synthesis Examples of Final Products

1. Synthesis Example of P-2

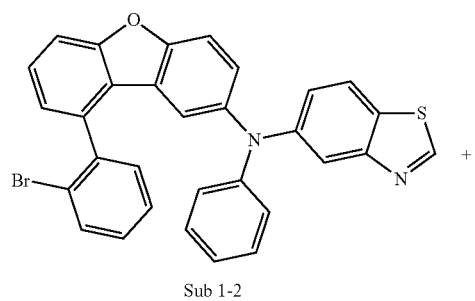

Sub 1-2

2. Synthesis Example of P-12

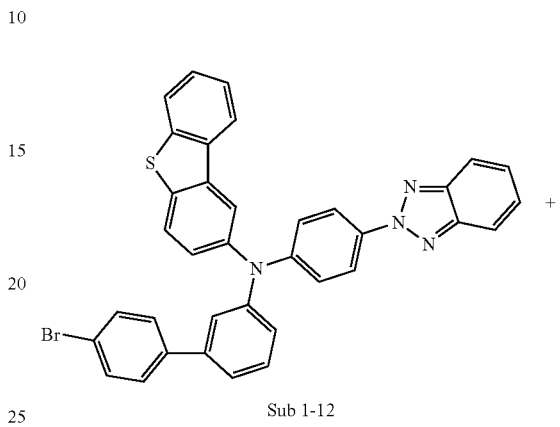

Sub 1-12

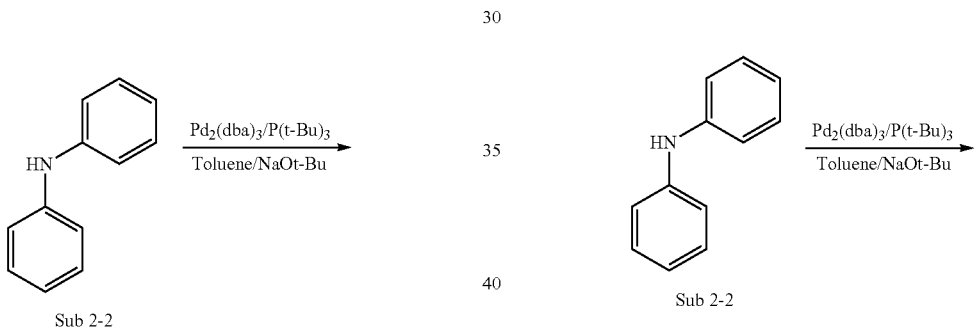

Sub 2-2

Sub 2-2

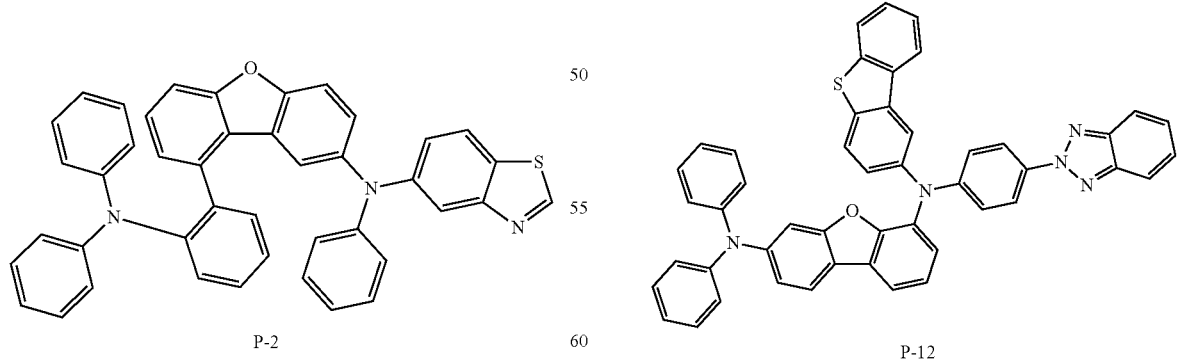

P-2

P-12

Sub 1-2 (45.1 g, 82.4 mmol), Sub 2-2 (13.9 g, 82.4 mmol), Pd$_2$(dba)$_3$ (2.3 g, 2.5 mmol), P(t-Bu)$_3$ (1.0 g, 4.9 mmol), NaOt-Bu (15.8 g, 164.8 mmol), and toluene (412 mL) in a round bottom flask were used in the same manner as in Sub 2-2 to obtain 35.6 g of the product. (Yield: 68%)

Sub 1-12 (52.8 g, 84.7 mmol), Sub 2-2 (14.3 g, 84.7 mmol), Pd$_2$(dba)$_3$ (2.3 g, 2.5 mmol), P(t-Bu)$_3$ (1.0 g, 5.1 mmol), NaOt-Bu (16.3 g, 169.3 mmol), and toluene (423 mL) in a round bottom flask were used in the same manner as in Sub 2-2 to obtain 47.3 g of the product. (Yield: 77%)

3. Synthesis Example of P-41

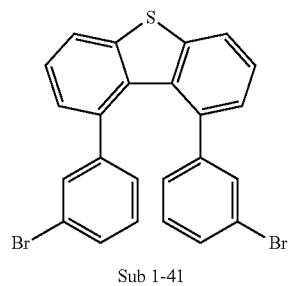

Sub 1-41

+

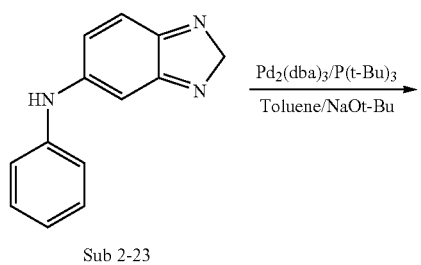

Sub 2-23

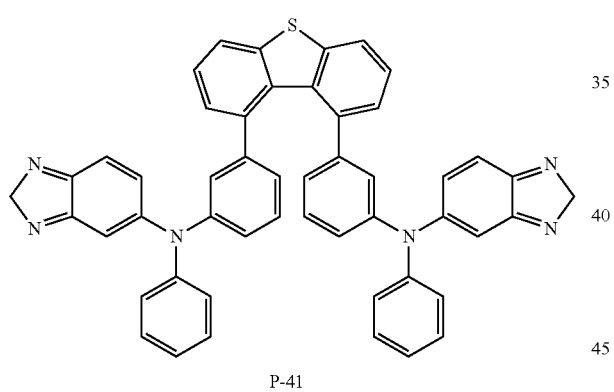

P-41

Sub 1-41 (50.0 g, 101.2 mmol), Sub 2-23 (42.3 g, 202.3 mmol), Pd₂(dba)₃ (2.8 g, 3.0 mmol), P(t-Bu)₃ (1.2 g, 6.1 mmol), NaOt-Bu (19.4 g, 202.3 mmol), and toluene (506 mL) in a round-bottom flask were used in the same manner as in Sub 2-2 to obtain 53.9 g of the product. (Yield: 71%)

4. Synthesis Example of P-63

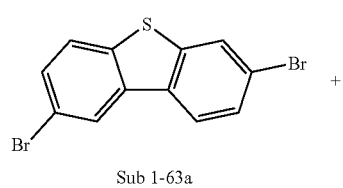

Sub 1-63a

+

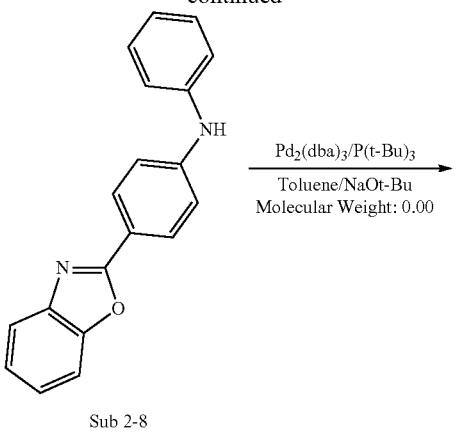

Sub 2-8

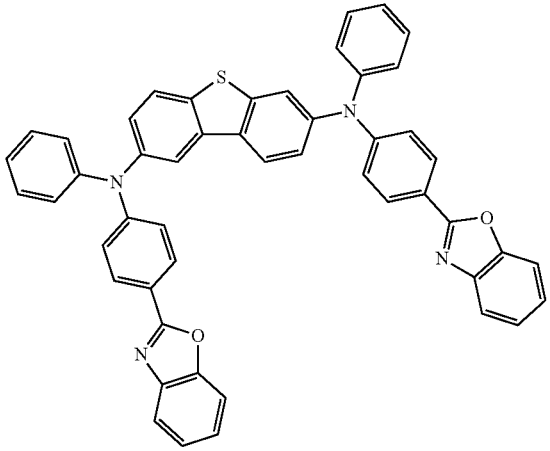

P-63

Sub 1-63a (50.0 g, 146.2 mmol), Sub 2-8 (83.7 g, 292.4 mmol), Pd₂(dba)₃ (4.0 g, 4.4 mmol), P(t-Bu)₃ (1.8 g, 8.8 mmol), NaOt-Bu (28.1 g, 292.4 mmol), and toluene (731 mL) in a round-bottom flask were used in the same manner as in Sub 2-2 to obtain 86.9 g of a product. (Yield: 79%)

5. Synthesis Example of P-67

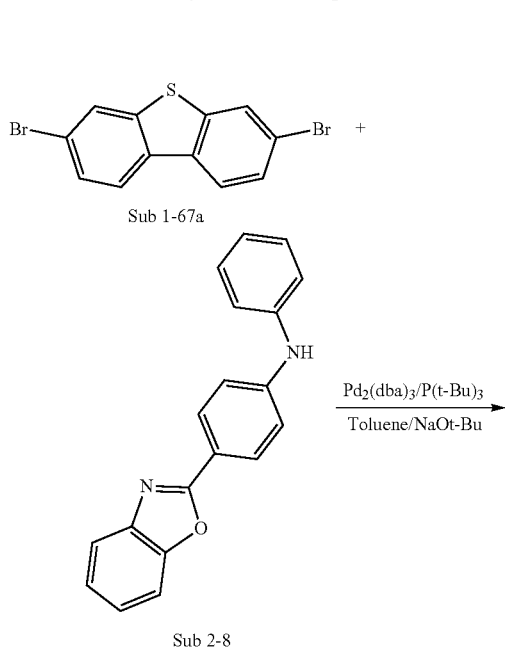

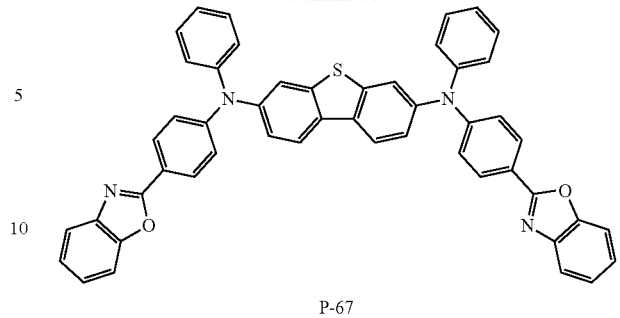

Sub 1-67a (50.0 g, 146.2 mmol), Sub 2-8 (83.7 g, 292.4 mmol), Pd$_2$(dba)$_3$ (4.0 g, 4.4 mmol), P(t-Bu)$_3$ (1.8 g, 8.8 mmol), NaOt-Bu (28.1 g, 292.4 mmol), and toluene (731 mL) in a round bottom flask were used in the same manner as in Sub 2-2, to obtain 88.0 g of a product. (Yield: 80%)

In addition, the FD-MS values of the compounds P-1 to P-88 according to the present disclosure fabricated according to the above-described synthesis examples are represented in Table 3.

TABLE 3

| Compound | FD-MS | Compound | FD-MS |
|---|---|---|---|
| P-1 | m/z = 695.26 (C$_{49}$H$_{33}$N$_3$O$_2$ = 695.82) | P-2 | m/z = 635.2 (C$_{43}$H$_{29}$N$_3$OS = 635.79) |
| P-3 | m/z = 669.24 (C$_{47}$H$_{31}$N$_3$O$_2$ = 669.78) | P-4 | m/z = 876.27 (C$_{60}$H$_{36}$N$_4$O$_4$ = 876.97) |
| P-5 | m/z = 736.25 (C$_{50}$H$_{32}$N$_4$O$_3$ = 736.83) | P-6 | m/z = 858.21 (C$_{56}$H$_{34}$N$_4$O$_2$S$_2$ = 859.03) |
| P-7 | m/z = 964.34 (C$_{68}$H$_{44}$N$_4$O$_3$ = 965.13) | P-8 | m/z = 742.2 (C$_{46}$H$_{26}$N$_6$O$_5$ = 742.75) |
| P-9 | m/z = 696.26 (C$_{47}$H$_{32}$N$_6$O = 696.81) | P-10 | m/z = 929.31 (C$_{62}$H$_{39}$N$_7$O$_3$ = 930.04) |
| P-11 | m/z = 736.25 (C$_{50}$H$_{32}$N$_4$O$_3$ = 736.83) | P-12 | m/z = 725.22 (C$_{48}$H$_{31}$N$_5$OS = 725.87) |
| P-13 | m/z = 752.22 (C$_{50}$H$_{32}$N$_4$O$_2$S = 752.89) | P-14 | m/z = 809.3 (C$_{58}$H$_{39}$N$_3$O$_2$ = 809.97) |
| P-15 | m/z = 771.29 (C$_{55}$H$_{37}$N$_3$O$_2$ = 771.92) | P-16 | m/z = 888.31 (C$_{62}$H$_{40}$N$_4$O$_3$ = 889.03) |
| P-17 | m/z = 685.22 (C$_{47}$H$_{31}$N$_3$OS = 685.85) | P-18 | m/z = 786.26 (C$_{54}$H$_{34}$N$_4$O$_3$ = 786.89) |
| P-19 | m/z = 951.3 (C$_{66}$H$_{41}$N$_5$OS = 952.15) | P-20 | m/z = 959.35 (C$_{70}$H$_{45}$N$_3$O$_2$ = 960.15) |
| P-21 | m/z = 749.21 (C$_{51}$H$_{31}$N$_3$O$_2$S = 749.89) | P-22 | m/z = 936.35 (C$_{67}$H$_{44}$N$_4$O$_2$ = 937.12) |
| P-23 | m/z = 957.35 (C$_{69}$H$_{43}$N$_5$O = 958.14) | P-24 | m/z = 998.24 (C$_{66}$H$_{38}$N$_4$O$_3$S$_2$ = 999.18) |
| P-25 | m/z = 761.25 (C$_{53}$H$_{35}$N$_3$OS = 761.94) | P-26 | m/z = 847.33 (C$_{60}$H$_{41}$N$_5$O = 848.02) |
| P-27 | m/z = 819.29 (C$_{59}$H$_{37}$N$_3$O$_2$ = 819.96) | P-28 | m/z = 844.32 (C$_{61}$H$_{40}$N$_4$O = 845.02) |
| P-29 | m/z = 894.25 (C$_{60}$H$_{38}$N$_4$OS$_2$ = 895.11) | P-30 | m/z = 668.26 (C$_{47}$H$_{32}$N$_4$O = 668.8) |
| P-31 | m/z = 1014.36 (C$_{72}$H$_{46}$N$_4$O$_3$ = 1015.19) | P-32 | m/z = 1023.27 (C$_{65}$H$_{37}$N$_9$O$_3$S = 1024.13) |
| P-33 | m/z = 973.31 (C$_{68}$H$_{39}$N$_5$O$_3$ = 974.09) | P-34 | m/z = 736.27 (C$_{48}$H$_{32}$N$_8$O = 736.84) |
| P-35 | m/z = 869.25 (C$_{57}$H$_{35}$N$_5$O$_3$S = 870) | P-36 | m/z = 886.34 (C$_{62}$H$_{42}$N$_6$O = 887.06) |
| P-37 | m/z = 924.31 (C$_{65}$H$_{40}$N$_4$O$_3$ = 925.06) | P-38 | m/z = 968.4 (C$_{66}$H$_{48}$N$_8$O = 969.17) |
| P-39 | m/z = 992.32 (C$_{69}$H$_{44}$N$_4$O$_2$S = 993.2) | P-40 | m/z = 1143.4 (C$_{78}$H$_{49}$N$_9$O$_2$ = 1144.31) |
| P-41 | m/z = 750.26 (C$_{50}$H$_{34}$N$_6$S = 750.92) | P-42 | m/z = 785.25 (C$_{55}$H$_{35}$N$_3$OS = 785.97) |
| P-43 | m/z = 784.18 (C$_{50}$H$_{32}$N$_4$S$_3$ = 785.01) | P-44 | m/z = 787.28 (C$_{54}$H$_{37}$N$_5$S = 787.99) |
| P-45 | m/z = 679.18 (C$_{41}$H$_{25}$N$_7$O$_2$S = 679.76) | P-46 | m/z = 902.32 (C$_{62}$H$_{42}$N$_6$S = 903.12) |
| P-47 | m/z = 633.19 (C$_{43}$H$_{27}$N$_3$OS = 633.77) | P-48 | m/z = 986.27 (C$_{64}$H$_{38}$N$_6$O$_4$S = 987.11) |
| P-49 | m/z = 827.3 (C$_{58}$H$_{41}$N$_3$OS = 828.05) | P-50 | m/z = 802.24 (C$_{54}$H$_{34}$N$_4$O$_2$S = 802.95) |
| P-51 | m/z = 1252.37 (C$_{84}$H$_{52}$N$_8$OS$_2$ = 1253.52) | P-52 | m/z = 834.25 (C$_{52}$H$_{34}$N$_8$O$_2$S = 834.96) |
| P-53 | m/z = 1232.41 (C$_{88}$H$_{56}$N$_4$O$_2$S = 1233.5) | P-54 | m/z = 751.25 (C$_{49}$H$_{33}$N$_7$S = 751.91) |
| P-55 | m/z = 976.32 (C$_{69}$H$_{44}$N$_4$OS = 977.2) | P-56 | m/z = 1206.44 (C$_{86}$H$_{58}$N$_6$S = 1207.51) |
| P-57 | m/z = 834.19 (C$_{54}$H$_{34}$N$_4$S$_3$ = 835.07) | P-58 | m/z = 685.22 (C$_{47}$H$_{31}$N$_3$OS = 685.85) |
| P-59 | m/z = 964.2 (C$_{62}$H$_{36}$N$_4$O$_2$S$_3$ = 965.18) | P-60 | m/z = 776.22 (C$_{52}$H$_{32}$N$_4$O$_2$S = 776.91) |
| P-61 | m/z = 852.26 (C$_{58}$H$_{36}$N$_4$O$_2$S = 853.01) | P-62 | m/z = 951.22 (C$_{61}$H$_{37}$N$_5$OS$_3$ = 952.18) |
| P-63 | m/z = 752.22 (C$_{50}$H$_{32}$N$_4$O$_2$S = 752.89) | P-64 | m/z = 800.27 (C$_{54}$H$_{36}$N$_6$S = 800.98) |
| P-65 | m/z = 913.32 (C$_{64}$H$_{43}$N$_5$S = 914.14) | P-66 | m/z = 735.23 (C$_{51}$H$_{33}$N$_3$OS = 735.91) |
| P-67 | m/z = 752.22 (C$_{50}$H$_{32}$N$_4$O$_2$S = 752.89) | P-68 | m/z = 928.31 (C$_{62}$H$_{40}$N$_8$S = 929.12) |
| P-69 | m/z = 878.27 (C$_{60}$H$_{38}$N$_4$O$_2$S = 879.05) | P-70 | m/z = 1152.32 (C$_{76}$H$_{44}$N$_6$O$_5$S = 1153.29) |
| P-71 | m/z = 727.21 (C$_{49}$H$_{33}$N$_3$S$_2$ = 727.94) | P-72 | m/z = 1135.41 (C$_{77}$H$_{53}$N$_9$S = 1136.39) |
| P-73 | m/z = 904.29 (C$_{62}$H$_{40}$N$_4$O$_2$ = 905.09) | P-74 | m/z = 936.24 (C$_{62}$H$_{40}$N$_4$S$_3$ = 937.21) |
| P-75 | m/z = 824.22 (C$_{56}$H$_{32}$N$_4$O$_2$S = 824.96) | P-76 | m/z = 632.2 (C$_{43}$H$_{28}$N$_4$S = 632.79) |
| P-77 | m/z = 917.28 (C$_{62}$H$_{39}$N$_5$O$_2$S = 918.09) | P-78 | m/z = 852.26 (C$_{58}$H$_{36}$N$_4$O$_2$S = 853.01) |
| P-79 | m/z = 1026.25 (C$_{68}$H$_{42}$N$_4$O$_3$ = 1027.29) | P-80 | m/z = 1084.31 (C$_{74}$H$_{44}$N$_4$O$_4$S = 1085.25) |
| P-81 | m/z = 851.27 (C$_{58}$H$_{37}$N$_5$OS = 852.03) | P-82 | m/z = 919.30 (C$_{62}$H$_{41}$N$_5$O$_2$S = 920.10) |
| P-83 | m/z = 935.28 (C$_{62}$H$_{41}$N$_5$O$_2$S = 936.16) | P-84 | m/z = 1071.36 (C$_{74}$H$_{49}$N$_5$O$_2$S = 1072.30) |

TABLE 3-continued

| Compound | FD-MS | Compound | FD-MS |
|---|---|---|---|
| P-85 | m/z = 716.27 ($C_{49}H_{28}D_5N3OS$ = 716.91) | P-86 | m/z = 770.22 ($C_{50}H_{31}FN_4O_2S$ = 770.22) |
| P-87 | m/z = 850.28 ($C_{56}H_{42}N_4OS_2$ = 851.10) | P-88 | m/z = 817.28 ($C_{56}H_{39}N_3O_2S$ = 818.01) |

Evaluation of the Fabrication of Organic Electric Element

Embodiment 1) Evaluation of the Fabrication of Blue Organic Electric Element

[Example 1] to [Example 20] Blue Organic Light Emitting Element (Capping Layer)

An organic light emitting element was fabricated by a common method using a compound of the present disclosure as an auxiliary emitting layer. First, a hole injection layer was formed by vacuum-depositing 4,4',4"-Tris[2-naphthyl(phenyl)amino]triphenylamine (hereinafter, referred to as "2-TNATA") to a thickness of 60 nm on an indium tin oxide (ITO) layer (i.e. a positively charged electrode) formed on a glass substrate, and then a hole transport layer was formed by vacuum-depositing N,N'-bis(1-naphthalenyl)-N,N'-bis-phenyl-(1,1'-biphenyl)-4,4'-diamine (hereinafter, referred to as "NPB") to a thickness of 60 nm on the hole injection layer. Subsequently, an emitting layer was formed by vacuum-depositing a host material to a thickness of 30 nm on the hole transport layer, the host material being 9,10-di(naphthalen-2-yl)anthracene doped with a dopant material BD-052X(Idemitsu kosan) at a weight ratio of 93:7. Afterwards, a hole blocking layer was formed by vacuum-depositing (1,1'-biphenyl-4-olato)bis(2-methyl-8-quinolinolato)aluminum (hereinafter, referred to as "BAlq") to a thickness of 10 nm on the emitting layer, and then an electron transport layer was formed by vacuum-depositing tris(8-quinolinolato)aluminum (hereinafter, referred to as "Alq3") and Bis(10-hydroxybenzo[h]quinolinato)beryllium (hereinafter, referred to as "$BeBq_2$") mixed in a 1:1 ratio to a thickness of 45 nm on the hole blocking layer. Thereafter, an electron injection layer was formed by depositing an alkali-metal halide LiF to a thickness of 0.2 nm, and then a negatively charged electrode was formed by depositing Al to a thickness of 150 nm. Consequently, the organic light emitting element was fabricated by forming a capping layer with a thickness of 60 nm on the compounds of the present disclosure represented by the Formula 1 as shown in Table 4.

Comparative Example 1

An organic light emitting elements was fabricated in the same manner as in the Example 1 except for not using the capping layer.

Comparative Examples 2 to 5

Organic light emitting elements were fabricated in the same manner as in the Example 1 except that Comparative Compounds 1 to 4 below were used as the capping layer material in place of the compounds according to the present disclosure represented by the Formula 1.

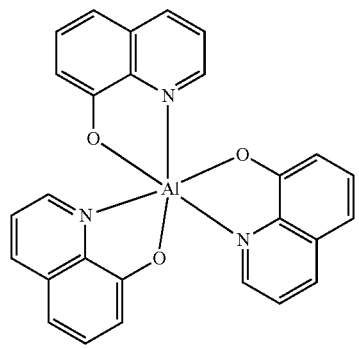

Comparative Compound 1

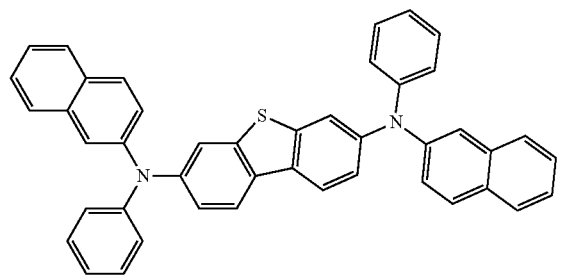

Comparative Compound 2

-continued

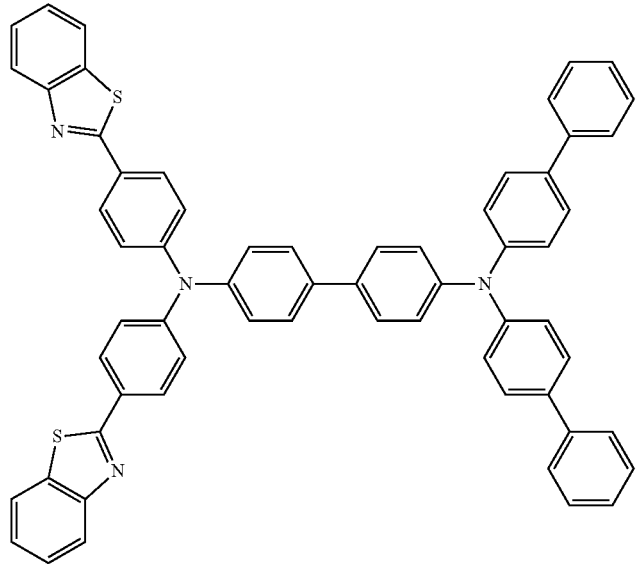

Comparative Compound 3

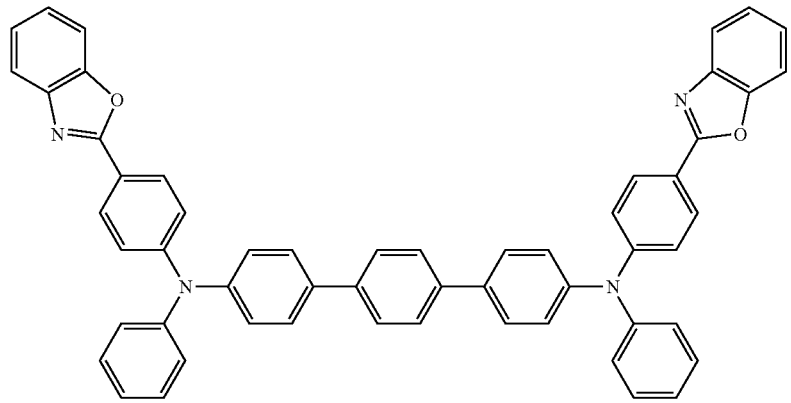

Comparative Compound 4

The electroluminescence (EL) properties of the organic light emitting elements, fabricated according to Examples 1 to 20 according to the present disclosure and the Comparative Examples 1 to 5, were measured using PR-650 available from Photo Research by applying a forward-bias DC voltage to the organic light emitting elements. The T95 lifetimes of the organic light emitting elements fabricated were measured at a reference luminance of 500 cd/m² using lifetime measuring equipment fabricated by McScience. The results of the measurement are illustrated in Table 4 below.

TABLE 4

| | Compound | Driving Voltage (V) | Current Density (mA/cm²) | Brightness (cd/m²) | Efficiency (cd/A) | Lifetime T95 (hr) | CIE x | CIE y |
|---|---|---|---|---|---|---|---|---|
| Comparative Example 1 | — | 6.5 | 22.7 | 500 | 2.2 | 60.3 | 0.15 | 0.15 |
| Comparative Example 2 | Comparative Compound 1 | 6.4 | 20.0 | 500 | 2.5 | 61.8 | 0.15 | 0.10 |
| Comparative Example 3 | Comparative Compound 2 | 6.5 | 16.1 | 500 | 3.1 | 62.3 | 0.14 | 0.09 |
| Comparative Example 4 | Comparative Compound 3 | 6.5 | 15.6 | 500 | 3.2 | 63.1 | 0.15 | 0.09 |
| Comparative Example 5 | Comparative Compound 4 | 6.4 | 14.7 | 500 | 3.4 | 63.7 | 0.15 | 0.08 |
| Example 1 | P-2 | 6.5 | 11.4 | 500 | 4.4 | 62.7 | 0.14 | 0.07 |
| Example 2 | P-11 | 6.4 | 10.7 | 500 | 4.7 | 63.0 | 0.14 | 0.07 |
| Example 3 | P-12 | 6.5 | 11.3 | 500 | 4.4 | 62.9 | 0.14 | 0.07 |
| Example 4 | P-13 | 6.4 | 10.9 | 500 | 4.6 | 63.4 | 0.14 | 0.07 |
| Example 5 | P-16 | 6.4 | 11.2 | 500 | 4.5 | 62.9 | 0.14 | 0.07 |
| Example 6 | P-22 | 6.5 | 11.4 | 500 | 4.4 | 62.2 | 0.14 | 0.07 |

TABLE 4-continued

| | Compound | Driving Voltage (V) | Current Density (mA/cm$^2$) | Brightness (cd/m$^2$) | Efficiency (cd/A) | Lifetime T95 (hr) | CIE x | CIE y |
|---|---|---|---|---|---|---|---|---|
| Example 7 | P-24 | 6.4 | 11.2 | 500 | 4.5 | 63.8 | 0.14 | 0.07 |
| Example 8 | P-26 | 6.4 | 10.7 | 500 | 4.7 | 62.6 | 0.14 | 0.07 |
| Example 9 | P-34 | 6.5 | 11.0 | 500 | 4.5 | 63.8 | 0.14 | 0.07 |
| Example 10 | P-36 | 6.4 | 10.9 | 500 | 4.6 | 62.6 | 0.14 | 0.07 |
| Example 11 | P-41 | 6.4 | 10.7 | 500 | 4.7 | 62.1 | 0.14 | 0.07 |
| Example 12 | P-42 | 6.4 | 10.8 | 500 | 4.6 | 63.9 | 0.14 | 0.07 |
| Example 13 | P-43 | 6.4 | 10.7 | 500 | 4.7 | 63.6 | 0.14 | 0.07 |
| Example 14 | P-44 | 6.5 | 11.6 | 500 | 4.3 | 64.0 | 0.14 | 0.07 |
| Example 15 | P-45 | 6.4 | 11.6 | 500 | 4.3 | 63.6 | 0.14 | 0.07 |
| Example 16 | P-60 | 6.4 | 11.5 | 500 | 4.3 | 63.3 | 0.14 | 0.07 |
| Example 17 | P-63 | 6.4 | 10.4 | 500 | 4.8 | 63.1 | 0.14 | 0.07 |
| Example 18 | P-66 | 6.4 | 11.5 | 500 | 4.4 | 63.5 | 0.14 | 0.07 |
| Example 19 | P-67 | 6.4 | 10.2 | 500 | 4.9 | 63.9 | 0.14 | 0.07 |
| Example 20 | P-76 | 6.4 | 11.5 | 500 | 4.3 | 63.2 | 0.14 | 0.07 |

Embodiment 2) Evaluation of the Fabrication of Green Organic Electric Element

[Example 21] to [Example 40] Green Organic Light Emitting Element (Capping Layer)

Organic light emitting elements were fabricated in the same manner as in the Example 1 except that CBP[4,4'-N,N'-dicarbazole-biphenyl] instead of 9,10-di(naphthalen-2-yl)anthracene as a host, and tris(2-phenylpyridine)-iridium instead of BD-052X(Idemitsu kosan) as a dopant was used in a weight ratio of 95:5.

Comparative Example 6

An organic light emitting elements was fabricated in the same manner as in the Example 21 except for not using the capping layer.

Comparative Examples 7 to 10

Organic light emitting elements were fabricated in the same manner as in the Example 21 except that the Comparative Compounds 1 to 4 were used as the capping layer material in place of the compounds according to the present disclosure represented by the Formula 1.

The electroluminescence (EL) properties of the organic light emitting elements, fabricated according to Examples 21 to 40 according to the present disclosure and the Comparative Examples 6 to 10, were measured using PR-650 available from Photo Research by applying a forward-bias DC voltage to the organic light emitting elements. The T95 lifetimes of the organic light emitting elements fabricated were measured at a reference luminance of 5000 cd/m$^2$ using lifetime measuring equipment fabricated by McScience. The results of the measurement are illustrated in Table 5 below.

TABLE 5

| | Compound | Driving Voltage (V) | Current Density (mA/cm$^2$) | Brightness (cd/m$^2$) | Efficiency (cd/A) | Lifetime T95 (hr) | CIE x | CIE y |
|---|---|---|---|---|---|---|---|---|
| Comparative Example 6 | — | 6.4 | 23.1 | 5000 | 21.6 | 69.6 | 0.34 | 0.61 |
| Comparative Example 7 | Comparative Compound 1 | 6.3 | 17.4 | 5000 | 28.8 | 70.2 | 0.35 | 0.62 |
| Comparative Example 8 | Comparative Compound 2 | 6.3 | 15.5 | 5000 | 32.3 | 70.2 | 0.34 | 0.68 |
| Comparative Example 9 | Comparative Compound 3 | 6.4 | 14.5 | 5000 | 34.4 | 70.1 | 0.35 | 0.67 |
| Comparative Example 10 | Comparative Compound 4 | 6.4 | 14.4 | 5000 | 34.7 | 70.3 | 0.36 | 0.66 |
| Example 21 | P-2 | 6.3 | 11.6 | 5000 | 43.1 | 70.8 | 0.33 | 0.65 |
| Example 22 | P-11 | 6.4 | 10.9 | 5000 | 45.9 | 70.1 | 0.33 | 0.65 |
| Example 23 | P-12 | 6.3 | 11.5 | 5000 | 43.3 | 70.9 | 0.33 | 0.65 |
| Example 24 | P-13 | 6.4 | 11.1 | 5000 | 44.9 | 70.8 | 0.33 | 0.65 |
| Example 25 | P-16 | 6.3 | 11.4 | 5000 | 44.0 | 70.4 | 0.33 | 0.64 |
| Example 26 | P-22 | 6.4 | 11.5 | 5000 | 43.5 | 70.3 | 0.33 | 0.65 |
| Example 27 | P-24 | 6.4 | 11.3 | 5000 | 44.3 | 70.5 | 0.33 | 0.64 |
| Example 28 | P-26 | 6.3 | 10.8 | 5000 | 46.4 | 70.4 | 0.33 | 0.64 |
| Example 29 | P-34 | 6.3 | 11.3 | 5000 | 44.4 | 70.7 | 0.33 | 0.65 |
| Example 30 | P-36 | 6.3 | 11.1 | 5000 | 45.2 | 70.9 | 0.33 | 0.65 |
| Example 31 | P-41 | 6.3 | 10.9 | 5000 | 46.0 | 70.2 | 0.33 | 0.64 |
| Example 32 | P-42 | 6.3 | 10.9 | 5000 | 45.7 | 70.8 | 0.33 | 0.64 |
| Example 33 | P-43 | 6.3 | 10.7 | 5000 | 46.6 | 70.0 | 0.33 | 0.64 |
| Example 34 | P-44 | 6.4 | 11.9 | 5000 | 42.1 | 70.7 | 0.33 | 0.64 |
| Example 35 | P-45 | 6.3 | 11.8 | 5000 | 42.4 | 70.8 | 0.33 | 0.65 |
| Example 36 | P-60 | 6.4 | 11.8 | 5000 | 42.5 | 70.6 | 0.33 | 0.64 |
| Example 37 | P-63 | 6.4 | 10.5 | 5000 | 47.6 | 70.1 | 0.33 | 0.65 |

TABLE 5-continued

| | Compound | Driving Voltage (V) | Current Density (mA/cm$^2$) | Brightness (cd/m$^2$) | Efficiency (cd/A) | Lifetime T95 (hr) | CIE x | CIE y |
|---|---|---|---|---|---|---|---|---|
| Example 38 | P-66 | 6.4 | 11.4 | 5000 | 43.7 | 70.9 | 0.33 | 0.64 |
| Example 39 | P-67 | 6.4 | 10.5 | 5000 | 47.6 | 70.1 | 0.33 | 0.65 |
| Example 40 | P-76 | 5.3 | 11.7 | 5000 | 42.6 | 70.5 | 0.33 | 0.64 |

Embodiment 3) Evaluation of the Fabrication of Red Organic Electric Element

[Example 41] to [Example 60] Red Organic Light Emitting Element (Capping Layer)

Organic light emitting elements were fabricated in the same manner as in the Example 1 except that CBP[4,4'-N, N'-dicarbazole-biphenyl] instead of 9,10-di(naphthalen-2-yl)anthracene as a host, and (Piq)$_2$Ir(acac) [bis-(1-phenylisoquinolyl)iridium(III)acetylacetonate] instead of BD-052X (Idemitsu kosan) as a dopant was used in a weight ratio of 95:5.

Comparative Example 11

An organic light emitting elements was fabricated in the same manner as in the Example 41 except for not using the capping layer.

Comparative Examples 12 to 15

Organic light emitting elements were fabricated in the same manner as in the Example 41 except that the Comparative Compounds 1 to 4 were used as the capping layer material in place of the compounds according to the present disclosure represented by the Formula 1.

The electroluminescence (EL) properties of the organic light emitting elements, fabricated according to Examples 41 to 60 according to the present disclosure and the Comparative Examples 11 to 15, were measured using PR-650 available from Photo Research by applying a forward-bias DC voltage to the organic light emitting elements. The T95 lifetimes of the organic light emitting elements fabricated were measured at a reference luminance of 2500 cd/m$^2$ using lifetime measuring equipment fabricated by McScience. The results of the measurement are illustrated in Table 6 below.

TABLE 6

| | Compound | Driving Voltage (V) | Current Density (mA/cm$^2$) | Brightness (cd/m$^2$) | Efficiency (cd/A) | Lifetime T95 (hr) | CIE x | CIE y |
|---|---|---|---|---|---|---|---|---|
| Comparative Example 11 | — | 6.6 | 32.9 | 2500 | 7.6 | 57.2 | 0.62 | 0.39 |
| Comparative Example 12 | Comparative Compound 1 | 6.5 | 30.9 | 2500 | 8.1 | 58.0 | 0.63 | 0.32 |
| Comparative Example 13 | Comparative Compound 2 | 6.6 | 26.9 | 2500 | 9.3 | 62.4 | 0.64 | 0.34 |
| Comparative Example 14 | Comparative Compound 3 | 6.6 | 26.9 | 2500 | 9.3 | 62.1 | 0.63 | 0.39 |
| Comparative Example 15 | Comparative Compound 4 | 6.5 | 26.6 | 2500 | 9.4 | 62.2 | 0.63 | 0.38 |
| Example 41 | P-2 | 6.5 | 20.5 | 2500 | 12.2 | 62.2 | 0.67 | 0.34 |
| Example 42 | P-11 | 6.5 | 18.1 | 2500 | 13.8 | 63.6 | 0.67 | 0.34 |
| Example 43 | P-12 | 6.6 | 20.0 | 2500 | 12.5 | 63.1 | 0.67 | 0.34 |
| Example 44 | P-13 | 6.5 | 18.2 | 2500 | 13.7 | 63.7 | 0.67 | 0.34 |
| Example 45 | P-16 | 6.6 | 19.1 | 2500 | 13.1 | 62.4 | 0.67 | 0.34 |
| Example 46 | P-22 | 6.6 | 19.5 | 2500 | 12.8 | 62.2 | 0.67 | 0.34 |
| Example 47 | P-24 | 6.5 | 18.8 | 2500 | 13.3 | 62.1 | 0.67 | 0.34 |
| Example 48 | P-26 | 6.5 | 17.9 | 2500 | 14.0 | 62.8 | 0.67 | 0.34 |
| Example 49 | P-34 | 6.5 | 18.4 | 2500 | 13.6 | 63.9 | 0.67 | 0.34 |
| Example 50 | P-36 | 6.5 | 18.0 | 2500 | 13.9 | 62.2 | 0.67 | 0.34 |
| Example 51 | P-41 | 6.5 | 17.7 | 2500 | 14.1 | 62.5 | 0.67 | 0.34 |
| Example 52 | P-42 | 6.5 | 17.9 | 2500 | 14.0 | 62.8 | 0.67 | 0.34 |
| Example 53 | P-43 | 6.5 | 18.4 | 2500 | 13.6 | 63.4 | 0.67 | 0.34 |
| Example 54 | P-44 | 6.6 | 21.9 | 2500 | 11.4 | 62.6 | 0.67 | 0.34 |
| Example 55 | P-45 | 6.5 | 21.4 | 2500 | 11.7 | 61.1 | 0.67 | 0.34 |
| Example 56 | P-60 | 6.5 | 21.0 | 2500 | 11.9 | 62.4 | 0.67 | 0.34 |
| Example 57 | P-63 | 6.5 | 17.6 | 2500 | 14.2 | 62.9 | 0.67 | 0.34 |
| Example 58 | P-66 | 6.5 | 19.2 | 2500 | 13.0 | 62.5 | 0.67 | 0.34 |
| Example 59 | P-67 | 6.6 | 17.2 | 2500 | 14.5 | 62.8 | 0.67 | 0.34 |
| Example 60 | P-76 | 6.5 | 20.7 | 2500 | 12.1 | 63.5 | 0.67 | 0.35 |

As seen from the results of Tables 4 to 6, it may be seen that, when the organic light-emitting elements were fabricated using the organic light emitting element material according to the present disclosure as the capping layer material represented by the Formula 1, the organic light emitting elements may have a high purity and improved luminous efficiency compared to the comparative examples. It may be seen that the color purity and luminous efficiency are increased by the introduction of the capping layer, comparing the results according to the presence or absence of the capping layer. It may be seen that when the compound according to the present disclosure is applied rather than the comparative compounds 1 to 4 as the capping layer, the luminous efficiency is significantly improved.

When the capping layer is introduced, the SPPs (Surface plasmon polaritons) are generated at the interface between the Al electrode and the high refractive organic material. In this case, the TE (transverse electric) polarized light is annihilated on the capping layer surface in the vertical direction by an evanescent wave and TM polarized light moving along the cathode and the capping layer is amplified by surface plasma resonance, thereby enabling high efficiency and effective color purity control.

As described above, in the visible light wavelength band of 430 nm to 780 nm, the compound according to the present disclosure includes, as a core, a substituent group in which a benzene ring such as benzoimidazole or benzoxazole and the five-membered ring with at least one N is fused in order to increase the refractive index and dibenzothiophene or dibenzofuran including sulfur or oxygen atom, which is a hetero element with a high refractive index, and thus has a higher refractive index than that of the comparative compound B or the comparative compound C and thus, the light generated in the organic material layer increases the efficiency of extraction to the outside of the organic light emitting element by the principle of constructive interference, thereby greatly contributing to the improvement of the light efficiency of the organic electric element.

The above description provides examples of the present disclosure for illustrative purposes only. Those having ordinary knowledge in the technical field, to which the present disclosure pertains, will appreciate that various modifications are possible without departing from the essential features of the present disclosure. Therefore, the examples disclosed in the present disclosure are intended to illustrate the technical idea of the present disclosure, and the scope of the present disclosure is not limited by the examples.

The scope of the present disclosure shall be construed on the basis of the accompanying claims in such a manner that all of the technical ideas included within the scope equivalent to the claims belong to the present disclosure.

DESCRIPTION OF SYMBOLS 100, 200, 300: organic electric element
110, 110, 310: first electrode
20, 220, 320: hole injection layer
321: first hole injection layer
130, 230: hole transport layer
331: first hole transport layer
332: second hole transport layer
243: buffer layer
253: light emitting auxiliary layer
140, 240: light emitting layer
341: first light emitting layer
342: second emitting layer
150, 250: electron transport layer
351: first electron transport layer
352: second electron transport layer
160, 260, 360: electron injection layer
170, 270, 370: second electrode
180, 280, 380: capping layer
390: first charge generating layer
391: second charge generating layer
ST1: first stack
ST2: second stack
CGL: charge generating layer

The invention claimed is:

1. An organic electric element comprising:
a first electrode;
a second electrode;
an organic material layer located between the first electrode and the second electrode, and
a capping layer disposed on at least one of one surface of the first electrode opposite to the organic material layer and one surface of the second electrode opposite to the organic material layer,
wherein the capping layer comprises a compound represented by following Formula 1-T:

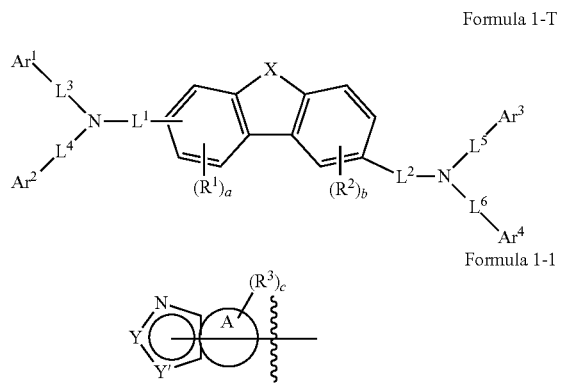

Formula 1-T

Formula 1-1 in the Formula 1-T,
1) $Ar^1$ to $Ar^4$ are each independently selected from a group consisting of a $C_6$-$C_{60}$ aryl group; a fluorenyl group; a $C_2$-$C_{60}$ hetero ring group comprising at least one heteroatom selected from among O, N, S, Si, or P; and a fused ring group of a $C_3$-$C_{60}$ aliphatic ring and a $C_6$-$C_{60}$ aromatic ring,
2) At least one of $Ar^1$ to $Ar^4$ is represented by formula 1-1,
3) $L^1$ and $L^2$ are each independently selected from a group consisting of a single bond; a $C_6$-$C_{60}$ arylene group; a fluorenylene group; a $C_2$-$C_{60}$ hetero ring group comprising at least one heteroatom selected from among 0, N, S, Si, or P; and a fused ring group of a $C_3$-$C_{60}$ aliphatic ring and a $C_6$-$C_{60}$ aromatic ring,
4) $L^3$ to $L^6$ are each independently selected from a group consisting of a single bond; a $C_6$-$C_{60}$ arylene group; a fluorenylene group; a $C_2$-$C_{60}$ hetero ring group comprising at least one heteroatom selected from among 0, N, S, Si, or P; and a fused ring group of a $C_3$-$C_{60}$ aliphatic ring and a $C_6$-$C_{60}$ aromatic,
5) $R^1$ and $R^2$ are each independently selected from the group consisting of deuterium; a $C_6$-$C_{60}$ aryl group; a fluorenyl group; a $C_2$-$C_{60}$ hetero ring group comprising at least one heteroatom selected from among 0, N, S, Si, or P; a fused ring group of a $C_3$-$C_{60}$ aliphatic ring and a $C_6$-$C_{60}$ aromatic ring; and -$L'$-$N(R^a)$ $(R^b)$, and one or more adjacent $R^1$s are the same or different and the adjacent R¹s may be bonded to each other to form a ring, and one or more adjacent R²s are the same or different and the adjacent R²s may be bonded to each other to form a ring, 6) $R^3$ is each independently selected from the group consisting of deuterium; a $C_6$-$C_{60}$ aryl group; a fluorenyl group; a $C_2$-$C_{60}$ hetero ring group comprising at least one heteroatom selected from among O, N, S, Si, or P; and a fused ring group of a $C_3$-$C_{60}$ aliphatic ring and a $C_6$-$C_{60}$ aromatic ring; and -L'-N($R^a$) ($R^b$), and one or more adjacent $R^3$s are the same or different and the adjacent $R^3$s may be bonded to each other to form a ring, 7) A and b are each independently an integer of 0 to 3, c is an integer of 0 to 4, and when two or more of $Ar^1$ to $Ar^4$ are represented by the formula 1-1, a plurality of c's are the same or may be different, 8) L' is each independently selected from a group consisting of a single bond; $C_6$-$C_{60}$ arylene group; fluorenylene group; a $C_2$-$C_{60}$ hetero ring group comprising at least one heteroatom selected from among O, N, S, Si, or P; and a fused ring group of a $C_3$-$C_{60}$ aliphatic ring and a $C_6$-$C_{60}$ aromatic ring, 9) $R^a$ and $R^b$ are each independently selected from a group consisting of a $C_6$-$C_{60}$ aryl group; a fluorenyl group; a $C_2$-$C_{60}$ hetero ring group comprising at least one heteroatom selected from among O, N, S, Si, or P; and a fused ring group of a $C_3$-$C_{60}$ aliphatic ring and a $C_6$-$C_{60}$ aromatic ring, 10) X is O or S, 11) Ring A is each independently selected from the group consisting of benzene, naphthalene, phenanthrene and anthracene, 12) Y is each independently $CR^aR^b$ or $NR^c$, and when Y is bonded to the formula 1-T, it may be N or C;

13) Y' is each independently N, O or S,

14) $R^a$, $R^b$ and $R^c$ are each independently hydrogen; deuterium; a $C_6$-$C_{60}$ aryl group; a fluorenyl group; a $C_2$-$C_{60}$ hetero ring group comprising at least one heteroatom selected from among O, N, S, Si, or P; and a fused ring group of a $C_3$-$C_{60}$ aliphatic ring and a $C_6$-$C_{60}$ aromatic ring, 15) Adjacent $L^1$ and $R^1$, $L^1$ and $Ar^1$, $L^1$ and $Ar^2$, $L^1$ and $L^3$, and $L^4$, adjacent $L^2$ and $R^2$, $L^2$ and Ara, $L^2$ and $Ar^4$, $L^2$ and $L^5$, $L^2$ and $L^6$ may be bonded to form a ring, 16) In $Ar^1$ to $Ar^4$, $L^1$ to $L^6$, $R^1$ to $R^3$, $R^a$ and $R^b$, each of the aryl group, the fluorenyl group, the hetero ring group, the fused ring group, the arylene group and the fluorenylene group is further substituted with one or more substituents selected from a group consisting of deuterium; a nitro group; a nitrile group; a halogen group; an amino group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ hetero ring group; a $C_3$-$C_{20}$ cycloalkyl group; a $C_7$-$C_{20}$ aryl alkyl group; and a $C_8$-$C_{20}$ aryl alkenyl group, the substituents are allowed to be bonded to form a ring, and each of the substituents is further substituted with one or more substituents selected from a group consisting of deuterium; a nitro group; a nitrile group; a halogen group; an amino group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ hetero ring group; a $C_3$-$C_{20}$ cycloalkyl group; a $C_7$-$C_{20}$ aryl alkyl group; and a $C_8$-$C_{20}$ aryl alkenyl group, and the substituents are allowed to be bonded to form a ring.

2. The organic electric element according to claim 1, wherein one of $Ar^1$ and $Ar^2$ is represented by formula 1-1, or one of $Ar^3$ and $Ar^4$ is represented by formula 1-1, or one of $Ar^1$ and $Ar^2$ is represented by formula 1-1, and one of $Ar^3$ and $Ar^4$ is represented by formula 1-1, or $Ar^1$ and $Ar^2$ are represented by formula 1-1, or $Ar^3$ and $Ar^4$ are represented by formula 1-1, or one of $Ar^1$ and $Ar^2$ is represented by formula 1-1, and $Ar^3$ and $Ar^4$ are represented by formula 1-1, or $Ar^1$ and $Ar^2$ are represented by formula 1-1, and one of $Ar^3$ and $Ar^4$ is represented by formula 1-1, or $Ar^1$ to $Ar^4$ are represented by formula 1-1.

3. The organic electric element according to claim 1, wherein the adjacent $R^1$s are bonded to each other to form a ring, or
the adjacent $R^2$s are bonded with each other to form a ring, or
the adjacent $R^1$s are bonded to each other to form a ring, and the adjacent $R^2$s are bonded with each other to form a ring.

4. The organic electric element according to claim 1, wherein X is O.

5. The organic electric element according to claim 1, wherein X is S.

6. The organic electric element according to claim 1, wherein one of $Ar^1$ to $Ar^4$ is represented by one of following Formulas 1-1a to 1-1e:

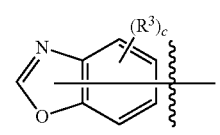

Formula 1-1a

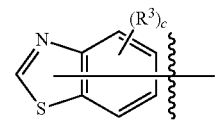

Formula 1-1b

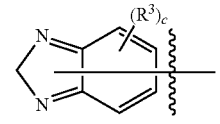

Formula 1-1c

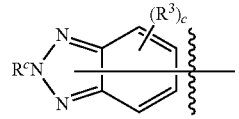

Formula 1-1d

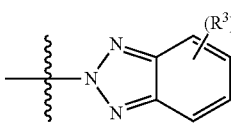

Formula 1-1e where $R^3$ and c in the Formulas 1-1a to 1-1e are the same as defined in the Formula 1-T of claim 1.

7. The organic electric element according to claim 1, wherein the compound represented by the Formula 1-T comprises one of following compounds:

131
132
P-7
P-10
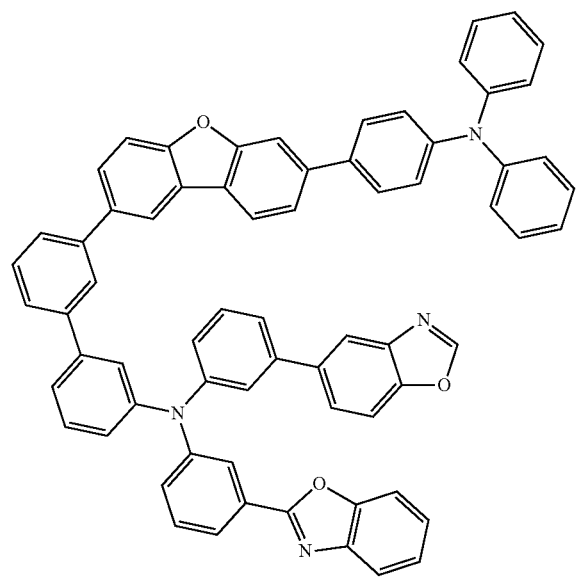
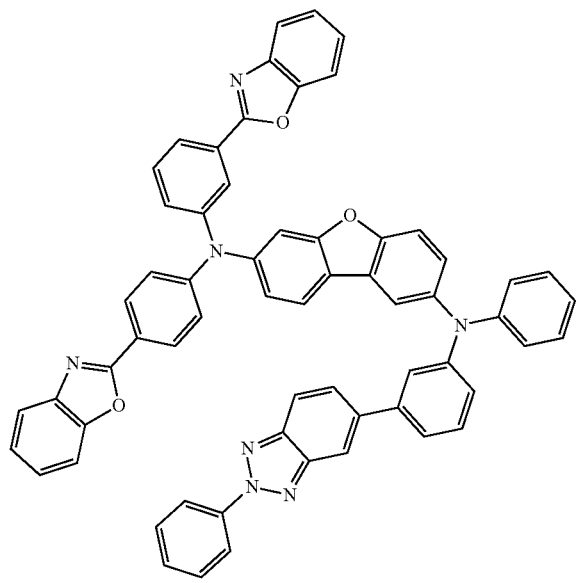
P-23
P-26
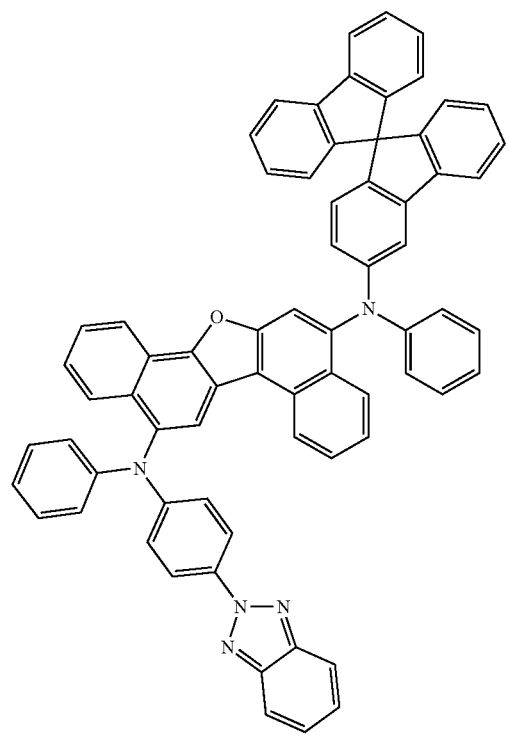
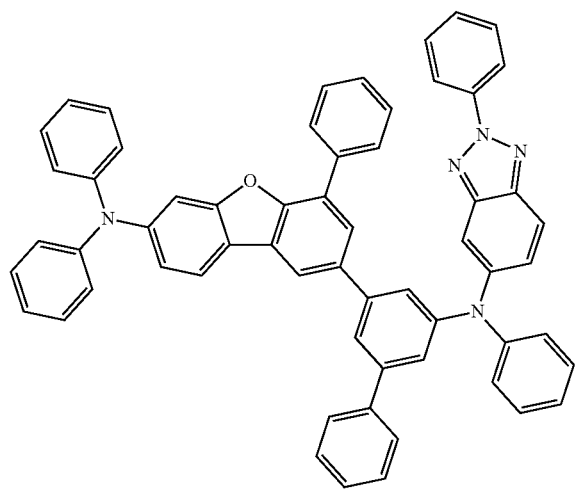

P-30
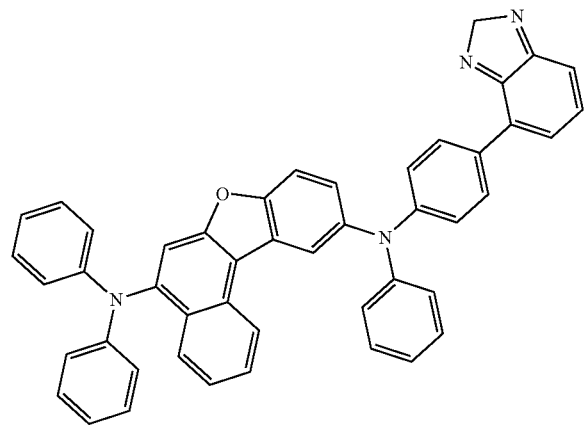
P-33
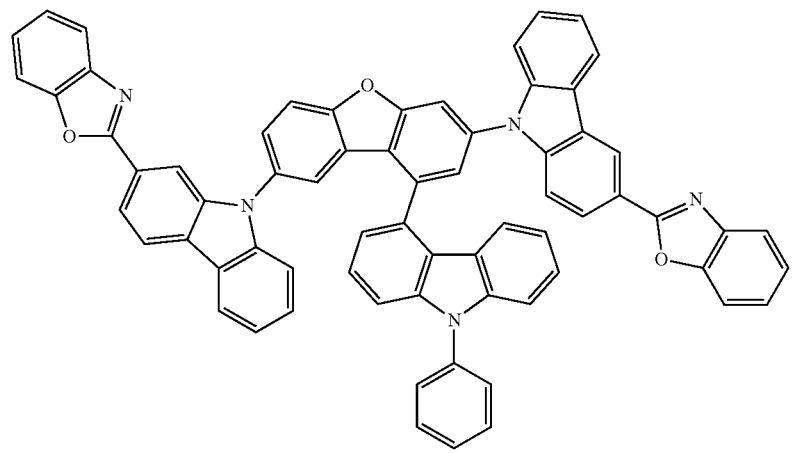
P-35
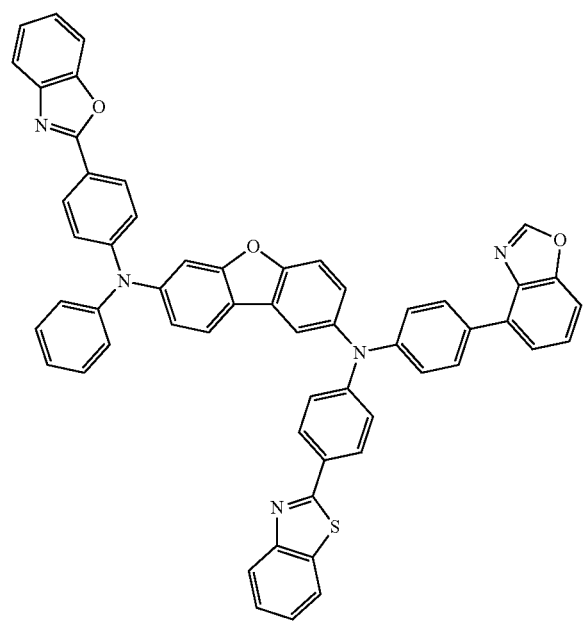
P-39
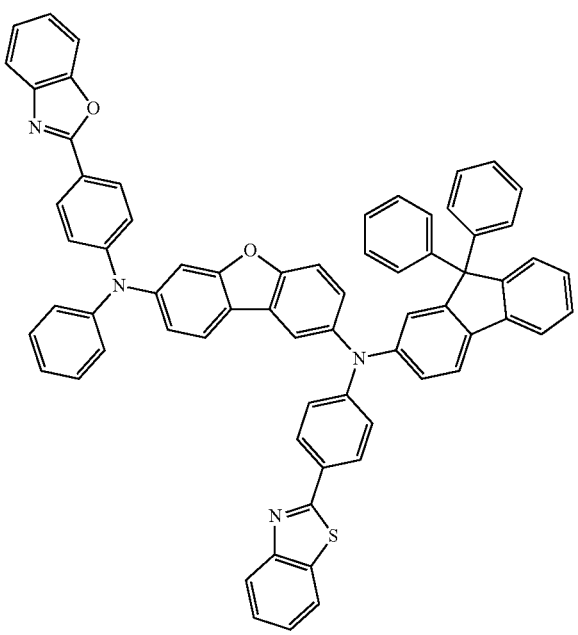

-continued
P-47
P-50
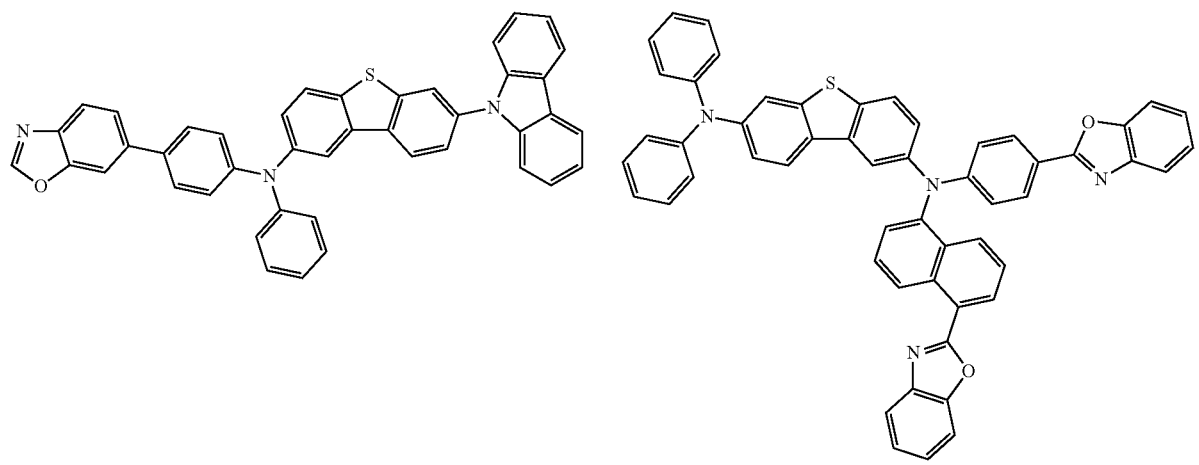
P-63
P-66
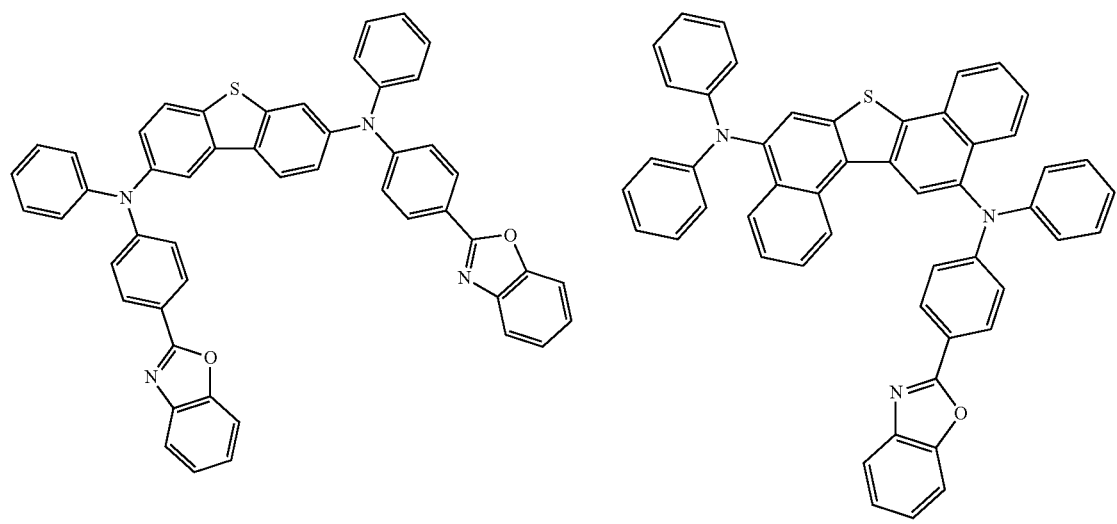
P-73
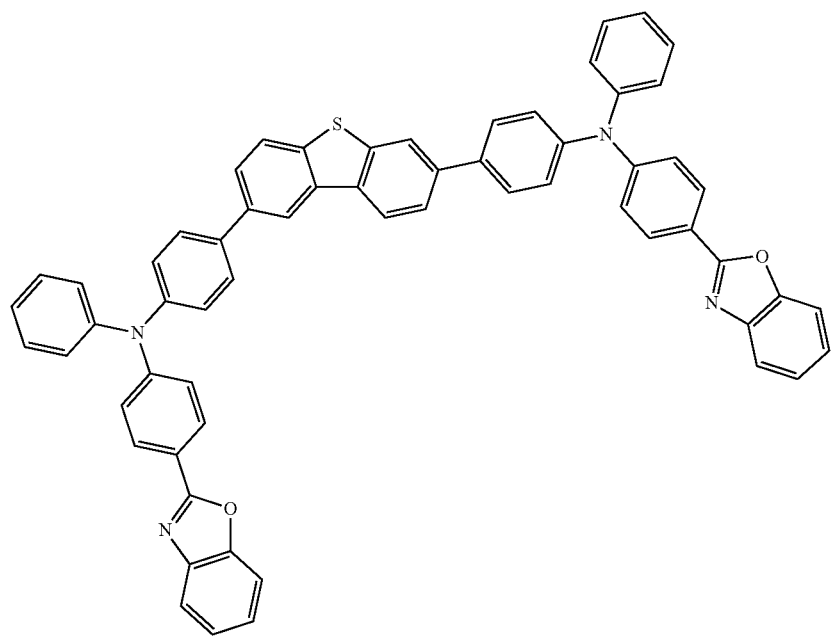

-continued
P-75
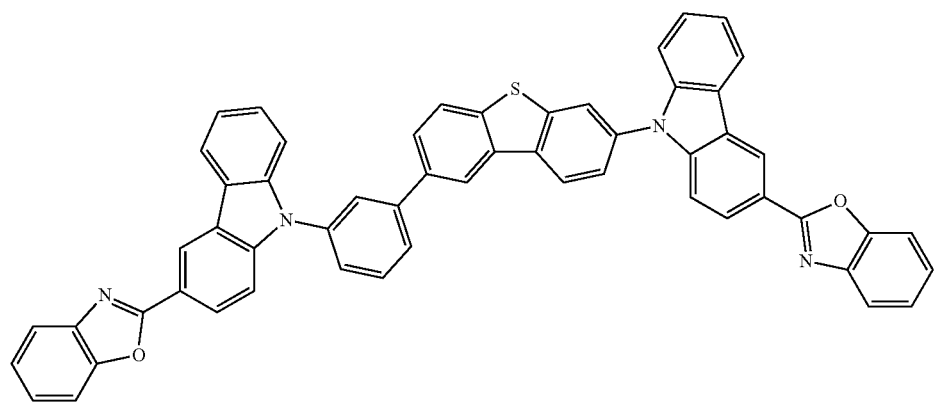
P-79
P-83
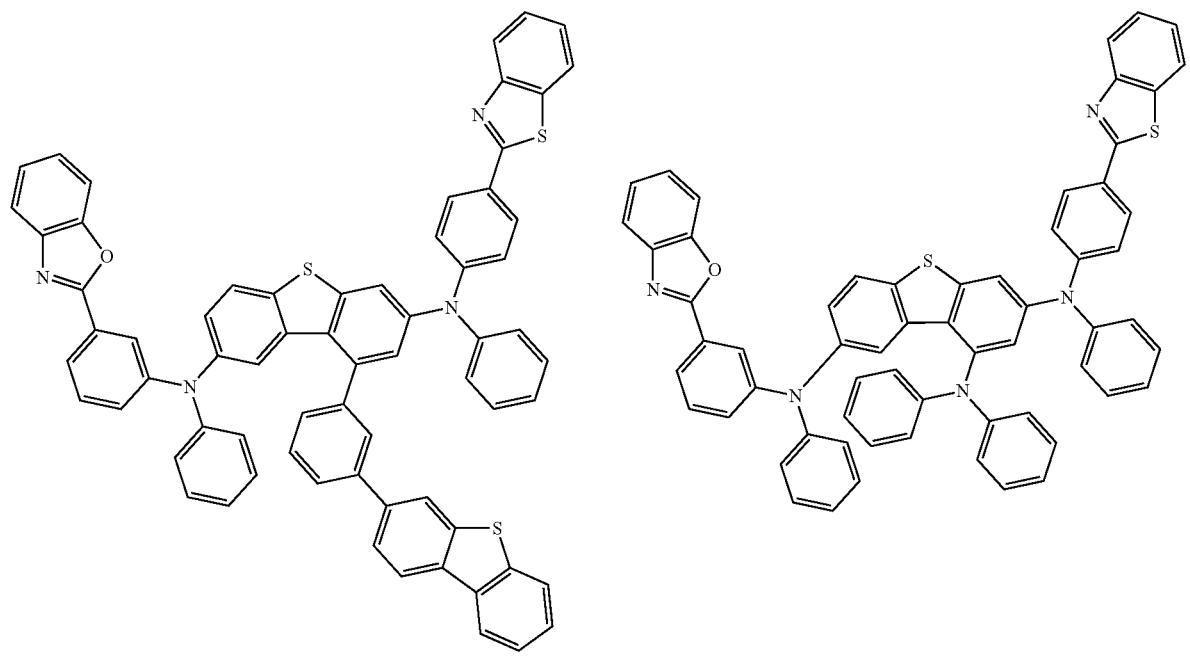
P-85
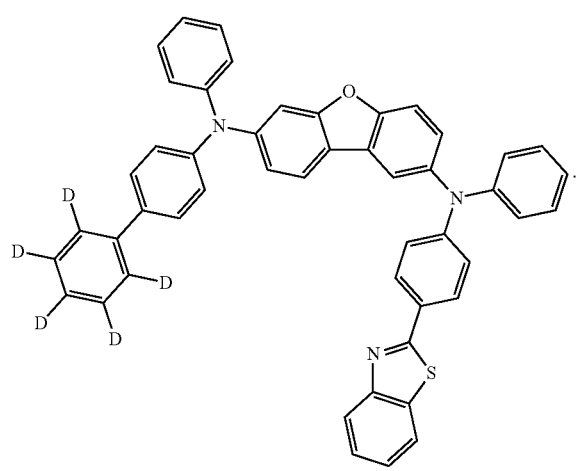

8. The organic electric element according to claim 1, wherein the organic material layer comprises at least one of a hole injection layer, a hole transport layer, a light emitting auxiliary layer, a light emitting layer, an electron transport auxiliary layer, an electron transport layer, and an electron injection layer, and at least one of the hole injection layer, the hole transport layer, the light emitting auxiliary layer, the light emitting layer, the electron transport auxiliary layer, the electron transport layer, and the electron injection layer comprises the compound represented by the Formula 1-T.

9. The organic electric element according to claim 1, wherein the organic material layer comprises a first stack, a charge generating layer positioned on the first stack, and a second stack positioned on the charge generating layer, and the first stack comprises a first emitting layer, and the second stack comprises a second emitting layer.

\* \* \* \* \*